United States Patent
Reid

(10) Patent No.: US 10,561,650 B2
(45) Date of Patent: Feb. 18, 2020

(54) METHOD FOR TREATING A PROTOZOAL INFECTION

(71) Applicant: Christopher Brian Reid, Los Angeles, CA (US)

(72) Inventor: Christopher Brian Reid, Los Angeles, CA (US)

(*) Notice: Subject to any disclaimer, the term of this patent is extended or adjusted under 35 U.S.C. 154(b) by 0 days.

(21) Appl. No.: 16/039,134

(22) Filed: Jul. 18, 2018

(65) Prior Publication Data

US 2019/0008853 A1    Jan. 10, 2019

Related U.S. Application Data

(62) Division of application No. 15/241,308, filed on Aug. 19, 2016, now abandoned, which is a division of application No. 13/815,664, filed on Mar. 14, 2013, now abandoned.

(51) Int. Cl.

| | | |
|---|---|---|
| A61K 38/00 | (2006.01) | |
| A61K 31/496 | (2006.01) | |
| A61K 31/122 | (2006.01) | |
| A61K 31/12 | (2006.01) | |
| A61K 31/355 | (2006.01) | |
| A61K 31/375 | (2006.01) | |
| A61K 31/4164 | (2006.01) | |
| A61K 38/06 | (2006.01) | |
| A61K 45/06 | (2006.01) | |
| A61K 38/18 | (2006.01) | |
| A61K 36/00 | (2006.01) | |
| A61K 31/194 | (2006.01) | |
| A61K 31/327 | (2006.01) | |

(52) U.S. Cl.
CPC ........... *A61K 31/496* (2013.01); *A61K 31/12* (2013.01); *A61K 31/122* (2013.01); *A61K 31/194* (2013.01); *A61K 31/327* (2013.01); *A61K 31/355* (2013.01); *A61K 31/375* (2013.01); *A61K 31/4164* (2013.01); *A61K 36/00* (2013.01); *A61K 38/063* (2013.01); *A61K 38/1816* (2013.01); *A61K 45/06* (2013.01); *Y02A 50/389* (2018.01)

(58) Field of Classification Search
CPC combination set(s) only.
See application file for complete search history.

(56) References Cited

U.S. PATENT DOCUMENTS

| | | |
|---|---|---|
| 2,780,355 A | 2/1957 | Palermo et al. |
| 3,312,594 A | 4/1967 | Wilson, Jr. et al. |
| 4,209,513 A | 6/1980 | Torode et al. |
| 4,332,892 A | 6/1982 | Ptashne et al. |
| 4,497,157 A | 2/1985 | Durr et al. |
| 4,550,176 A | 10/1985 | Dockner et al. |
| 4,777,048 A | 10/1988 | Hersh et al. |
| 4,780,316 A | 10/1988 | Brox |
| 4,794,082 A | 12/1988 | Sigler |
| 4,839,174 A | 6/1989 | Baker et al. |
| 4,908,027 A | 3/1990 | Enscore et al. |
| 4,943,435 A | 7/1990 | Baker et al. |
| 4,981,687 A | 1/1991 | Fregly et al. |
| 5,004,610 A | 4/1991 | Osborne et al. |
| 5,037,698 A | 8/1991 | Brunel |
| 5,077,104 A | 12/1991 | Hunt et al. |
| 5,126,123 A | 6/1992 | Johnson |
| 5,167,242 A | 12/1992 | Turner et al. |
| 5,268,209 A | 12/1993 | Hunt et al. |
| 5,342,623 A | 8/1994 | Enscore et al. |
| 5,344,656 A | 9/1994 | Enscore et al. |
| 5,364,630 A | 11/1994 | Osborne et al. |
| 5,376,359 A | 12/1994 | Johnson |
| 5,376,381 A | 12/1994 | Weiner et al. |
| 5,389,634 A | 2/1995 | Fortin et al. |
| 5,462,745 A | 10/1995 | Enscore et al. |
| 5,508,038 A | 4/1996 | Wang et al. |
| 5,521,319 A | 5/1996 | Huber |
| 5,544,646 A | 8/1996 | Lloyd et al. |
| 5,567,439 A | 10/1996 | Myers et al. |
| 5,633,008 A | 5/1997 | Osborne |
| 5,698,155 A | 12/1997 | Grosswald et al. |
| 5,744,187 A | 4/1998 | Gaynor |
| 5,780,094 A | 7/1998 | King |
| 5,859,053 A | 1/1999 | Lesur et al. |
| 5,968,787 A | 10/1999 | Iwata et al. |
| 6,068,850 A | 5/2000 | Stevenson et al. |
| 6,290,985 B2 | 9/2001 | Ream et al. |

(Continued)

FOREIGN PATENT DOCUMENTS

| | | |
|---|---|---|
| WO | 1992001668 A1 | 2/1992 |
| WO | 1995030641 A1 | 11/1995 |

(Continued)

OTHER PUBLICATIONS

Minodier & Parola, Cutaneous leishmaniasis treatment, Travel Medicine and Infectious Disease (2007) 5, 150-158 (Year: 2007).*

Nassiri-Kashani, M., A randomized, double-blind, placebo-controlled clinical trial of itraconazole in the treatment of cutaneous leishmaniasis, J. Eur Acad Dermatol Venereol, Jan. 2005;(1):80-3 (Year: 2005).*

Keithly and Langrethi, Inefficacy of metronidazole in experimental infection of Leishmania donovani, L. Mexicana, and trypanosoma Brucei brucei, Am. J. Trop. Med Hyg., 32(3), 1983, pp. 485-496 (Year: 1983).*

(Continued)

*Primary Examiner* — Thomas S Heard

(74) *Attorney, Agent, or Firm* — Henry J. Cittone; Cittone Demers & Arneri LLP

(57) ABSTRACT

A method for reducing motility and number of *L. donovani* cells, said method comprising contacting the *L. donovani* cells with an effective amount of a composition, the composition comprising a combination of metronidazole and itraconazole, wherein the effective amount is sufficient to reduce motility of the *L. donovani* cells.

1 Claim, 1 Drawing Sheet

(56) References Cited

U.S. PATENT DOCUMENTS

Figure 1A:
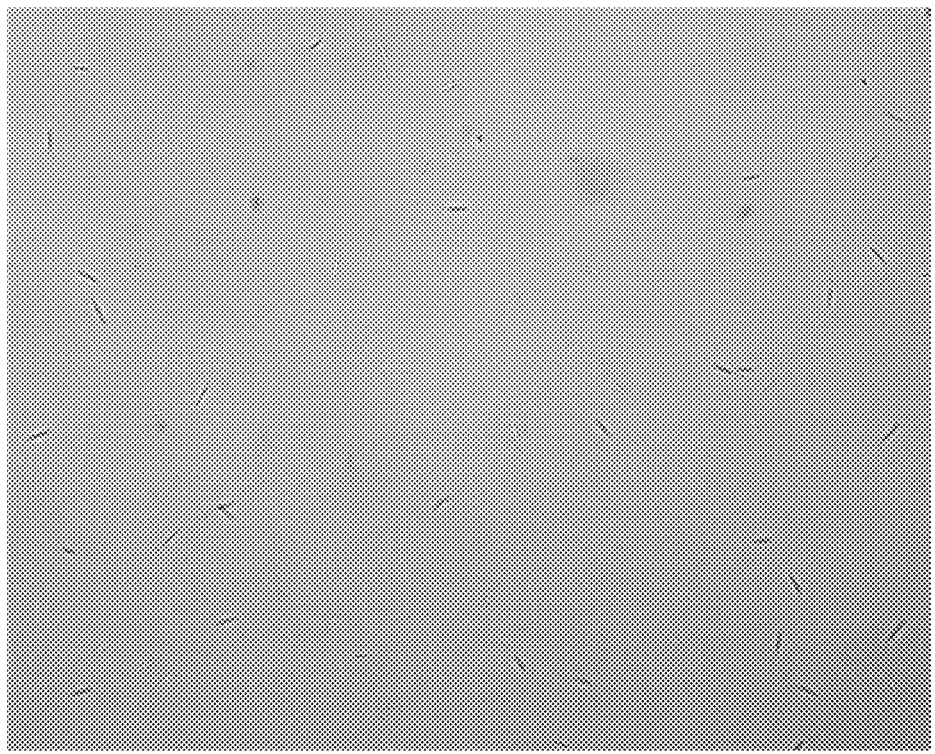

| | | | |
|---|---|---|---|
| 6,531,114 | B1 | 3/2003 | Gmunder et al. |
| 6,669,964 | B2 | 12/2003 | Greenberg et al. |
| 6,790,837 | B2 | 9/2004 | Heimbecher et al. |
| 6,838,094 | B2 | 1/2005 | Grimmett et al. |
| 6,863,902 | B2 | 3/2005 | Thosar et al. |
| 6,905,708 | B2 | 6/2005 | Li et al. |
| 7,011,846 | B2 | 3/2006 | Shojaei et al. |
| 7,078,052 | B2 | 7/2006 | Ream et al. |
| 2002/0077299 | A1 | 6/2002 | Babish |
| 2004/0162273 | A1 | 8/2004 | Achong et al. |
| 2004/0247705 | A1 | 12/2004 | Roberts |
| 2007/0021325 | A1 | 1/2007 | Byun et al. |
| 2008/0119483 | A1 | 5/2008 | Beverley |
| 2010/0021535 | A1 | 1/2010 | Mizutani et al. |

FOREIGN PATENT DOCUMENTS

| | | | |
|---|---|---|---|
| WO | 1997016405 | A1 | 5/1997 |
| WO | 1999013865 | A1 | 3/1999 |
| WO | 2000006120 | A1 | 2/2000 |
| WO | 2000025765 | A2 | 5/2000 |
| WO | 2002011706 | A2 | 2/2002 |
| WO | 2002083106 | A1 | 10/2002 |
| WO | 2004069224 | A2 | 8/2004 |
| WO | 2005065667 | A2 | 7/2005 |
| WO | 2006099687 | A1 | 9/2006 |
| WO | 2006102768 | A1 | 10/2006 |
| WO | 2007001484 | A2 | 1/2007 |
| WO | 2007098504 | A1 | 8/2007 |
| WO | 2007126915 | A1 | 11/2007 |
| WO | 2007129162 | A2 | 11/2007 |
| WO | 2008150814 | A2 | 12/2008 |
| WO | 2009020601 | A2 | 2/2009 |
| WO | 2009065065 | A1 | 5/2009 |
| WO | 2009067536 | A2 | 5/2009 |
| WO | 2009101263 | A2 | 8/2009 |
| WO | 2009126950 | A2 | 10/2009 |
| WO | 2009141450 | A2 | 11/2009 |
| WO | 2009153373 | A2 | 12/2009 |
| WO | 2010009186 | A1 | 1/2010 |
| WO | 2010013224 | A2 | 2/2010 |
| WO | 2010033580 | A2 | 3/2010 |
| WO | 2010057503 | A2 | 5/2010 |
| WO | 2010070675 | A2 | 6/2010 |
| WO | 2010103544 | A2 | 9/2010 |
| WO | 2010106191 | A1 | 9/2010 |
| WO | 2010109482 | A2 | 9/2010 |
| WO | 2010114801 | A1 | 10/2010 |
| WO | 2010118968 | A1 | 10/2010 |
| WO | 2010119300 | A2 | 10/2010 |
| WO | 2010127100 | A1 | 11/2010 |
| WO | 2010127191 | A1 | 11/2010 |
| WO | 2010129213 | A2 | 11/2010 |
| WO | 2010129337 | A2 | 11/2010 |
| WO | 2010137027 | A1 | 12/2010 |

OTHER PUBLICATIONS

Robert H. Foote, Effects of metronidazole, ipronidazole, and dibromochloropropane on rabbit and human sperm motility and fertility, Reproductive Toxicology 16 (2002) 749-755 (Year: 2002).*
Kappagoda, "Antiparasitic Therapy." Mayo Clinic Proceedings 86(6):561-583 Jun. 1, 2011.
Stefanson, "Dietary Regulation of Keap1/Nrf2/ARE Pathway: Focus on Plant-Derived Compounds and Trace Minerals." Nutrients 6(9):3777-3801 Sep. 19, 2014.
Wahab, "Anti-tumor Activities of Analogues Derived from the Bioactive Compound of Zingiber Zerumbet." International Journal of Cancer Research 4(4):154-159 Jan. 1, 2008.

* cited by examiner

US 10,561,650 B2

METHOD FOR TREATING A PROTOZOAL INFECTION

This application is a divisional of U.S. patent application Ser. No. 15/241,308 filed Aug. 19, 2016, which is a divisional of U.S. patent application Ser. No. 13/815,664 filed Mar. 14, 2013 the disclosures of which are hereby incorporated by reference in their entireties.

BACKGROUND OF THE INVENTION

Strikingly, a large number of serious chronic diseases (such as cardiovascular disease, diabetes, obesity, hyperlipidemia, PCOS and hypertension) have been observed to cluster in patients. Such clustering can be identified in as many as one in five people on the planet and its prevalence increases with age. The problem is particularly acute in industrialized countries. Thus, chronic diseases such as cardiovascular disease, diabetes, obesity, hyperlipidemia, and hypertension, represent serious causes of polypharmacy, morbidity and reduced longevity. They also pose tremendous economic burdens on individuals, families and societies. Therefore, the identification of compositions and formulations capable of preventing or treating one or a combination of these disorders is desirable.

In non-industrialized countries, infectious and parasitic diseases similarly threaten not only the lives of individuals, but the economic viability of families, communities, and societies as a whole. For example, protozoal illnesses continue to account for significant morbidity and mortality, especially in the tropical world. Malaria, endemic in to 90 countries in Africa, Asia, Oceania, South America, and the Caribbean, infects approximately 300-500 million people and kills 2.5 million people every year. Most of whom report lack of access or funds to purchase expensive artemisinin-based combination therapies Another protozoal illness, Leishmaniasis, affects 12 million people in 88 countries, mainly in the in the tropics and subtropics. Worldwide, there are approximately 1.5 million new cases of cutaneous leishmaniasis and 500,000 new cases of visceral leishmaniasis each year. In spite of the large number people suffering from this disfiguring disease and the 100% fatality rate of untreated leishmaniasis over 2 years, leishmaniasis remains on the official list of "Neglected Diseases" because current treatments are often ineffective or too costly for the affected populations.

BRIEF DESCRIPTION OF FIG. 1

Figure 1B:
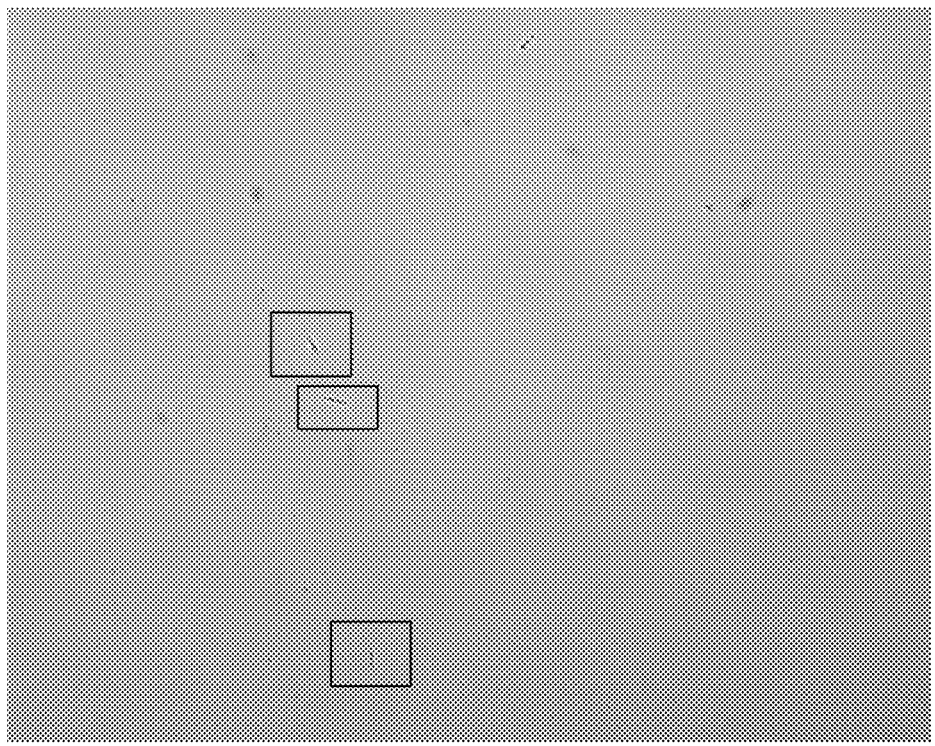

FIG. 1A (Control Panel A) depicts large number of highly motile *L. donovani* cells, which were observed microscopically, swimming at high speeds. FIG. 1B (Control Panel B) depicts far fewer motile *L. donovani* as is found in Control Panel A, 144 hours after treatment with metronidazole and itraconazole. The three boxes shown in FIG. 1B (Control Panel B) enclose the remaining *L. donovani*, which have lost motility after treatment with metronidiazole and itraconazole.

SUMMARY OF THE INVENTION

Virtually all patients could benefit from novel, efficacious drug formulations. The present invention provides novel compositions and inexpensive drug formulations for preventing and/or treating various conditions, diseases, maladies and for improving health and well-being in general. The present invention also provides corresponding methods for producing such formulations and compositions.

It has been taught that virtually all medications have the potential to cause significant side effects. It is also generally understood, accepted and taught that the various chronic diseases that cluster in patients CDCP as well as other disorders diseases and conditions (ODDC) have distinct mechanisms of disease and are therefore appropriately treated or prevented by providing multiple drugs with distinct mechanisms of action. These teachings have led to the phenomenon known as a "polypharmacy". Accordingly, patients requiring treatment for multiple conditions frequently suffer from the cumulative side effects of multiple drugs, as well as adverse drug-drug interactions related to polypharmacy. Polypharmacy is especially problematic in treatment of the elderly Hajjar et al., (2007) concluded that, "polypharmacy continues to increase and is a known risk factor for important morbidity and mortality."

Often, polypharmacy results in reduced efficacy of one or more drugs. In addition, a drug provided to treat one chronic condition may worsen another. For example, many anti-diabetes medications produce weight gain, thereby scuttling efforts and counteracting medications aimed at reducing patient obesity. Thus, it is medically desirable to provide single agents, compounds or drugs as monotherapies capable of preventing or treating multiple conditions, thereby avoiding polypharmacy. Likewise, combination therapies involving a reduced number of agents, compounds, or drugs are also desirable as still reducing the level and risks of polypharmacy. Therefore, the present invention provides compositions and formulations for reducing or eliminating polypharmacy. Likewise, an important feature of the present invention is the combination of naturally-occurring compounds named herein with other naturally-occurring compounds or with synthetic compounds. Such combinations may generally produce reduced side-effects as compared to combinations involving multiple pharmaceutical drugs (polypharmacy).

Embodiments, agents, compounds or drugs of the present invention replace an equal or larger number of approved drugs in treating a patient.

ODDC comprise all conditions and diseases known to those skilled in the medical art, as the compounds and formulations described herein relate to a common pathway of cellular injury, cellular dysfunction, cellular derangement, and inflammation. For example, the present invention also provides formulations for preventing and treating parasitic diseases.

It has likewise been taught that oral glutathione, though potentially useful, is not bioavailable in humans. Witschi, et al., (1992) teaches that "dietary glutathione is not a major determinant of circulating glutathione, and it is not possible to increase circulating glutathione to a clinically beneficial extent by the oral administration of a single dose of 3 g of glutathione." In contrast, the current invention provides compositions and formulations comprising oral glutathione and/or other agents, compounds, or drugs effective to increase intracellular glutathione concentration to a clinically beneficial extent. The current invention likewise provides effective compositions and formulations for administration via other routes.

The present invention relates to various agents, compounds and drugs named herein. The agents, compounds and drugs of the present invention comprise i. sesquiterpenes (e.g. Zerumbone, a naturally-occurring monosesquiterpene isolated from the rhizomes of *Zingiber zerumbet* Smith), ii. FDA approved drugs and iii. non-FDA approved drugs).

Zerumbone has previously been described with respect to its anti-inflammatory activity and its ability to selectively inhibit cellular survival; however zerumbone is more frequently used as a fragrance component. In the present invention we also describe the use of zerumbone and/or other agent(s), compound(s), or drug(s) of the present invention, alone or in combination with other agents, compounds or drugs, to treat or prevent a large variety of disorders and conditions for which the use of zerumbone and other agent(s), compound(s), or drug(s) of the present invention, alone or in combination with other agents, compounds or drugs, to treat or to prevent a large variety of disorders and conditions for which the use of agents or combinations has not been previously described or has been dismissed by prior teachings. Similarly, the present invention teaches compositions and formulations comprising other agents, compounds or drugs described herein, for uses and delivery that have not been previously described or that have been dismissed by prior teachings.

Thus, the present invention addresses the need for novel compositions, medicinal formulations and combination therapies capable of safely preventing or treating serious chronic diseases that cluster in patients (herein termed CDCP) as well as other disorders diseases and conditions (herein termed ODDC) ameliorable by these same compositions and formulations. Similarly, the compositions and formulations of the present invention are likewise aimed at treating conditions and injuries without acceptable forms of treatment, for example, traumatic brain injury.

In some embodiments, compositions for treating traumatic brain injury, blast-induced traumatic brain injury and/or penetrating brain injury comprise two or more of mannitol, a sesquiterpene, erythropoietin, an erythropoietin-like agent, Darbepoetin (Aranesp), Epocept (Lupin pharma), Epogen, Epogin, Eprex, Procrit, NeoRecormon, Recormon, Methoxy polyethylene glycol-epoetin beta (Mircera), Dynepo, Epomax, Silapo (Stada), Retacrit, Epocept, EPOTrust, Erypro Safe, Repoitin, Vintor, Epofit, Erykine, Wepox, Espogen, ReliPoietin, Shanpoietin, Zyrop, EPIAO (rHuEPO), and another agent, compound or drug named herein.

The present invention provides formulations for preventing or treating protozoal illnesses including, but not limited to Amoebiasis, Giardiasis, Trichomoniasis, African Sleeping Sickness, American Sleeping Sickness, Leishmaniasis, Balantidiasis, Toxoplasmosis, Malaria, and Babesiosis.

Additional Definitions

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "ameliorate" is meant decrease, suppress, attenuate, diminish, arrest, or stabilize the development or progression of a disease. As used herein, the meaning of "ameliorate" includes lessening an effect, or reducing damage, or minimizing the effect or impact of an action, activity, or function, and includes, for example lessening the deleterious effects of a disease or condition.

By "agent" is meant any small molecule chemical compound, antibody, nucleic acid molecule, or polypeptide, or fragments thereof.

By "modulation" is meant a change (increase or decrease) or alteration in the expression or activity levels or activity of a gene or polypeptide as detected by standard art known methods such as those described herein. As used herein, an alteration includes a 5% change in expression or activity levels, preferably a 25% change, more preferably a 40% change, and most preferably a 50% or greater change in expression or activity levels."

By "reduces" is meant a negative modulation of at least 5%, 25%, 50%, 75%, or 100%.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. Likewise, analog herein refers to those compounds structurally related to the compound, agent or drug in question and which retains characteristic biological properties of the compound, agent or drug.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

CDCP refers to the large number of serious chronic diseases such as cardiovascular disease, diabetes, obesity, hyperlipidemia, PCOS and hypertension that have been observed to cluster in patients.

ODDC comprise all conditions and diseases known to those skilled in the medical art other than chronic diseases that cluster in patients (CDCP).

As named and used herein, an agent, compound or drug of the present invention refers to the agent, compound or drug its analogs, and its derivatives including those derivatives described herein (e.g. glutathione conjugates, n-acetylcysteine conjugates, biotinylated derivatives, fluorinated derivatives, and derivatives having an NO donor moiety).

"Zerumbone" refers to zerumbone, a derivative of zerumbone, another sesquiterpene, a derivative of another sesquiterpene, or other practicable agent, compound named herein.

DETAILED DESCRIPTION OF THE INVENTION

Before describing the present invention in detail, it is to be understood that this invention is not limited to the particular embodiments, techniques, active agents, and the like as such may vary. It is also to be understood that the terminology used herein is for describing particular embodiments only, and is not intended to be limiting.

The present invention addresses the need for compounds, drugs, compositions and medicinal formulations capable of preventing or treating serious chronic diseases, such as those that cluster in patients (herein termed CDCP), as well as other disorders diseases and conditions (herein termed ODDC) ameliorable by these compositions and formulations.

In a first aspect, the present invention relates to compositions and medicinal formulations applicable in the treatment of patients with multiple diseases, disorders or conditions. It has commonly been taught that virtually all medications pose significant, adverse, side-effects. Moreover, patients requiring treatment for multiple conditions are typically treated with multiple agents, compounds or drugs, and, as a result, frequently suffer injury due to drug-drug interactions.

Therefore, it is medically desirable to provide monotherapies comprising single agents, compounds or drugs capable of preventing or treating multiple conditions or diseases. Likewise, it is medically desirable to provide combinational formulations and compositions containing a small number of agents, compounds, or drugs capable of treating multiple conditions. Such compositions and formulations will be effective, yet demonstrate reduced tendency to drug-drug interactions as compared to the combinations of approved drugs commonly used to prevent or treat the same group diseases, disorders and conditions.

It has been taught that glutathione is not orally bioavailable. Witschi, et al. (1992) concluded that, "dietary glutathione is not a major determinant of circulating glutathione, and it is not possible to increase circulating glutathione to a clinically beneficial extent by the oral administration of a single dose of 3 g of glutathione." Consequently, reduced glutathione is normally given via intramuscular injection or intravenous injection, but not orally.

Witschi et al, may have conflated a failure on the part of dietary glutathione to increase plasma concentration with a failure to have clinical benefit. The problem with the conclusion of Witschi et al., (1992) arises with respect to the phrase "clinically beneficial extent". While it is possible that the plasma concentration does not change appreciably after oral administration (for the reasons proposed above), intracellular glutathione may nevertheless increase to a "clinically beneficial extent" in conjunction with oral glutathione dosing. This would especially be the case if the increase in intracelluar glutathione associated with oral administration were enhanced by a second agent (such as those described herein) that defied or overrode the mechanisms that one would expect to tightly regulate and limit excursions in intracellular glutathione concentration.

Thus, while not being bound by theory, applicant believes that Witschi et al., direct toward plasma glutathione concentration while inappropriately linking plasma glutathione and clinical benefit. In contrast, the applicants propose that clinical benefits can be achieved through oral doses of glutathione in combination with second agents—even if a rise in plasma glutathione following an oral dose is very transient or absent. The applicant further proposes that these clinical benefits will accrue across a wide spectrum of diseases, disorders, and conditions. Thus, the present invention provides for prevention or treatment of multiple disorders with the same agent(s), compound(s) or drug(s), as well as a beneficial reduction of polypharmacy and its associated morbidity and mortality.

In a second aspect, this invention relates to i. compositions or formulations for achieving clinical benefit comprising the oral administration of gluthianone; ii. Compositions or formulations for increasing intracellular gluthianone (GSH) content; iii. Compositions or formulations comprising conjugates of gluthianone with other agents, compounds or drugs listed or described herein; iv. compositions or formulations comprising conjugates of glutathione that increase the bioavailability and/or effectiveness of an agent, compound or drug; v. compositions or formulations comprising conjugates of glutathione with other agents, compounds, or drugs that provide mutual, coordinated absorption; and vi. Compositions or formulations that increase bioavailability of an agent, compound or drug of the present invention.

In a third aspect, the present invention relates to compounds, drugs, and agents, or compositions and formulations that improve drug action, e.g. reduce chemotherapeutic resistance including, but not limited to, cancer chemotherapeutic resistance, chemotherapeutic resistance to anti-hypertensive agents, cardioprotectant agents, chemotherapeutic resistance to anti-obesity agents, fertility agents, chemotherapeutic resistance to glycemic control agents, chemotherapeutic resistance to anti-hyperlipidemic agents, chemotherapeutic resistance to an anti-atherosclerotic agent, etc.

In a fourth aspect, the invention relates to novel formulations and delivery methods that increase the availability of various compounds, agents and drugs to the body, especially via the oral route, particularly when such drugs and compounds otherwise lack significant oral bioavailability.

In some embodiments the novel formulations and delivery methods likewise provide for increased palatability, especially via the oral route, particularly when such drugs and compounds otherwise are unpalatable.

The invention also specifically covers the use of compounds, agents, and drugs specified or named herein (and their analogs), in conjunction with other anti-hypertensive agents, cardioprotectant agents, anti-obesity agents, fertility agents, glycemic control agents, anti-hyperlipidemic agents, anti-atherosclerotic agents, anti-cancer agents, anti-chemotherapeutic resistance agents, and other approved agents and drugs as part of combination therapies and medicinal formulations.

In a fifth aspect, the present invention relates to a method of identifying agents, compounds or drugs useful in preventing or treating CDCP related diseases and conditions as well as other disorders diseases and conditions treatable or preventable.

The method may comprise determining whether a compound reduces VEGF (vascular endothelial growth factor) activity, and identifying the compound that reduces VEGF activity as a drug candidate.

The method may also comprise administering a candidate agent, compound, or drug to an animal or contacting cells in vitro or in vivo with a candidate agent, compound, or drug and assaying the activity of the VEGF promoter in response.

The invention also relates to a method for reducing VEGF promoter activity in a cell in a human in need thereof.

Finally, the invention relates to compositions and formulations capable of extending the life span of a cell, tissue, organ, or organism (especially a human). If nothing else, cancerous cell behavior demonstrates that cellular immortality and cell death are epigenetically determined phenomena. The present invention provides for compositions and formulations that can modulate re-program and/or re-set the "expiry date" inherent to all living things, thereby extending lifespan.

In part, the invention relates to a method for preventing or treating a CDCP or ODDC disease or condition. The method comprises administering a therapy, composition or formulation comprising zerumbone and/or other agent(s), compound(s), or drug(s) of the present invention.

In some embodiments, the invention relates to a composition or formulation comprising zerumbone and/or other an equivalent effective amount of other agent(s), compound(s), or drug(s) of the present invention.

In part, the invention relates to a method for preventing chemotherapeutic resistance (including cancer chemotherapeutic resistance). The method comprises administering a composition or formulation comprising zerumbone and/or other agent(s), compound(s), or drug(s) of the present invention.

In part, the invention relates to a method for preventing chemotherapeutic resistance (including cancer chemotherapeutic resistance). The method comprises administering a composition or formulation comprising agent(s), compound(s), or drug(s) of the present invention (such as those named herein).

In part, the invention relates to methods for administering a compound, agent or drug with anti-hypertensive, anti-obesity, glycemic control, anti-hyperlipidemic, anti-atherosclerotic, and/or an anti-chemotherapeutic resistance properties to an animal, an invertebrate, a vertebrate, an insect, fish, amphibian, bird, mammal or to a human in need thereof. The method comprises administering a composition or formulation comprising zerumbone and/or other agent(s), compound(s), or drug(s) of the present invention.

Non-limiting examples of other disorders (herein termed "other disorders", or ODDC) preventable or ameliorated by administration of the compositions and formulations described herein include, but are not limited to inflammatory diseases, oncological diseases, genetic diseases, ischemic diseases, infectious diseases, neurological diseases, hematological diseases, kidney diseases, vascular diseases, dermatological diseases, opthalmological diseases, rheumatoid diseases, orthopedic diseases, gynecological diseases, obstetric diseases, pediatric diseases, etc. Additional non-limiting examples include sepsis, contrast-induced nephropathy, chronic kidney disease, pulmonary fibrosis, hypoxic conditions, chemical-induced lung injury, respiratory distress disorder, anon gap acidosis, nephritis, lupus, interstitial lung disease, graft dysfunction, hepatitis, acute kidney injury, noise-induced hearing injuries, poison ingestion, retinopathy, neurotoxicity, cancer-induced injury such as ototoxicity, respiratory infections, autism, conditions involving vasospasm, and conditions considered treatable by provision of n-acetylcysteine, injectable reduced glutathione, or a known intracellular glutathione enhancing agent.

It should be understood, however, that the present invention, with respect to all of its aspects, covers the use of another compound, agent, or drugs specified herein in combination with zerumbone or in place of zerumbone so long as the ultimate composition or formulation is novel and effective.

In some embodiments, the agents, compounds, or drugs of the present invention comprise an allicin and an amino acid(s).

In some embodiments, the compositions and formulations of the present invention will be ones useful for preventing or treating conditions and diseases related to the depletion of glutathione or to insufficient glutathione.

In some embodiments, the agents, compounds or drugs of the present invention are incorporated into compositions or formulations for reducing polypharmacy.

In one embodiment, the compositions and/or formulations of the present invention reduce the risk of drug-drug interaction in a patient.

In some embodiments, the agents, compounds or drugs of the present invention are incorporated into compositions or formulations for treating or preventing signs and symptoms of CDCP and ODDC In some embodiments, the compositions and formulations of the present invention are useful for preventing or treating a Neurodegenerative disease or condition. Examples of such neurodegenerative diseases include Parkinson disease, Alzheimer disease, Multiple Sclerosis, Schizophrenia, Dementia, and Huntington's disease.

In some embodiments, the compositions and formulations of the present invention are useful for preventing or treating a mental illness.

In some embodiments, the compositions and formulations of the present invention are useful for preventing or treating diseases or conditions related to Aging. Examples of aging related diseases include Arthritis, Diabetes, Osteoarthritis, Cataracts, Macular Degeneration and Prostate enlargement. Many other aging related diseases represent a manifestation of decreased cellular telomerase and they likewise are considered preventable or treatable with the compositions and formulations described herein.

In some embodiments, the compositions and formulations of the present invention are useful for preventing or treating diseases or conditions related to Cancer. Examples of cancer related diseases and conditions include Prostate cancer, Breast cancer, Lung cancer, colorectal cancer, Bladder cancer, Uterine cancer, Ovarian cancer, Lymphoma, Skin cancer, Stomach cancer, Liver cancer, wasting diseases, and other cancers.

In some embodiments, the compositions and formulations of the present invention are useful for preventing or treating diseases or conditions related to Liver Dysfunction. Examples of such conditions and diseases include Toxic Hepatitis, Viral Hepatitis (A, B, and C), Chronic Hepatitis, Acute alcoholic Hepatitis, Alcoholic Hepatic fibrosis, Hepatic toxin exposure, and Cirrhosis.

In some embodiments, the compositions and formulations of the present invention are useful for preventing or treating diseases or conditions related to Lung dysfunction. Examples of such diseases and conditions include Asthma, Emphysema, Pneumonia, Bronchitis (chronic and acute), Cystic fibrosis, Pulmonary fibrosis, Chronic obstructive pulmonary disease (COPD), Adult respiratory distress syndrome (ARDS).

In some embodiments, the compositions and formulations of the present invention are useful for preventing or treating diseases or conditions related to the Cardiovascular System. Examples of such diseases and conditions include Ischemia, Atherosclerosis & its consequences, Heart failure, Heart Attack, Reperfusion injury, Kidney failure, High blood pressure, Stroke, Impaired circulation, vasculitis, and various viral and non-viral carditis In some embodiments, the compositions and formulations of the present invention are useful for preventing or treating diseases or conditions related to the Digestive System. Examples of conditions and diseases related to the Digestive System include inflammatory bowel disease, Ulcerative colitis, Crohn's disease, Gastritis, Stomach cancer, Pancreatitis, Peptic ulcer disease.

In some embodiments, the compositions and formulations of the present invention are useful for preventing or treating diseases or conditions related to Kidney Failure & Dialysis, Examples of such diseases and conditions include Kidney failure, Renal toxicity, and Injury related to dialysis.

In some embodiments, the compositions and formulations of the present invention are useful for treating Infectious diseases.

In some embodiments, the compositions or formulations of the present invention are utilized as anti-infectives (e.g. antibiotics, anti-microbials, anti-fungals, and antivirals, anti-helminthics, etc,)

In some embodiments, the compositions and formulations of the present invention are useful for preventing or treating Immune System related diseases and conditions. Such diseases and conditions include viral infection, HIV and AIDS, Toxic Hepatitis & cirrhosis, Viral hepatitis (type A, B, & C), Herpes virus infection, Common Cold, various Bacterial infections, Chronic fatigue syndrome, and autoimmune dysfunction.

In some embodiments, the compositions and formulations of the present invention are useful for preventing or treating Skin Disorders. Examples of such diseases and conditions include Pruritus, Psoriases, Eczema, SLE (lupus), Vasculitis, Polymyositis, Mycosis fungoides, Scleroderma Pemphigoid, Atopic dermatitis, Contact dermatitis, Sebborrheic dermatitis, Dermatitis herpetiformis, Acne conglobata, Acne vulgaris, Vitiligo, Alopecia areata, and UV radiation skin damage.

The invention also provides compositions and formulations (including but not limited to oral and topical compositions, and formulations) for promoting hair growth.

In some embodiments, the compositions and formulations of the present invention are useful for preventing or treating diseases and conditions related to the Eye, Ear, Nose, Throat & Teeth. Such conditions and diseases include Cataract, Glaucoma, Macular degeneration, Hearing loss, Ear infection, Sinusitis, Periodontal (gum) disease, and upper respiratory tract disease In some embodiments, the compositions and formulations of the present invention are useful for preventing or treating diseases and conditions related to the Pregnancy, Lactation & Childbirth. Examples of such disorders include Pre-eclampsia, Eclampsia Hypertension, and Diabetes.

In some embodiments, the compositions and formulations of the present invention are useful for treating neurological disorders such as schizophrenia, multiple sclerosis, epilepsy, seizures, depression and bipolar disorder, In some embodiments, the compositions and formulations of the present invention are useful for treating fragile X syndrome.

In some embodiments, the compositions and formulations of the present invention are useful for preventing or treating injuries and conditions related to Exercise & Athletic Performance. Such conditions and diseases may, for example, occur in the context of over training (e.g. Over-Training Syndrome) & the related cellular stress.

In some embodiments, the compositions and formulations of the present invention are useful for treating a newborn.

In some embodiments, the compositions and formulations of the present invention are useful for treating a child.

In some embodiments, the compositions and formulations of the present invention are useful for treating an adult human.

In some embodiments, the compositions and formulations of the present invention are useful for preventing or treating diseases and conditions related to the Prostate such as prostate enlargement and prostate cancer.

In some embodiments, the compositions and formulations of the present invention are useful for preventing or treating diseases and conditions related to hormonal influences such as loss of hair and fertility.

In some embodiments, the compositions and formulations of the present invention are useful for preventing or treating diseases and conditions related to toxic exposures.

In some embodiments, the compositions and formulations of the present invention are useful for preventing or treating diseases and conditions related to toxic drug exposures.

In some embodiments, the compositions and formulations of the present invention are useful for increasing telomerase activity in a cell when such an increase is desirable or preventing or treating diseases and conditions related to reduced or insufficient telomerase activity.

In some embodiments, the compositions and formulations of the present invention are useful for the alleviation of pain, inhibition of platelet aggregation, lowering of fever and for prevention of cardiovascular disorders with reduced toxicity and/or reduced polypharmacy.

In some embodiments, the compositions and formulations of the present invention are useful for vasorelaxant, anti-anginal, anti-inflammatory, analgesic and anti-thrombotic activity with lower gastrointestinal toxicity as compared to aspirin.

In a one embodiment, chronic use of the compositions or formulations of the present invention extend the lifespan of a cell, a tissue, an organ or an organism.

In a one embodiment, chronic use of the compositions or formulations of the present invention extend the lifespan of a human.

In one embodiment, the compositions or formulations of the present invention are utilized as anti-infectives (e.g. antibiotics, anti-microbials, anti-fungals, and antiviral s, anti-protozoals, anti-helminthics, etc.).

Furthermore, the compositions and formulations of the present invention may, in some embodiments, also be beneficial in critical surgical patients, patients in intensive care settings, patients receiving hemodialysis.

In another part, the invention relates to compositions and formulations for reducing an animal's body fat, increasing energy expenditure, and increasing oxygen consumption. Such activity represents organismal responses that may be assayed as a means of identifying compounds, drugs, and medicinal formulations suitable for preventing or treating CDCP, diseases related to CDCP, and/or chemotherapeutic resistance. Likewise, these organismal responses may be assayed to measure the efficacy of such compounds, drugs, and medicinal formulations.

In a further part, the invention relates to compositions and formulations for increasing lipolysis, increasing expression of uncoupling protein 2 (UCP2) and beta-oxidation genes, decreasing expression of lipogenic genes in white adipose tissue, thereby increasing utilization and decreasing synthesis of fatty acids. Such activity represents organismal responses that may be assayed as a means of identifying compounds, drugs, and medicinal formulations suitable for preventing or treating CDCP, diseases related to CDCP, and/or chemotherapeutic resistance. Likewise, these organismal responses may be assayed to measure the efficacy of such compounds, drugs, and medicinal formulations.

In a further part, the invention relates to compositions and formulations for increasing UCP1, 2 and 3 expression in brown adipose tissue (BAT), thereby increasing thermogenesis. Such activity represents organismal responses that may be assayed as a means of identifying compounds, drugs, and medicinal formulations suitable for preventing or treating CDCP, diseases related to CDCP, and/or chemotherapeutic resistance. Likewise, these organismal responses may be assayed to measure the efficacy of such compounds, drugs, and medicinal formulations.

In a further part, the invention relates to compositions and formulations for improving ovulatory function (and thus fertility) in a female in need of such improvement, regularizing her menstrual cycle, and reducing hirsutism, Such activity represents organismal responses that may be assayed as a means of identifying compounds, drugs, and medicinal formulations suitable for preventing or treating CDCP, diseases related to CDCP, and/or chemotherapeutic resistance. Likewise, these organismal responses may be assayed to measure the efficacy of such compounds, drugs, and medicinal formulations.

In a further part, the invention relates to compositions and formulations for lowering levels of circulating carbohydrate, preventing or treating age-related obesity, preventing or treating diet-related obesity, and preventing or treating steatosis. Such activity represents organismal responses that may be assayed as a means of identifying compounds, drugs, and medicinal formulations suitable for preventing or treating CDCP, diseases related to CDCP, and/or chemotherapeutic resistance. Likewise, these organismal responses may be assayed to measure the efficacy of such compounds, drugs, and medicinal formulations.

In a further part, the invention relates to compositions and formulations for preventing or treating chronic hyperglycemia, and preventing or treating diet-induced diabetes. Such activity represents organismal responses that may be assayed as a means of identifying compounds, drugs, and medicinal formulations suitable for preventing or treating CDCP, diseases related to CDCP, and/or chemotherapeutic resistance. Likewise, these organismal responses may be assayed to measure the efficacy of such compounds, drugs, and medicinal formulations.

In a further part, the invention relates to compositions and formulations for preventing or treating chemotherapeutic resistance in a cell, tumor, or cancer cell. Such activity represents organismal responses that may be assayed as a means of identifying compounds, drugs, and medicinal formulations suitable for preventing or treating CDCP, diseases related to CDCP, and/or chemotherapeutic resistance. Likewise, these organismal responses may be assayed to measure the efficacy of such compounds, drugs, and medicinal formulations.

In one aspect, the invention relates to compositions and formulations with anti-hypertensive agent, cardioprotectant agent, anti-obesity agent, glycemic control agent, anti-hyperlipidemic agent, an anti-atherosclerotic agent, and/or an agent preventing or treating chemotherapeutic resistance.

In some embodiments, the compositions, and formulations of the present invention are utilized to counteract a high fat diet.

In some embodiments, the compositions, and formulations of the present invention are utilized to counteract a diet of excessive calories.

In some embodiments, a sesquiterpene (e.g. zerumbone) and/or other agent(s), compound(s), or drug(s) of the present invention, with or without reduced glutathione, is provided to reduce resistance to an approved drug, including, but not limited to anti-cancer drugs, glycemic control drugs, anthypertensie drugs, lipid reducing drugs, etc.

In some embodiments, a sesquiterpene and/or other agent(s), compound(s), or drug(s) of the present invention is provided (with or without reduced glutathione) to reduce resistance to an FDA over-the-counter (OTC) drug.

Vitamin C may be provided whenever reduced glutathione is selected for inclusion in the compositions or formulations of the present invention in an amount to 0.5% w/v as needed. It should be understood that "zerumbone" as well as the names of the other sesquiterpenes, FDA approved drugs, and non-FDA approved drugs, as used herein, refers to the naturally or synthetically obtained agent, compound or drug, as well as its analogs and derivatives (e.g. a zerumbone-GSH conjugate described in the examples below).

It should also be understood that the present invention covers the combination of sesquiterpenes, FDA approved drugs, and non-FDA approved drugs (e.g. zerumbone, its analogs, or its derivatives) with other agent(s), compound(s), or drug(s) of the present invention.

It should also be understood that the present invention covers all compositions and formulations wherein a sesquiterpene, e.g. zerumbone, its analogs, or its derivatives are replaced in those compositions or formulations with other agent(s), compound(s), or drug(s) of the present invention.

In other embodiments, a sesquiterpene, e.g. zerumbone, and/or other agent(s), compound(s), or drug(s) of the present invention with or without reduced glutathione, is used in combination with approved drugs to provide enhanced anti-microbial action versus a targeted pathogen. In other embodiments, a sesquiterpene, e.g. zerumbone, and/or other agent(s), compound(s), or drug(s) of the present invention is used (with or without reduced glutathione) in combination with OTC drugs to provide enhanced anti-microbial action versus a targeted pathogen.

Such compositions and formulations may comprise biological molecules and small molecules as well as inorganic and organic compounds.

The term "composition or formulation" also refers to a substance, e.g., a compound, cell, etc., that limits cellular dysfunction and maintains normal function by preventing or treating the consequences of CDCP or disorders related to CDCP.

Disease related activity (including signs and symptoms of disease) is considered reduced according to the invention if it is reduced at least about 10%, preferably, at least about 20%, more preferably at least about 30%, even more preferably at least about 40%, and most preferably at least about 50% or more than in the absence of the compound. Optimally, at least about 70%, more optimally at least about 85%, and most optimally 100% of the symptoms or signs of CDCP, or a disease related to CDCP, are reduced in vitro, ex vivo, or in vivo.

The act of determining whether a composition or formulation modulates disease or condition related activity at the tissue, organ or organismal level further includes measuring the parameters by which the disease or condition is defined.

For example, the compositions and formulations of the invention modulate one or more of the following: tissue inflammation or swelling; pro-atherogenic cytokine production by endothelial cells, endothelial dysfunction, an invasion of blood vessel walls by monocytes, conversion of monocytes/macrophages to foam cells, smooth muscle proliferation, smooth muscle migration from tunica media to intima, plaque initiation, plaque progression, and plaque rupture; production of adipokines (e.g. TNF-alpha, IL-6, leptin, plasminogen activator inhibitor-1 (PAI-1), angiotensinogen, resistin, and C-reactive protein (CRP) by fat cells; an increase in plasma cholesterol, an increase in plasma LDL, an increase in plasma triacylglycerols, a decrease in plasma HDL; an increase in blood glucose, an increase in fasting blood glucose, glucose intolerance, hyperinsulinemia, insulin resistance, HbA1, a dependence upon exogenous insulin; systolic and/or diastolic blood pressure, an angiotensin II, microalbuminuria; or cellular resistance to a chemotherapeutic agent.

In various embodiments, the formulation for preventing or treating diseases related to CDCP, such as cardiovascular disease, diabetes, obesity, PCOS, steatosis, hyperlipidemia, and hypertension, as well as chemotherapeutic resistance, comprises one or more compounds and drugs selected from those named herein.

Anti-atherosclerotic activity refers to a composition's or formulation's ability to induce a beneficial effect on blood vessels in vitro, ex vivo, or in vivo administration of the composition or formulation. Such beneficial effects include, but are not limited to preventing or reducing the likelihood of one or more of the following events: pro-atherogenic cytokine production by endothelial cells, endothelial dysfunction, an invasion of blood vessel walls by monocytes, conversion of monocytes/macrophages to foam cells, lipid oxidation, smooth muscle proliferation, smooth muscle migration from tunica media to intima, plaque initiation, plaque progression, and plaque rupture.

Anti-obesity activity refers to a composition's or formulation's ability to induce a beneficial effect regarding excess weight gain upon in vitro, ex vivo, or in vivo administration of the composition or formulation. Such beneficial effects include, but are not limited to preventing or reducing the likelihood of one or more of the following events: production of adipokines (e.g. TNF-alpha, IL-6, leptin, plasminogen activator inhibitor-1 (PAI-1), angiotensinogen, resistin, and-reactive protein (CRP)) by fat cells.

Anti-hyperlipidemic activity refers to a composition's or formulation's ability to induce a beneficial effect on lipid levels upon in vitro, ex vivo, or in vivo administration of the composition or formulation. Such beneficial effects include, but are not limited to preventing or reducing the likelihood of one or more of the following events: an increase in plasma cholesterol, an increase in plasma LDL, an increase in plasma triacylglycerols, and a decrease in plasma HDL.

Glycemic control refers to a composition's or formulation's ability to induce a beneficial effect on glucose levels, insulin levels, glucose tolerance, and/or insulin tolerance upon in vitro, ex vivo, or in vivo administration of the composition or formulation. Such beneficial effects include, but are not limited to preventing or reducing the likelihood of one or more of the following events: an increase in random blood glucose, an increase in fasting blood glucose, glucose intolerance, hyperinsulinemia, insulin resistance, an increase in HbA1, an increased, an increased dependence upon exogenous insulin.

Anti-hypertensive activity refers to a composition's or formulation's ability to induce a beneficial effect upon in vitro, ex vivo, or in vivo administration of the composition or formulation. Such beneficial effects include but are not limited to preventing or reducing the likelihood of one or more of the following events: an increase in systolic and/or diastolic blood pressure, an increase in angiotensin II, and an increase in microalbuminuria.

Anti-chemotherapeutic resistance activity refers to a composition's or formulation's ability to induce a beneficial effect upon in vitro, ex vivo, or in vivo administration of the composition or formulation. Such beneficial effects include, but are not limited to preventing or reducing the likelihood of one or more of the following events: cellular resistance to a chemotherapeutic agent as demonstrated by increased or persistent dysfunction in spite of the application of an otherwise effective chemotherapeutic agent.

Anti-CDCP activity refers activity refers to a composition's or formulation's ability to induce a beneficial effect upon in vitro, ex vivo, or in vivo administration of the composition or formulation. Such beneficial effects include, but are not limited to preventing or reducing the likelihood of one or more of the following events: pro-atherogenic cytokine production by endothelial cells, endothelial dysfunction, an invasion of blood vessel walls by monocytes, conversion of monocytes/macrophages to foam cells, smooth muscle proliferation, smooth muscle migration from tunica media to intima, plaque initiation, plaque progression, and plaque rupture; production of adipokines (e.g. TNF-alpha, IL-6, leptin, plasminogen activator inhibitor-1 (PAI-1), angiotensinogen, resistin, and C-reactive protein (CRP)) by fat cells; an increase in plasma cholesterol, an increase in plasma LDL, an increase in plasma triacylglycerols, a decrease in plasma HDL; an increase in blood glucose, an increase in fasting blood glucose, glucose intolerance, hyperinsulinemia, insulin resistance, an increase in HbA1, an increased dependence upon exogenous insulin; an increase in systolic and/or diastolic blood pressure, an increase in angiotensin II, an increase in microalbuminuria; or cellular resistance to a chemotherapeutic agent.

In one aspect, the invention relates to a method for preventing or treating a variety of diseases and conditions including chronic diseases related to CDCP, such as cardiovascular disease, diabetes, obesity, PCOS, steatosis, hyperlipidemia, and hypertension and other disorders and conditions. The method comprises administering a composition or formulation comprising a sesquiterpene, e.g. zerumbone and/or other agent(s), compound(s), or drug(s) of the present invention.

In some embodiments, the composition or formulation further comprises an additional agent, drug or compound such as an FDA approved agent(s), compound(s) or drug(s) or non-FDA approved agent(s), compound(s) or drug(s).

In a one embodiment, the composition or formulation comprises glutathione, especially reduced glutathione.

In a one embodiment, the composition or formulation comprises an agent(s) or compound(s) extracted from ginger, such as, zingerone, a gingerol, or a shogaol.

In a one embodiment, the composition or formulation comprises an amino acid(s). In a one embodiment, the composition or formulation comprises L-cysteine.

In a one embodiment, the compositions or formulations further comprise another natural agent, compound, or drug such as a flavone or flavonoid (e.g. see USDA Database for the Flavonoid Content of Selected Foods), especially a 6,3-dimethoxyflavone or a 5,7-dimethoxyflavone.

In one embodiments, the analogs/derivatives of the present inventions are derived from a sesquiterpene, e.g. zerumbone and/or other agent(s), compound(s), or drug(s) of the present invention, a sesquiterpene, a sesquiterpenoid, a sesquiterpene lactone (e.g. lactucin, lactuopicrin, 8-deoxylactucin, picriside A, crepidiaside A, jacquinellin, jacquinellin glycoside, chamissonolide, helenalin, alantolactone, dehydrocostus lactone, costunolide), a sesquiterpene sulfate, reduced glutathione, auraptene, ethacrynic acid, curcumin, a curcuminoid, hispolon, dehydroxyhispolon, methoxyhispolon, bisdemethylcurcumin, hispolon methyl ether, hydroxyhispolon, methoxyhispolon methyl ether, a triterpenoid (e.g. Betulinic acid), zingerone, reservatrol, vanillin, rosmarinic acid, a methoxyflavone, a sesquiperetene, n-acetylcysteine, trimethylglycine, folinic acid, folic acid, an amino acid, an ATF4 modulator, flavone, a flavonoid, quercetin, a shogaol (e.g. 6-shogaol), a gingerol (e.g. 6-gingerol), zingerol, kavalactone, sulforaphane, allyl-, butyl- and phenylethyl-isothiocyanate, chlorophyllin, alpha-lipoic acid, allicin, plumbagin, protandim, capsaicin, a capsaicinoid, piperine, asafetida, eugenol, piperlongumine, pellitorine, zingiberine, tBHQ, CDDO-Im, MC-LR, epigallocatechin-3-gallate, a compound found in wasabi, modihydrocapsaicin, cafestol, 16-O-methyl cafestol, xanthohumol, isoxanthuhumolol, 5-O-caffeoylquinic acid, N-methylpyridinium, resveratrol, nootkatone, caffeic acid phenethyl ester, 3-O-Caffeoyl-1-methylquinic acid, silymarin, kahweol, garlic organosulfur compounds, lycopene, carnosol (rosemany), an avicin, oltipraz, CDDO, a neurite outgrowth promoting prostaglandin, vitamin D, a B vitamin, andrographolide, an amino acid, s-allylcysteine, Vitamin A, Vitamin C, Vitamin E, β carotene, trans-2-hexenal, cyclopentenone, ajoene, Dihydro-CDDO-trifluoroethyl amide, Hypochlorous acid, Fragrant unsaturated aldehydes (e.g. trans-cinnamaldehyde, safranal, 2,4-octadienal, citral, and trans-2,cis-6-nonadienal), 2-OHE, 4-OHE, bucillamine, momordin, momordol, momordicin I, momordicin II, momordicosides, momordicin-28, momordicinin, momordicilin, momordenol, momorcharin, cucurbitacin B, charantin, charantosides, goyaglycosides, α-eleostearic acid, 15,16-dihydroxy-α-eleostearic acid, antirheumatic gold(I) compounds, an avicin, dithiolethione, an approved drug, an OTC drug, and/or a compound, agent or drug extracted from cloves, black pepper, red chili, ginger, garlic, onion, fennel, bay leaves, nutmeg, saffron coriander and cinnamon (e.g. cinnamic aldehyde).

The present invention contemplates compositions and formulations comprising agents, compounds, or drugs selected from the group consisting of zingerbene, agoraspirol, amorphine, anhydro-β-rotunol, aromadendrine, azulene, bisabolene, bisabolol, cadalene, cadinene, cadrina-1,4-diene, caryophyllene, cedrene, cedrol, cerapictol, ceratopicanol, clovene, copaene, cubebene, eudalene, eudesmol, farnesene, farnesol, as well as their derivatives and analogs.

The present invention also contemplates compositions and formulations comprising agents, compounds, or drugs selected from the group consisting of germacrene, guaiazulene, guaiol, gurjunene, hexahydrohumulene, himachalene, hinesol, humulene, junipene, longifolene, lubiminol, khusimone, khusinol, khusimol, nootkatone, santalene, santalol, santanol, santonene, selinene, solavetivone, spatulenol, sterpurine, sulcatine, thujopsene, valerenol, vetispirene, vetivazulene, vetivene, vetiverol, vetivone, viridiflorine, and viridiflorol as well as their derivatives and analogs.

The sesquiterpenes of the present invention may also represent a lactone compound, a ketolactone compound, an alcohol compound a ketone compound, an aldehyde compound, an ester compound, an ether compound, or a carboxylic acid compound. The present invention covers compositions and formulations comprising agents, compounds and drugs of the present invention, their derivatives, analogs, and isomers. These derivatives, analogs, and isomers include, but are not limited to acetyl, acetate, phenylacetate, hydro, dihydro, formate, methyl ether, dimethylether, caprylate, valeriate, isovaleriate, alcohol, aldehyde, ketone, epoxide, lactone and cyclases derivatives.

The present invention covers compositions and formulations comprising agents, compounds and drugs of the present invention, their derivatives, analogs, and isomers. These derivatives, analogs, and isomers include, but are not limited to acetyl, acetate, phenylacetate, hydro, dihydro, formate, methyl ether, dimethylether, caprylate, valeriate, isovaleriate, alcohol, aldehyde, ketone, epoxide, lactone and cyclases derivatives.

In one embodiment, the analogs/derivatives of the present inventions are produced through addition of a mono-phenyl ring, addition of a heterocycle, addition of a substituted amide, addition of an unsubstituted amide, addition of a carbonyl imidazole, addition of a CN functional group, addition of a CONH2 functional group, addition of a CONHNH2 functional group, addition of a CO-D-Glu (OAc)4 functional group, and/or addition of a ketone to one of the following: an approved drug (e.g. one named or described herein), an OTC drug, a sesquiterpene, a sesquiterpenoid, a sesquiterpene lactone (e.g. lactucin, lactuopicrin, 8-deoxylactucin, picriside A, crepidiaside A, jacquinellin, jacquinellin glycoside, chamissonolide, helenalin, alantolactone, dehydrocostus lactone, costunolide), a id, an ATF4 modulator, a flavone, a flavonoid, quercetin, a shogaol (e.g. 6-shogaol), a gingerol (e.g. 6-gingerol), zingerol, kavalactone, sulforaphane, allyl-, butyl- and phenylethyl-isothiocyanate, chlorophyllin, alpha-lipoic acid, allicin, plumbagin, protandim, capsaicin, a capsaicinoid, piperine, asafetida, eugenol, piperlongumine, pellitorine, zingiberine, tBHQ, CDDO-Im, MC-LR, epigallocatechin-3-gallate, a compound found in wasabi, cafestol, xanthohumol, 5-O-caffeoylquinic acid, N-methylpyridinium, resveratrol, nootkatone, caffeic acid phenethyl ester, 3-O-Caffeoyl-1-methylquinic acid, silymarin, kahweol, garlic organosulfur compounds, lycopene, carnosol (rosemany), an avicin, oltipraz, CDDO, a neurite outgrowth promoting prostaglandin, vitamin D, a B vitamin, andrographolide, an amino acid, s-allylcysteine, Vitamin A, Vitamin C, Vitamin E, β carotene, trans-2-hexenal, cyclopentenone, ajoene, Dihydro-CDDO-trifluoroethyl amide, Hypochlorous acid, Fragrant unsaturated aldehydes (e.g. trans-cinnamaldehyde, safranal, 2,4-octadienal, citral, and trans-2,cis-6-nonadienal), 2-OHE, 4-OHE, bucillamine, acrolein, momordin, momordol, momordicin I, momordicin II, momordicosides, momordicin-28, momordicinin, momordicilin, momordenol, momorcharin, cucurbitacin B, charantin, charantosides, goyaglycosides, α-eleostearic acid, 15,16-dihydroxy-α-eleostearic acid, antirheumatic gold(I) compounds, an avicin, dithiolethione, an approved drug, an OTC drug, and/or a compound, agent or drug extracted from cloves, black pepper, red chili, cinnamon (e.g. cinnamic aldehyde), ginger, garlic, onion, fennel, bay leaves, nutmeg, saffron or coriander, In some embodiments, the analogs/derivatives of the present inventions are produced through conjugation of an amino acid, protein, glutathione, LHRH, bovine serum albumin (BSA) or non-protein to an approved drug, an OTC drug, a sesquiterpene, a sesquiterpenoid, zerumbone and/or other agent(s), compound(s), or drug(s) of the present invention, 8-hydroxy-alpha-humulene, glutathione, auraptene, ethacrynic acid, curcumin, a curcuminoid, hispolon, dehydroxyhispolon, methoxyhispolon, bisdemethylcurcumin, hispolon methyl ether, hydroxyhispolon, methoxyhispolon methyl ether, a triterpenoid, zingerone, reservatrol, vanillin, rosmarinic acid, a methoxyflavone, a sesquiperetene, n-acetylcysteine, trimethylglycine, folinic acid, folic acid, an amino acid, an ATF4 modulator, a flavone, a flavonoid, quercetin, a shogaol (e.g. 6-shogaol), a gingerol (e.g. 6-gingerol), zingerol, kavalactone, sulforaphane, allyl-, butyl- and phenylethyl-isothiocyanate, chlorophyllin, alpha-lipoic acid, allicin, plumbagin, protandim, capsaicin, a capsaicinoid, piperine, asafetida, eugenol, piperlongumine, pellitorine, zingiberine, tBHQ, CDDO-Im, MC-LR, epigallocatechin-3-gallate, a compound found in wasabi, cafestol, xanthohumol, 5-O-caffeoylquinic acid, N-methylpyridinium, resveratrol, nootkatone, caffeic acid phenethyl ester, 3-O-Caffeoyl-1-methylquinic acid, silymarin, kahweol, garlic organosulfur compounds, lycopene, carnosol (rosemany), an avicin, oltipraz, CDDO, a neurite outgrowth promoting prostaglandin, vitamin D, a B vitamin, andrographolide, an amino acid, s-allylcysteine, Vitamin A, Vitamin C, Vitamin E, β carotene, trans-2-hexenal, cyclopentenone, ajoene, Dihydro-CDDO-trifluoroethyl amide, Hypochlorous acid, Fragrant unsaturated aldehydes (e.g. trans-cinnamaldehyde, safranal, 2,4-octadienal, citral, and trans-2,cis-6-nonadienal), 2-OHE, 4-OHE, bucillamine, acrolein, antirheumatic gold(I) compounds, an avicin, dithiolethione, an approved drug, an OTC drug, and/or a compound, agent or drug extracted from cloves, black pepper, red chili, cinnamon (e.g. cinnamic aldehyde), ginger, garlic, onion, fennel, bay leaves, nutmeg, saffron or coriander.

In accordance with the present invention, any method of extraction or purification known to those skilled in the art may be used in obtaining the agent(s), compound(s) or drug(s) of the present invention, e.g. extraction using alcohol (including methanol, ethanol), or aqueous extraction using solvents such as ketones, esters, ethers, polyols, chlorinated solvents, and mixtures of two of the aforementioned solvents.

In some embodiments, the compositions and formulations (e.g. pharmaceutical, nutraceutical, cosmetic, dermatological, etc.) comprise two or more agents, compounds, or drugs of the present invention or their analogs, derivatives, and isomers.

In some embodiments, the compositions or formulations of the present invention comprise a methoxyflavone, a dimethoxyflavone, a trimethoxyflavone, or a tetramethoxyflavone.

In one embodiment, the compositions or formulations of the present invention comprise a derivative of a methoxyflavone, of a dimethoxflavone, of a trimethoxyflavone, or of a tetramethoxyflavone.

In one embodiment, the compositions or formulations of the present invention comprise a VEGF inhibitor.

The present invention further relates to a method of identifying agents, compounds or drugs useful in preventing or treating CDCP related diseases and conditions as well as other disorders diseases and conditions treatable or preventable by the same agents, compounds or drugs.

The method may comprise administering a candidate agent, compound, or drug to an animal or contacting cells in vitro or in vivo with a candidate agent, compound, or drug and assaying the activity of the VEGF promoter in response.

Various methods known to those skilled in the art for assaying promoter activity may be utilized including, RT-PCR, Western blot, and the use of recombinant reporter constructs such as those comprising luciferase or fluorescent protein operably linked to the VEGF promoter.

The VEGF promoter of the invention may be one deriving from multiple species, but is preferably a vertebrate promoter, and preferably a mammalian promoter, and preferably a human VEGF promoter.

Similarly, the activity or amounts of proteins regulated by VEGF may be assayed as another less direct means of assaying VEGF promoter activity. Suitable cells for conducting the assay(s) include those of mammals, e.g., laboratory animals, such as mice, rats, and other rodents as well as primates, etc. In one embodiment, the cell is a human cell.

Determining whether a compound reduces VEGF activity may include contacting the cell expressing VEGF with the agent, compound or drug. The term "contacting" refers to directly or indirectly bringing the cell and the compound together in physical proximity. The contacting may be performed in vitro or in vivo. For example, the cell may be contacted by delivering the agent, compound or drug to the cell through known techniques, such as microinjection, injecting the compound into the bloodstream of a mammal, and incubating the cell in a medium that includes the compound.

Also, determining whether an agent, compound, or drug reduces VEGF activity may further comprise measuring the level of VEGF activity in the cell. The level of VEGF may be measured by any method known in the art, including for example, immunohistochemistry, PCR analysis, RT-PCR, Northern blot, Western blot, ELISA assays, GFP reporter expression, luciferase reporter assays, etc. Accordingly, the level of VEGF activity may be assessed by measuring the level of induction of a reporter gene that is operably linked to the VEGF promoter or fused to the VEGF gene.

The level of VEGF activity may also be assessed by detecting the level of activity of a gene that is regulated by VEGF.

In some embodiments, cells that express VEGF in response to a known agent will be induced to express VEGF through exposure to that known agent and the level of VEGF activity measured in the cell in the presence of the candidate agent, compound or drug. Accordingly, the candidate's ability to reduce VEGF is measured in relation to the level of VEGF activity in the cell contacted with the known inducing agent.

In another aspect, the invention relates to a method for reducing VEGF activity in a cell in a human or animal in need thereof. The method includes administering to the human or animal an effective amount of an agent, compound or drug that inhibits VEGF activity (e.g. VEGF promoter activity) and that is named herein.

In a one embodiment, the compositions or formulations of the present invention comprise an agent, compound or drug that blocks VEGF promoter activation.

In a one embodiment, two or more agents are selected for use in combination from the list including a sequiterpene (e.g. zerumbone), glutathione, zingerone, curcumin or derivative, a flavone, flavonoid, a gingerol, a shogaol, an ATF4 modulator, a VEGF inhibitor, homocysteine, vitamin C, n-acetylcysteine, trimethylglycine, folinic acid, folic acid, reduced glutathione, an amino acid, an OTC drug, and an approved drug.

It has been taught that ATF4 activity is required to increase intracellular glutathione. While not bound by theory, the applicants believe, agents, compounds, or drugs increasing intracellular glutathione, while simultaneously inhibiting ATF4 are desirable for inclusion in the present invention, including those listed and described herein.

It is a proposition of this invention that it is desirable to provide a sequiterpene (e.g. zerumbone) and/or other FDA approved and/or non-FDA agent(s), compound(s), or drug(s) of the present invention in the context of a large number of diseases and conditions.

It is a further proposition of this invention that it is desirable to provide a sequiterpene (e.g. zerumbone) and/or other FDA approved and/or non-FDA agent(s), compound(s), or drug(s) of the present invention to prevent a large number of diseases and conditions.

In some embodiments, a sesquiterpene other than zerumbone is provided: a sesquiterpene lactone (e.g. lactucin, lactuopicrin, 8-deoxylactucin, picriside A, crepidiaside A, jacquinellin, jacquinellin glycoside, chamissonolide, helenalin, alantolactone, dehydrocostus lactone, costunolide), or a sesquiterpene lactone sulfate (Sessa et al., 2008), In one embodiment, the composition(s) or formulation(s) of the present invention comprises agents, compounds or drugs named herein and is and are used to prevent or treat cancer metastasis.

In one embodiment, the composition(s) or formulation(s) of the present invention comprises agents, compounds or drugs of the various classes named herein (e.g. zerumbone, zingerone, oltipraz, sulfuraphane, etc.), anti-EGFR agents (e.g. EGFR antibody, cetuximab and panitumumab), anti-VEGF agents (e.g. VEGF antibody), and/or another approved drug to prevent or treat cancer metastasis.

In one embodiment, the composition (s) or formulation(s) of the present invention comprises agents, compounds or drugs named herein (e.g. ones that are glutathione-conjugated, biotinylated, fluorinated, containing an NO moiety, etc.), anti-EGFR agents (e.g. EGFR antibody, cetuximab, necitumumab and panitumumab), anti-VEGF agents (e.g. VEGF antibody), and/or another approved drug (e.g. an NSAID) to prevent or treat cancer metastasis. In one embodiment, the composition (s) or formulation(s) of the present invention comprises two or more agents, compounds or drugs named herein (e.g. zingerone or zerumbone and/or other agent(s), compound(s), or drug(s) of the present invention) and is used to prevent or treat HIV infection.

In some embodiments, the present invention provides for formulations providing analgesia and pain relief in individuals in need of such treatment.

In some embodiments, the present invention provides means or adjunctive means of treating cancer (e.g. multiple myeloma, colorectal cancer, leukemic cells, Acute lymphoblastic leukemia, Acute myeloid leukemia, Adrenocortical carcinoma, AIDS-related cancers, AIDS-related lymphoma, Anal cancer, Appendix cancer, Astrocytoma, childhood cerebellar or cerebral, Basal cell carcinoma, Bile duct cancer, extrahepatic, Bladder cancer, Bone cancer, Osteosarcoma/Malignant fibrous histiocytoma, Brainstem glioma, Brain tumor, Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt lymphoma, Carcinoid tumor, childhood, Carcinoid tumor, gastrointestinal, Carcinoma of unknown primary, Central nervous system lymphoma, primary, Cerebellar astrocytoma, childhood, Cerebral astrocytoma/Malignant glioma, childhood, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Extracranial germ cell tumor, Childhood, Extragonadal Germ cell tumor, Extrahepatic bile duct cancer, Eye Cancer, Intraocular melanoma, Eye Cancer, Retinoblastoma, Gallbladder cancer, Gastric (Stomach) Cancer, Gastric (Stomach) Cancer, Childhood, Gastrointestinal Carcinoid Tumor, Gastrointestinal Stromal Tumor (GIST), Germ Cell Tumor, Extracranial, Childhood, Germ Cell Tumor, Extragonadal, Germ Cell Tumor, Ovarian, Gestational Trophoblastic Tumor, Glioma, Adult, Glioma, Childhood Brain Stem, Glioma, Childhood Cerebral Astrocytoma, Glioma, Childhood Visual Pathway and Hypothalamic, Gastric Carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, childhood, Intraocular Melanoma, Islet Cell Carcinoma (Endocrine Pancreas), Kaposi sarcoma, Kidney cancer (renal cell cancer), Laryngeal Cancer, Leukemias, Leukemia, acute lymphoblastic (also called acute lymphocytic leukemia), Leukemia, acute myeloid (also called acute myelogenous leukemia), Leukemia, chronic lymphocytic (also called chronic lymphocytic leukemia), Leukemia, chronic myelogenous (also called chronic myeloid leukemia), Leukemia, hairy cell, Lip and Oral Cavity Cancer, Liver Cancer (Primary), Lung Cancer, Non-Small Cell, Lung Cancer, Small Cell, Lymphomas, Lymphoma, AIDS-related, Lymphoma, Burkitt, Lymphoma, cutaneous T-Cell, Lymphoma, Hodgkin, Lymphomas, Non-Hodgkin (an old classification of all lymphomas except Hodgkin's), Lymphoma, Primary Central Nervous System, Macroglobulinemia, Waldenström, Malignant Fibrous Histiocytoma of Bone/Osteosarcoma, Medulloblastoma, Childhood, Melanoma, Melanoma, Intraocular (Eye), Merkel Cell Carcinoma, Mesothelioma, Adult Malignant, Mesothelioma, Childhood, Metastatic Squamous Neck Cancer with Occult Primary, Mouth Cancer, Multiple Endocrine Neoplasia Syndrome, Childhood, Multiple Myeloma/Plasma Cell Neoplasm, Mycosis Fungoides, Myelodysplastic Syndromes, Myelodysplastic/Myeloproliferative Diseases, Myelogenous Leukemia, Chronic, Myeloid Leukemia, Adult Acute, Myeloid Leukemia, Childhood Acute, Myeloma, Multiple (Cancer of the Bone-Marrow), Myeloproliferative Disorders, Chronic, Nasal cavity and paranasal sinus cancer, Nasopharyngeal carcinoma, Neuroblastoma, Non-Hodgkin lymphoma, Non-small cell lung cancer, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, pancreatic cancer, islet cell cancer, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, childhood, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter, transitional cell cancer, Retinoblastoma, Rhabdomyosarcoma, Salivary gland cancer, Sarcoma, Ewing family of tumors, Sarcoma, Kaposi, Sarcoma, soft tissue, Sarcoma, uterine, Sézary syndrome, Skin cancer (nonmelanoma), Skin cancer (melanoma), Skin carcinoma, Merkel cell, Small cell lung cancer, Small intestine cancer, Soft tissue sarcoma, Squamous cell carcinoma—see Skin cancer (nonmelanoma), Squamous neck cancer with occult primary, metastatic, Stomach cancer, Supratentorial primitive neuroectodermal tumor, childhood, T-Cell lymphoma, cutaneous—see Mycosis Fungoides and Sézary syndrome, Testicular cancer, Throat cancer, Thymoma, childhood, Thymoma and Thymic carcinoma, Thyroid cancer, Thyroid cancer, childhood, Transitional cell cancer of the renal pelvis and ureter, Trophoblastic tumor, Ureter and renal pelvis, transitional cell cancer, Urethral cancer, Uterine cancer, endometrial, Uterine sarcoma, Vaginal cancer, Visual pathway and hypothalamic glioma, childhood, Vulvar cancer, Waldenström macroglobulinemia, Wilms tumor (kidney cancer), childhood, etc.) and other cancers, in vitro or in vivo, comprising the steps of: contacting said cells with an amount of agent(s), compound(s) or drug(s) of the present invention delivered by a formulation effective to inhibit the proliferation of the cancer cells.

In some embodiments, the present invention provides the means of inducing apoptosis in cancer cells in vitro or in vivo, comprising the steps of: contacting said cells with an amount of an agent(s), compound(s) or drug(s) of the present invention delivered by a formulation effective to induce apoptosis in the cancer cells.

In some embodiments, the present invention provides the means of increasing the cytotoxic effects of one or more chemotherapeutic agents against the cancer cells, comprising the steps of: contacting said cells with said one or more chemotherapeutic agents and an agent(s), compound(s) or drug(s) of the present invention delivered by a formulation wherein said formulation of the present invention increases the cytotoxic effects of said one or more chemotherapeutic agent against the cancer cells.

In some embodiments, one or more chemotherapeutic agent is selected from the group consisting of vincristine, BCNU, melphalan, cyclophosphamide, Adriamycin, prednisone, velcade, thalidomide, and dexamethasone In some embodiments, said cancer cells are CD138+ plasma cells.

In some embodiments, the present invention provides the means of treating multiple myeloma or other cancer in an individual, comprising the step of administering a therapeutically effective amount of a formulation of the present invention to said individual.

In some embodiments, said formulation of the present invention is administered in a dose of from about 0.01 mg/kg of the individual's body weight to about 500 mg/kg of the individual's body weight.

In some embodiments, the present invention provides the means of increasing the cytotoxic effects of one or more chemotherapeutic agents against multiple myeloma or other cancer cells in an individual, comprising the steps of: administering to said individual said one or more chemotherapeutic agents and an agent, compound or drug of the present invention, wherein said formulation of the present invention increases the cytotoxic effects of said one or more chemotherapeutic agents against multiple myeloma cells in said individual.

In some embodiments, one or more chemotherapeutic agents is selected from the group consisting of vincristine, BCNU, melphalan, cyclophosphamide, Adriamycin, prednisone velcade, thalidomide, and dexamethasone or other approved chemotherapeutic listed herein.

A goal of the present invention is to provide compositions and formulations of a sesquiterpene (e.g. zerumbone) and/or other agent(s), compound(s), or drug(s) of the present invention suitable for use in individuals in all states of health.

In some embodiments, the dose of the sesquiterpene (e.g. zerumbone) and/or other agent(s), compound(s), or drug(s) of the present invention in such formulations varies from 0.5 mg/kg to 500 mg/kg.

In some embodiments, the dose of zerumbone and/or other agent(s), compound(s), or drug(s) of the present invention in such formulations varies from 5 mg/kg to 200 mg/kg. In some embodiments, said formulation or combination of the present invention is administered orally while in other embodiments, said formulation or combination of the present invention is administered parenterally, sublingually or topically, or by various routes simultaneously.

In one embodiment, the compositions and formulations of the present invention further comprise an approved drug—especially a drug for treating or preventing the same disease or condition, or similar disease or condition for which zerumbone and/or other agent(s), compound(s), or drug(s) of the present invention and/or other agent, compound, or drug of the present invention is being provided.

In some embodiments the approved drug is an FDA approved drug.

In some embodiments, the sesquiterpene (e.g. zerumbone), and/or other agent(s), compound(s), or drug(s) of the present invention and/or other agent, compound, or drug of the present invention is combined with an approved drug—especially a drug for treating or preventing the same disease or condition or similar condition for which zerumbone and/or other agent(s), compound(s), or drug(s) of the present invention is being provided. In some embodiments, the sesquiterpene (e.g. zerumbone) and/or other agent(s), compound(s), or drug(s) of the present invention and/or other agent, compound, or drug of the present invention is combined with an approved drug—including an approved drug for treating or preventing a different disease or condition than that for which zerumbone and/or other agent(s), compound(s), or drug(s) of the present invention and/or another agent, compound, or drug of the present invention is being provided.

In one embodiment, the approved drug provided with the sesquiterpene (e.g. zerumbone) and/or other agent(s), compound(s), or drug(s) of the present invention and/or other agent, compound, or drug of the present invention is an approved drug that produces a decrease in intracellular or extracellular glutathione concentration.

In one embodiment, the approved drug provided with the sesquiterpene (e.g. zerumbone) and/or other agent(s), compound(s), or drug(s) of the present invention and/or other agent, compound, or drug of the present invention is an approved drug that produces an increase in intracellular or extracellular glutathione concentration.

In addition to being used as a monotherapy, the therapeutic methods of the present invention will also find use in combination therapies.

In some embodiments, the compositions or formulations described herein comprise nationally approved agents, compounds or drugs listed herein and/or approved agents, compounds or drugs belonging to the drug classes represented by Abilify (aripiprazole), ABREVA (docosanol), Accolate, Accretropin (somatropin rDNA Original), Aciphex (rabeprazole sodium), Actemra (tocilizumab), Actiq, Activella (Estradiol/Norethindrone Acetate) Tablets, Actonel, ACTOplus met (pioglitazone hydrochloride and metformin hydrochloride), ACTOS, Acular (ketorolac tromethamine ophthalmic solution) 0.5%, Acular (ketorolac tromethamine ophthalmic solution) 0.5%, Acuvail (ketorolac tromethamine), Acyclovir Capsules, Adcirca (tadalafil), Adderall (mixed salts of a single-entity amphetamine), Adderall XR, Advicor (extended-release niacin/lovastatin), Afinitor (everolimus), Agenerase (amprenavir), Aggrenox, Agrylin (anagrelide HCL), Agrylin (anagrelide HCL), AK-Con-A (naphazoline ophthalmic), Akten (lidocaine hydrochloride), Alamast, Albenza (albendazole), Aldara (imiquimod), Aldurazyme (laronidase), Alesse (100 mcg levonorgestrel/20 mcg ethinyl estradiol tablets), Alimta (pemetrexed for injection), Alinia (nitazoxanide), Allegra (fexofenadine hydrochloride), Allegra-D, Alora, Aloxi (palonosetron), Alphagan (brimonidine), AlphaNine SD Coagulation Factor IX (Human), Alrex, Altabax (retapamulin), Altocor (lovastatin) Extended-Release Tablets, Alvesco (ciclesonide), Amaryl (Glimepiride), Amerge, Amevive (alefacept), Amitiza (lubiprostone), Amoxil (amoxicillin), Ampyra (dalfampridine), Amrix (cyclobenzaprine hydrochloride extended release), Androderm (Testosterone Transdermal System), AndroGel testosterone gel, AneuVysion Assay, Anexsia, Angiomax (bivalirudin), Antizol Injection, Anzemet, Anzemet, Aphthasol, Aplenzin (bupropion hydrobromide), Apokyn (apomorphine hydrochloride), Apthasol (Amlexanox), Aptivus (tipranavir), Aptivus (tipranavir), Arava, Aredia (pamidronate di sodium for injection), Arestin (minocycline hydrochloride), Argatroban Injection, ARICEPT (donepezil hydrochloride), Arimidex (anastrozole), Arixtra, Aromasin Tablets, Arranon (nelarabine), Arthrotec, Arzerra (ofatumumab), Asacol (mesalamine), Astelin nasal spray, Astepro (azelastine hydrochloride nasal spray), Atacand (candesartan cilexetil), Atacand (candesartan cilexetil), Atacand (candesartan cilexetil), Atracurium Besylate Injection, Atridox, Atridox, Atrovent (ipratropium bromide), Atryn (antithrombin recombinant lyophilized powder for reconstitution), Augmentin (amoxicillin/clavulanate), Avandamet (rosiglitazone maleate and metformin HCl), Avandia (rosiglitazone maleate), Avastin (bevacizumab), Avastin (bevacizumab), Avelox I.V. (moxifloxacin hydrochloride), Avinza (morphine sulfate), Avita Gel, Avita Gel, Avonex (Interferon Beta 1-A), Axert (almotriptan malate) tablets, Axid AR (nizatidine, Axona (caprylidene), AzaSite (azithromycin), Azmacort (triamcinolone acetoni de) Inhalation Aerosol, Azor (amlodipine besylate; olmesartan medoxomil), Azulfidine EN-tabs Tablets (sulfasalazine delayed release tablets, USP), Bactroban Cream, Bactroban Nasal 2% (mupirocin calcium ointment), Banzel (rufinamide), Baraclude (entecavir), Baycol (cerivastatin sodium), Bayer Extra Strength Asprin, BeneFIX (coagulation Factor IX (recombinant)), BeneFIX (coagulation Factor IX (recombinant)), Benicar, Benzamycin (erythromycin 3%-benzoyl peroxide 5% topical gel), Bepreve (bepotastine besilate ophthalmic solution), Berinert (C1 Esterase Inhibitor (Human)), Besivance (besifloxacin ophthalmic suspension), Betapace AF Tablet, Betaxon, Bextra, Bexxar, Biaxin XL (clarithromycin extended-release tablets), BiDil (isosorbide dinitrate/hydralazine hydrochloride), Boniva (ibandronate), Botox (onabotulinumtoxinA), Botox (onabotulinumtoxinA), Botox Cosmetic (botulinum toxin type A), Bravelle (urofollitropin for injection, purified), Breathe Right, Bromfenac, Brovana (arformoterol tartrate), BSS Sterile Irrigating Solution, Busulflex, Byetta (exenatide), Caduet (amlodipine/atorvastatin), Cafcit Injection, Cambia (diclofenac potassium for oral solution), Campath, Campostar, Campral (acamprosate calcium), Camptosar, Canasa (mesalamine), Cancidas, Captopril and hydrochlorotiazide, Captopril and hydrochlorotiazide, Carbaglu (carglumic acid), Carbatrol, Cardizem (R) (Diltiazem HCl for injection) Monvial (R), Carrington patch, Caverject (alprostadil), Cayston (aztreonam for inhalation solution), CEA-Scan, Cedax (ceftibuten), Cefazolin and Dextrose USP, Ceftin (cefuroxime axetil), Celexa, CellCept, Cenestin, Cenestin, Cernevit, Cervarix [Human Papillomavirus Bivalent (Types 16 and 18) Vaccine, Recombinant, Cetrotide, Chantix (varenicline), Children's Advil (pediatric ibuprofen), Children's Motrin Cold, Chloraprep (chlorhexidine gluconate), Cialis (tadalafil), Cimetadine Hydrochloride Oral Solution 300 mg/5 ml, Cimetidine Hydrochloride Oral Solution, Cimetidine Hydrochloride Oral Solution, Cimzia (certolizumab pegol), Cimzia (certolizumab pegol), Cinryze (C1 Inhibitor (Human)), Cipro (ciprofloxacin HCl), Cipro (ciprofloxacin HCl), Cipro (ciprofloxacin) I.V. and Cipro (ciprofloxacin HCl) tablets, Clarinex, Clarithromycin (Biaxin), Claritin RediTabs (10 mg loratadine rapidly-disintegrating tablet), Claritin Syrup (loratadine), Claritin-D 24 Hour Extended Release Tablets (10 mg loratadine, 240 mg, pseudoephedrine sulfate), Clemastine fumarate syrup, Cleocin (clindamycin phosphate), Cleocin (clindamycin phosphate), Cleviprex (clevidipine), Climara, Clindamycin phosphate topical gel, Clindamycin Phosphate Topical Solution USP 1%, Clolar (clofarabine), Clomipramine hydrochloride, Clonazepam, Coartem (artemether/lumefantrine), Colazal (balsalazide disodium), Colcrys (colchicine), Combivir, Comtan, Concerta, Condylox Gel 0.5% (pokofilox), Confide, Copaxone, Corlopam, Corvert Injection (ibutilide fumarate injection), Cosopt, Covera-HS (verapamil), Crestor (rosuvastatin calcium), Crinone 8% (progesterone gel), Crixivan (Indinavir sulfate), Curosurf, Cuvposa (glycopyrrolate), Cycloset, bromocriptine mesylate, Cylert, Cymbalta (duloxetine), Dacogen (decitabine), Daptacel, Degarelix (degarelix for injection), DentiPatch (lidocaine transoral delivery system), Depakote (divalproex sodium), Depakote (divalproex sodium), Depakote ER (divalproex sodium), Dermagraft-TC, Desmopressin Acetate (DDAVP), Desmopressin Acetate (DDAVP), Desonate (desonide), Detrol (tolterodine tartrate), Detrol LA (tolterodine tartrate), Differin (adapalene gel) Gel, 0.1%, Diltiazem HCL, Extended-Release Capsules, Diovan (valsartan), Diovan (valsartan), Diovan HCT (valsartan), Ditropan XL (oxybutynin chloride), Ditropan XL (oxybutynin chloride), Doribax (doripenem), Dostinex Tablets (cabergoline tablets), Doxil (doxorubicin HCl liposome injection), Droxia, Dulera (mometasone furoate+formoterol fumarate dihydrate), DuoNeb (albuterol sulfate and ipratropium bromide), Durezol (difluprednate), dutasteride, Dynabac, DynaCirc CR, EDEX, Edluar (zolpidem tartrate), Effexor (venlafaxin HCL), Effexor XR (venlafaxin HCl), Efient (prasugrel), Egrifta (tesamorelin for injection), Elaprase (idursulfase), Elestrin (estradiol gel), Elidel, Eligard (leuprolide acetate), Elitek (rasburicase), ella (ulipristal acetate), Ellence, Elliotts B Solution (buffered intrathecal electrolyte/dextrose injection), Elmiron (pentosan polysulfate sodium), Eloxatin (oxaliplatin/5-fluorouracil/leucovorin), Embeda (morphine sulfate and naltrexone hydrochloride), Emend (aprepitant), Enbrel (etanercept), Entereg (alvimopan), Entocort EC (budesonide), Epivir (lamivudine), Epivir (lamivudine), Epogen, Eraxis (anidulafungin), Erbitux (cetuximab), Esclim, Estradiol tablets, Estradiol tablets, Estradiol Transdermal System, Estratab (0.3 mg), EstroGel (estradiol gel 0.06%), Estrostep (norethindrone acetate and ethinyl estradiol), Estrostep (norethindrone acetate and ethinyl estradiol), Estrostep (norethindrone acetate and ethinyl estradiol), Ethyol (amifostine), Ethyol (amifostine), Etodolac, Etodolac, Etodolac, Eulexin (flutamide), Evamist (estradiol), Evista (raloxifene hydrochloride), Evi sta (raloxifene hydrochloride), Evi sta (raloxifene hydrochloride), Evoxac, Exalgo (hydromorphone hydrochloride) extended release, Excedrin Migraine, Exelon (rivastigmine tartrate), Exelon (rivastigmine tartrate), Extavia (Interferon beta-1 b), Extina (ketoconazole), Fabrazyme (agalsidase beta), Famvir (famciclovir), Famvir (famciclovir), Fanapt (iloperidone), Faslodex (fulvestrant), Femara (letrozole), Femara (letrozole), Femhrt Tablets, FemPatch, Femstat 3 (butoconazole nitrate 2%), FEMSTAT One, Fenofibrate, Feraheme (ferumoxytol), Feridex I.V., Ferrlecit, Fertinex (urofollitropin for injection, purified), Finacea (azelaic acid) Gel, 15%, Finevin, Flagyl ER, FLOMAX, Flonase Nasal Spray, Flovent Rotadisk, Floxin otic, Floxin Tablets (ofloxacin tablets), FluMist (Influenza Virus Vaccine), Fluzone Preservative-free, Focalin (dexmethylphenidate HCl), Follistim (TM) (follitropin beta for injection), Folotyn (pralatrexate injection), Foradil Aerolizer (formoterol fumarate inhalation powder), Forteo (teriparatide), Fortovase, Fosamax (alendronate sodium), Fosrenol, lanthanum carbonate, Fragmin, Frova (frovatriptan succinate), Fusilev (levoleucovorin), Fuzeon (enfuvirtide), Galzin (zinc acetate), Gardasil (quadrivalent human papillomavirus (types 6, 11, 16, 18), recombinant vaccine), Gastrocrom Oral Concentrate (cromolyn sodium), GastroMARK, Gelnique (oxybutynin chloride), Gemzar (gemcitabine HCL), Gemzar (gemcitabine HCL), Generic Transdermal Nicotine Patch, Genotropin (somatropin) injection, Genotropin (somatropin) lyophilized powder, Geodon (ziprasidone mesylate), Geref (sermorelin acetate for injection), Gilenya (fingolimod), Gleevec (imatinib mesylate), Gleevec (imatinib mesylate), Gliadel Wafer (polifeprosan 20 with carmustine implant), Glipizide Tablets, Glucagon, Glucagon, Glyburide Tablets, Glyburide Tablets, Glyburide Tablets, Glyset (miglitol), Gonal-F (follitropin alfa for injection), Halaven (eribulin mesylate), Havrix, Hectorol (Doxercalciferol) Injection, Hepsera (adefovir dipivoxil), Herceptin, Herceptin (trastuzumab), Hiberix (*Haemophilus* b Conjugate Vaccine; Tetanus Toxoid Conjugate), Humalog (insulin lispro), Humatrope (somatropin [rDNA origin] for injection), Humira (adalimumab), Hycamtin (topotecan hydrochloride), Hycamtin (topotecan hydrochloride), Iamin, Ilaris (canakinumab), Imagent (perflexane lipid microspheres), Imitrex (sumatriptan) injection and tablets, Imitrex (sumatriptan) nasal spray, Increlex (mecasermin), INFANRIX (Diphtheria and Tetanus Toxoids and Acellular Pertussis, Vaccine Adsorbed), Infasurf, INFERGEN (interferon alfacon-1), Inform HER-2/neu breast cancer test, Innohep (tinzaparin sodium) injectable, Inspra (eplerenone tablets), Integrilin, Intelence (etravirine), Interstim Continence Control Therapy, Intron A (Interferon alfa-2b, recombinant), Intron A (interferon alfa-2b, recombinant), Intron A (interferon alfa-2b, recombinant), Intuniv (guanfacine extended-release), Invanz, Invega (paliperidone), Invirase (saquinavir), Iontocaine, Iressa (gefitinib), Isentress (raltegravir), Istodax (romidepsin), IvyBlock, Ixempra (ixabepilone), Ixiaro (Japanese Encephalitis Vaccine, Inactivated, Adsorbed), Jalyn (dutasteride+tamsulosin), Januvia(sitagliptin phosphate), Jevtana (cabazitaxel), Kadian, Kalbitor (ecallantide), Kaletra Capsules and Oral Solution, Kapvay (clonidine hydrochloride), Keppra, Ketek (telithromycin), Ketoprofen, Kineret, Klaron (sodium sulfacet amide lotion) Lotion, 10%, Kogenate FS (Antihemophilic Factor Recombinant), Krystexxa (pegloticase), Kuvan (sapropterin dihydrochloride), Kytril (granisetron) solution, Kytril (granisetron) tablets, Lamictal (lamotrigine) Chewable Dispersible Tablets, Lamictal Chewable Dispersible Tablets, Lamisil (terbinafine hydrochloride) Dermagel, 1%, Lamisil (terbinafine hydrochloride) Solution, 1%, Lamisil (terbinafine hydrochloride) Tablets, Lamisil Solution, 1%, Lantus (insulin glargine [rDNA origin] injection), Lantus (insulin glargine [rDNA origin] injection), Latuda (lurasidone), Lescol (fluvastatin sodium), Lescol (fluvastatin sodium) capsules, Rx, Lescol XL (fluvastatin sodium) tablet, extended release, Letairis (ambrisentan), Leukine (sargramostim), Leukine (sargramostim), Levaquin, Levitra (vardenafil), Levo-T (levothyroxine sodium), Levoxyl, Lexapro (escitalopram oxalate), Lexiva (fosamprenavir calcium), Lexxel (enalapril maleate-felodipine ER), Lidoderm Patch (lidocaine patch 5%), Lithobid (Lithium Carbonate), Livalo (pitavastatin), Lodine (etodolac), Lodine XL (etodolac), Lodine XL (etodolac), Lotemax, Lotrisone (clotrimazole/betamethasone diproprionate) lotion, Lotronex (alosetron HCL) Tablets, Lovenox (enoxaparin sodium) Injection, Lovenox (enoxaparin sodium) Injection, Lovenox (enoxaparin sodium) Injection, Lucentis (ranibizumab), Lumigan (bimatoprost ophthalmic solution), Lunesta (eszopiclone), Lupron Depot (leuprolide acetate for depot suspension), Lupron Depot (leuprolide acetate for depot suspension), Lupron Depot (leuprolide acetate for depot suspension), Lusedra (fospropofol disodium), Lustra, LUVOX (fluvoxamine maleate), Luxiq (betamethasone valerate) Foam, Lyrica (pregabalin), Lysteda (tranexamic acid), Macugen (pegaptanib), Malarone (atovaquone; proguanil hydrochloride) Tablet, Marplan Tablets, Mavik (trandolapril), Maxalt, Mentax (1% butenafine HCl cream), Mentax (1% butenafine HCl cream), Mentax (1% butenafine HCl cream), Menveo (meningitis vaccine), MERIDIA, Merrem I.V. (meropenem), Mesnex, Metadate CD, Metaglip (glipizide/metformin HCl), Metaprotereol Sulfate Inhalation Solution, 5%, Metozolv ODT (metoclopramide hydrochloride), MetroLotion, Mevacor (lovastatin) tablets, Miacalcin (calcitonin-salmon) Nasal Spray, Micardis (telmisartan), Micardis HCT (telmisartan and hydrochlorothiazide), Microzide (hydrochlorothiazide), Migranal, Minoxidil Topical Solution 2% for Women, Miraluma test, Mirapex, Mircera (methoxy polyethylene glycol-epoetin beta), Mircette, Mirena (levonorgestrel-releasing intrauterine system), Mobic (meloxicam) Tablets, Monistat 3 (miconazole nitrate), Monistat 3 (miconazole nitrate), Monurol, Moxatag (amoxicillin), Mozobil (plerixafor injection), Multaq (dronedarone), Muse, Mylotarg (gemtuzumab ozogamicin), Myobloc, Myozyme (alglucosidase alfa), Naglazyme (galsulfase), Naltrexone Hydrochloride Tablets, Namenda (memantine HCl), Naprelan (naproxen sodium), Nasacort AQ (triamcinolone acetonide) Nasal Spray, Nasacort AQ (triamcinolone acetonide) Nasal Spray, NasalCrom Nasal Spray, Nascobal Gel (Cyanocobalamin, USP), Nasonex Nasal Spray, Natazia (estradiol valerate+dienogest), Natrecor (nesiritide), Neulasta, Neumega, Neupogen, Neupro (rotigotine), Neurontin (gabapentin), Neurontin (gabapentin) oral solution, Neurontin (gabapentin) oral solution, Nexavar (sorafenib), Nexium (esomeprazole magnesium), Niaspan, NicoDerm CQ, Nicorette (nicotine polacrilex), Nicotrol nasal spray, Nicotrol transdermal patch, Nitrostat (nitroglycerin) Tablets, Nolvadex, NORCO tablets (Hydrocodone Bitartrate/Acetaminophen 10 mg/325 mg), Norditropin (somatropin (rDNA origin) for injection), Noritate, Normiflo, Norvir (ritonavir), Norvir (ritonavir), Novantrone (mitoxantrone hydrochloride), NovoLog (insulin aspart), Novolog Mix 70/30, Novothyrox (levothyroxine sodium), Noxafil (posaconazole), Nplate (romiplostim), Nuedexta (dextromethorphan hydrobromide and quinidine sulfate), Nutropin (somatropin-rDNA origin), Nutropin (somatropin-rDNA origin), NuvaRing, Nuvigil (armodafinil), Ocuflox (ofloxacin opthalmic solution) 0.3%, OcuHist, Oleptro (trazodone hydrochloride), Omnicef, Onglyza (saxagliptin), Onsolis (fentanyl buccal), Oral Cytovene, Oravig (miconazole), Orencia (abatacept), Orencia (abatacept), Orfadin (nitisinone), Ortho Evra, Ortho Tri-Cyclen Tablets (norgestimate/ethinyl estradiol), Ortho-Prefest, OsmoCyte Pillow Wound Dressing, Ovidrel (gonadotropin, chorionic human recombinant), Oxycodone and Aspirin, Oxycodone with Acetaminophen 5 mg/325 mg, OxyContin (oxycodone HCl controlled-release), Oxytrol (oxybutynin transdermal system), Ozurdex (dexamethasone), Pancreaze (pancrelipase), Panretin Gel, Patanase (olopatadine hydrochloride), Paxil (paroxetine hydrochloride), Paxil CR (paroxetine hydrochloride), Paxil CR (paroxetine hydrochloride), Pediarix Vaccine, Peg-Intron (peginterferon alfa-2b), Pegasys (peginterferon alfa-2a), Pennsaid (diclofenac sodium topical solution), Pentoxifylline, Pepcid Complete, Periostat (doxycycline hyclate), Periostat (doxycycline hyclate), PhosLo, Photodynamic Therapy, Photofrin, Pindolol, Plavix (clopidogrel bisulfate), Plavix (clopidogrel bisulfate), Plenaxis (abarelix for injectable suspension), Posicor, Pradaxa (dabigatran etexilate mesylate), Pramipexole, Prandin, Pravachol (pravastatin sodium), Pravachol (pravastatin sodium), Precose (acarbose), Premarin (conjugated estrogens), Prempro, Prempro & Premphase (conjugated estrogens/medroxyprogesterone acetate tablets), PREVACID(R) (lansopraxole), PREVEN; Emergency Contraceptive Kit, Prevnar 13 (Pneumococcal 13-valent Conjugate Vaccine), Prevpac, Prevpac, Prezista (darunavir), Priftin, Prilosec (omeprazole), Prilosec (omeprazole), Prilosec (omeprazole), Prilosec (omeprazole)Biaxin (clarithromycin) Combination Therapy, Prinivil or Zestril (Lisinopril), ProAmatine (midodrine), Procanbid (procainamide hydrochloride extended-release tablets), Prochloroperazine, Prochlorperazine, Prograf, Proleukin, Prolia (denosumab), Promacta (eltrombopag), Prometrium, Prometrium, Propecia, Proscar, Protonix (pantoprazole sodium) Delayed Release Tablets, Protonix (pantoprazole sodium) Delayed-Release Tablets, Protonix (pantoprazole sodium) Intravenous Formulation, Protopic (tacrolimus) ointment, Provenge (sipuleucel-T), Proventil HFA Inhalation Aerosol, Prozac Weekly (fluoxetine HCl), Pulmozyme (dornase alfa), Pulmozyme (dornase alfa), Quadramet (Samarium Sm 153 Lexidronam Injection), Quixin (levofloxacin), Qutenza (capsaicin), Qvar (beclomethasone dipropionate), Ranexa (ranolazine), Ranitidine Capsules, Ranitidine Tablets, Rapamune (sirolimus) oral solution, Rapamune (sirolimus) Tablets, Raplon, Raxar (grepafloxacin), Rebetol (ribavirin), REBETRON (TM) Combination Therapy, Rebif (interferon beta-1a), Reclast (zoledronic acid), Reclast (zoledronic acid), Redux (dexfenfluramine hydrochloride), Refludan, REGRANEX (becaplermin) Gel, Relenza, Relpax (eletriptan hydrobromide), Remeron (Mirtazapine), Remeron SolTab (mirtazapine), Remicade (infliximab), Remicade (infliximab), Reminyl (galantamine hydrobromide), Remodulin (treprostinil), Renagel (sevelamer hydrochloride), Renagel (sevelamer hydrochloride), RenaGelRenagel (sevelamer hydrochloride), Renova (tretinoin emollient cream), Renvela (sevelamer carbonate), ReoPro, REPRONEX(menotropins for injection, USP), Requip (ropinirole hydrochloride), Rescriptor Tablets (delavirdine mesylate tablets), Rescula (unoprostone isopropyl ophthalmic solution) 0.15%, RespiGam (Respiratory Syncitial Virus Immune Globulin Intravenous), Restasis (cyclosporine ophthalmic emulsion), Retavase (reteplase), Retin-A Micro (tretinoin gel) microsphere, 0.1%, Revlimid (lenalidomide), Reyataz (atazanavir sulfate), Rhinocort Aqua Nasal Spray, Rid Mousse, Rilutek (riluzole), Risperdal Oral Formulation, Ritalin LA (methylphenidate HCl), Rituxan, Rocephin, Rocephin, Rotarix (Rotavirus Vaccine, Live, Oral), Rotateq (rotavirus vaccine, live oral pentavalent), Rozerem (ramelteon), Rythmol, Sabril (vigabatrin), Saizen, Salagen Tablets, Samsca (tolvaptan), Sanctura (trospium chloride), Sancuso (granisetron), Saphris (asenapine), Savella (milnacipran hydrochloride), Sclerosol Intrapleural Aerosol, Seasonale, Lo Seasonale, Seasonique (ethinylestradiol+levonorgestrel), SecreFlo (secretin), Selegiline tablets, Self-examination breast pad, Selzentry (maraviroc), Sensipar (cinacalcet), Seprafilm, Serevent, Seroquel (R) (quetiapine fumarate) Tablets, Silenor (doxepin), Simponi (golimumab), Simulect, Singulair, Skelid (tiludronate disodium), Skin Exposure Reduction Paste Against Chemical Warfare Agents (SERPACWA), Soliris (eculizumab), Somatuline Depot (lanreotide acetate), Somavert (pegvisomant), Sonata, Spectracef, Spiriva HandiHaler (tiotropium bromide), SPORANOX (itraconazole), Sprix (ketorolac tromethamine), Sprycel (dasatinib), Stavzor (valproic acid delayed release), Stelara (ustekinumab), Strattera (atomoxetine HCl), Stromectol (ivermectin), Subutex/Suboxone (buprenorphine/naloxone), Sulfamylon, Supartz, Supprelin LA (histrelin acetate), Sustiva, Sutent (sunitinib), Symlin (pramlintide), Synagis, Synercid I.V., Synthroid (levothyroxine sodium), Synvisc, Synvisc-One (Hylan GF 20), Tamiflu capsule, Tarceva (erlotinib, OSI 774), Tasigna (nilotinib hydrochloride monohydrate), Tasmar, Tavist (clemastine fumarate), Tavist (clemastine fumarate), Taxol, Taxotere (Docetaxel), Tazorac topical gel, Teczem (enalapril maleate/diltiazem malate), Teflaro (ceftaroline fosamil), Tegretol (carbamazepine), Tegretol XR (carbamazepine), Tekamlo (aliskiren+amlodipine), Tekturna (aliskiren), Temodar, Tequin, Testim, Testoderm TTS CIII, Teveten (eprosartan mesylate plus hydrochlorothiazide), Teveten (eprosartan mesylate), Thalomid, Tiazac (diltiazem hydrochloride), Tiazac (diltiazem hydrochloride), Tiazac (diltiazem hydrochloride), Tikosyn Capsules, Tilade (nedocromil sodium), Tilade (nedocromil sodium), Tilade (nedocromil sodium), Timentin, Timentin, Tindamax, tinidazole, Tobi, Tolmetin Sodium, Topamax (topiramate), Topamax (topiramate), Toprol-XL (metoprolol succinate), Torisel (temsirolimus), Toviaz (fesoterodine fumarate), Tracleer (bosentan), Travatan (travoprost ophthalmic solution), Trazadone 150 mg, Treanda (bendamustine hydrochloride), Trelstar Depot (triptorelin pamoate), Trelstar LA (triptorelin pamoate), Tri-Nasal Spray (triamcinolone acetonide spray), Tribenzor (olmesartan medoxomil+amlodipine+hydrochlorothiazide), Tricor (fenofibrate), Tricor (fenofibrate), Trileptal (oxcarbazepine) Tablets, Trilipix (fenofibric acid), Tripedia (Diptheria and Tetanus Toxoids and Acellular Pertussis, Vaccine Absorbed), Trisenox (arsenic trioxide), Trivagizole 3 (clotrimazole) Vaginal Cream, Trivora-21 and Trivora-28, Trizivir (abacavir sulfate; lamivudine; zidovudine AZT) Tablet, Trovan, Twinrix, Tygacil (tigecycline), Tykerb (lapatinib), Tysabri (natalizumab), Tysabri (natalizumab), Tyvaso (treprostinil), Tyzeka (telbivudine), Uloric (febuxostat), Ultracet (acetaminophen and tramadol HCl), UltraJect, UroXatral (alfuzosin HCl extended-release tablets), Urso, UVADEX Sterile Solution, Valcyte (valganciclovir HCl), Valstar, Valtrex (valacyclovir HCl), Vancenase AQ 84 mcg Double Strength, Vanceril 84 mcg Double Strength (beclomethasone dipropionate, 84 mcg), Inhalation Aerosol, Vaprisol (conivaptan), Vectibix (panitumumab), Velcade (bortezomib), Veltin (clindamycin phosphate and tretinoin), Venofer (iron sucrose injection), Ventolin HFA (albuterol sulfate inhalation aerosol), Veramyst (fluticasone furoate), Verapamil, Verdeso (desonide), Veregen (kunecatechins), VERSED (midazolam HCl), Vesicare (solifenacin succinate), Vfend (voriconazole), Viadur (leuprolide acetate implant), Viagra, Vibativ (telavancin), Victoza (liraglutide), Vidaza (azacitidine), Videx (didanosine), Vimovo (naproxen+esomeprazole), Vimpat (lacosamide), Vioxx (rofecoxib), VIRACEPT (nelfinavir mesylate), Viramune (nevirapine), Viread (tenofovir disoproxil fumarate), Viread (tenofovir disoproxil fumarate), Viroptic, Visicol Tablet, Visipaque (iodixanol), Vistide (cidofovir), Vistide (cidofovir), Visudyne (verteporfin for injection), Vitrasert Implant, Vitravene Injection, Vivelle (estradiol transdermal system), Vivelle (estradiol transdermal system), Vivelle-Dot (estradiol transdermal system), Vivitrol (naltrexone for extended-release injectable suspension), Vivitrol (naltrexone for extended-release injectable suspension), Votrient (pazopanib), Vpriv (velaglucerase alfa for injection), Vyvanse (Lisdexamfetamine Dimesylate), Warfarin Sodium tablets, Welchol (colesevelam hydrochloride), Western blot confirmatory device, Wilate (von Willebrand Factor/Coagulation Factor VIII Complex (Human), Xeloda, Xeloda, Xenazine (tetrabenazine), Xenical/Orlistat Capsules, Xeomin (incobotulinumtoxinA), Xgeva (denosumab), Xiaflex (collagenase *clostridium histolyticum*), Xifaxan (rifaximin), Xifaxan (rifaximin), Xigris (drotrecogin alfa [activated]), Xolair (omalizumab), Xopenex, Xyrem (sodium oxybate), Xyzal (levocetirizine dihydrochloride), Yasmin (drospirenone/ethinyl estradiol), ZADITOR, Zagam (sparfloxacin) tablets, Zanaflex (tizanidine hydrochloride), Zantac 75 Efferdose, Zelnorm (tegaserod maleate) Tablets, Zelnorm (tegaserod maleate) Tablets, Zemaira (alphal-proteinase inhibitor), Zemplar, Zenapax, Zenpep (pancrelipase), Zerit (stavudine), Zerit (stavudine), Zevalin (ibritumomab tiuxetan), Ziprasidone (ziprasidone hydrochloride), Zipsor (diclofenac potassium), Zirgan (ganciclovir ophthalmic gel), Zithromax (azithromycin), Zocor, Zofran, Zofran, Zoladex (10.8 mg goserelin acetate implant), Zoloft (sertraline HCl), Zoloft (sertraline HCl), Zoloft (sertraline HCl), Zometa (zoledronic acid), Zometa (zoledronic acid), Zomig (zolmitriptan), Zomig (zolmitriptan), Zonegran (zonisamide) Capsules, Zortress (everolimus), Zosyn (sterile piperacillin sodium/tazobactam sodium), Zuplenz (ondansetron oral soluble film), Zyban Sustained-Release Tablets, Zyclara (imiquimod), Zyflo (Zileuton), Zymaxid (gatifloxacin ophthalmic solution), Zyprexa, and Zyrtec (cetirizine HCl). In such instances, the approved drug(s) may typically be provided at or about the same dosage as usually prescribed for a particular indication, although lower or higher dosages may be desirable depending upon the clinical picture.

In some embodiments, the formulations or drug combinations of the present invention comprise one or more erythropoietin-like agent selected from erythropoietin, Darbepoetin (Aranesp), Epocept (Lupin pharma), Epogen, Epogin, Eprex, Procrit, NeoRecormon, Recormon, Methoxy polyethylene glycol-epoetin beta (Mircera), Dynepo, Epomax, Silapo (Stada), Retacrit, Epocept, EPOTrust, Erypro Safe, Repoitin, Vintor, Epofit, Erykine, Wepox, Espogen, ReliPoietin, Shanpoietin, Zyrop, or EPIAO (rHuEPO).

In some embodiments, one or more agents, compounds and drugs of the present invention are selected from the list comprising zerumbone, a sesquiterpene, a sesquiterpenoid, a sesquiterpene lactone (e.g. lactucin, lactuopicrin, 8-deoxylactucin, picriside A, crepidiaside A, jacquinellin, jacquinellin glycoside, chamissonolide, helenalin, alantolactone, dehydrocostus lactone, costunolide), a sesquiterpene sulfate, reduced glutathione, auraptene, ethacrynic acid, curcumin, a curcuminoid, hispolon, dehydroxyhispolon, methoxyhispolon, bisdemethylcurcumin, hispolon methyl ether, hydroxyhispolon, methoxyhispolon methyl ether, a triterpenoid (e.g. Betulinic acid), zingerone, reservatrol, vanillin, rosmarinic acid, a methoxyflavone, a sesquiperetene, n-acetylcysteine, trimethylglycine, folinic acid, folic acid, an amino acid, an ATF4 modulator, flavone, a flavonoid, quercetin, a shogaol (e.g. 6-shogaol), a gingerol (e.g. 6-gingerol), zingerol, kavalactone, sulforaphane, allyl-, butyl- and phenylethyl-isothiocyanate, chlorophyllin, alpha-lipoic acid, allicin, plumbagin, protandim, capsaicin, a capsaicinoid, piperine, asafetida, eugenol, piperlongumine, pellitorine, zingiberine, tBHQ, CDDO-Im, MC-LR, epigallocatechin-3-gallate, a compound found in wasabi, cafestol, xanthohumol, 5-O-caffeoylquinic acid, N-methylpyridinium, resveratrol, nootkatone, caffeic acid phenethyl ester, 3-O-Caffeoyl-1-methylquinic acid, silymarin, kahweol, garlic organosulfur compounds, lycopene, carnosol (rosemany), an avicin, oltipraz, CDDO, a neurite outgrowth promoting prostaglandin, vitamin D, a B vitamin, andrographolide, an amino acid, s-allylcysteine, Vitamin A, Vitamin C, Vitamin E, β carotene, trans-2-hexenal, cyclopentenone, ajoene, Dihydro-CDDO-trifluoroethyl amide, Hypochlorous acid, Fragrant unsaturated aldehydes (e.g. trans-cinnamaldehyde, safranal, 2,4-octadienal, citral, and trans-2,cis-6-nonadienal), 2-OHE, 4-OHE, bucillamine, acrolein, momordin, momordol, momordicin I, momordicin II, momordicosides, momordicin-28, momordicinin, momordicilin, momordenol, momorcharin, cucurbitacin B, charantin, charantosides, goyaglycosides, α-eleostearic acid, 15,16-dihydroxy-α-eleostearic acid, antirheumatic gold(I) compounds, an avicin, dithiolethione, an approved drug, and/or a compound, agent or drug extracted from cloves, black pepper, red chili, ginger, garlic, onion, fennel, bay leaves, nutmeg, saffron coriander and cinnamon (e.g. cinnamic aldehyde) is combined with one or more approved drugs of the drug classes exemplified herein or listed above. In such instances, an accompanying approved agent(s), compound(s) or drug(s) may typically be provided at or about the same dosage as usually prescribed for a particular indication, although lower or higher dosages may be desirable depending upon the clinical picture.

Typically, the resulting novel combination will be useful in preventing or treating a condition, disease or disorder for which the approved drug is considered to be approved for use.

The agents, compounds, and drugs of the present invention (including their analogs and derivatives) may be administered before or after the other agent in intervals ranging from seconds to weeks. In embodiments where the other approved therapy and the agents, compounds, and drugs of the present invention are applied separately to the cell, one would generally ensure that a sufficient amount of time did not pass such that the agent and the agents, compounds, and drugs of the present invention would still be able to exert an advantageous, combined effect.

Approved therapies include drug therapies, immunotherapy, gene therapy, radiotherapy, chemotherapy, surgery, etc.

With respect to the approved drugs provided within compositions and formulations of the present invention, the amount that will be effective in the treatment of a particular disorder or condition disclosed herein will depend on the nature of the disorder or condition, and can be determined by clinical techniques and in vitro or in vivo assays.

The precise dose of a drug to be employed will also depend on the route of administration, and should be decided according to the judgment of the practitioner and each patient's circumstances. However, suitable dosage ranges for oral administration are generally about 0.001 mg to about 1000 mg of an approved drug of the invention, or a pharmaceutically acceptable salt or complex thereof, per kg body weight/day. A bioequivalent amount of the approved drug will typically be provided by routes other than the oral route, is such a route of delivery is selected.

Examples of acceptable salts useful in the invention include, but are not limited salts formed with inorganic acids (e.g. those selected from the group consisting of hydrochloric, hydrobromic, sulfuric, phosphoric, nitric or equivalent), or salts formed with acids or organic acids (e.g. acetic, oxalic, tartaric, succinic, malic, fumaric, aleic, ascorbic, benzoic acid, tannic, alginic, polyglutamic, naphthalene sulfonic acid, naphthalene disulfonic acid and polygalacturonic).

In specific some embodiments, the oral dose of an approved drug is about 0.01 mg to about 100 mg/kg body weight/day, and more preferably about 0.1 mg to about 75 mg/kg body weight/day, and more preferably about 0.5 mg to 5 mg/kg body weight/day.

In some embodiments, combining a sesquiterpene (e.g. zerumbone) and/or other agent(s), compound(s), or drug(s) of the present invention or other agent, compound, or drug of the present invention with an approved drug will allow the skilled clinician to reduce the amount of an approved drug required to achieve clinical benefits, while simultaneously reducing the risk or severity of side effects associated with the treatment or prevention protocol.

In some embodiments, combining a sesquiterpene (e.g. zerumbone) and/or other named agent(s), compound(s), or drug(s) of the present invention with an approved drug will allow the skilled clinician to increase the amount of an approved drug provided to a patient to achieve greater benefit from that approved drug, while simultaneously reducing the risk or severity of side effects associated with the treatment or prevention protocol.

In one embodiment, the a sesquiterpene (e.g. zerumbone) and/or other named agent(s), compound(s), or drug(s) of the present invention and or reduced glutathione is incorporated into the approved drug's formulation along with the approved drug without otherwise altering the approved drug's formulation.

In one embodiment, a sesquiterpene (e.g. zerumbone) and/or other agent(s), compound(s), or drug(s) of the present invention and or reduced glutathione is incorporated into the approved drug's formulation along with the approved drug while adjusting the concentration of one or more of the formulation's active drug, stabilizer, buffer, vehicle, excipient, etc.

In further embodiments, the compositions and formulations comprising a sesquiterpene (e.g. zerumbone) and/or other agent(s), compound(s), or drug(s) of the present invention and an approved drug further comprise reduced glutathione.

In further embodiments, the compositions and formulations comprising a sesquiterpene (e.g. zerumbone) and/or other agent(s), compound(s), or drug(s) of the present invention and an approved drug further comprise a vitamin D.

In further embodiments, the compositions and formulations comprising a sesquiterpene (e.g. zerumbone) and/or other agent(s), compound(s), or drug(s) of the present invention and an approved drug further comprise a B vitamin.

In one embodiment, a compound or a drug of the classes exemplified herein, are combined with glutathione or an antioxidant in a nanoemulsion, nanoparticles (e.g. WO/2010/013224), nanovault, nanofiber, or other nanostructure.

In one embodiment, a sesquiterpene (e.g. zerumbone) and/or other agent(s), compound(s), or drug(s) of the present invention is provided at a dosage suitable to achieve a plasma concentration of between 1 and 1000 uM.

In a further preferred embodiment, a sesquiterpene (e.g. zerumbone) and/or other agent(s), compound(s), or drug(s) of the present invention is provided at a dosage suitable to achieve a plasma concentration of between 5 and 500 uM.

In a further preferred embodiment, a sesquiterpene (e.g. zerumbone) and/or other agent(s), compound(s), or drug(s) of the present invention is provided at a dosage suitable to achieve a plasma concentration of between 15 and 100 uM.

In one embodiment, a sesquiterpene (e.g. zerumbone) and/or other agent(s), compound(s), or drug(s) of the present invention is provided in 250 mg, 500 mg, or 1000 mg doses at a frequency suitable to maintain a desirable plasma concentration.

In some embodiments, the ratio of the sesquiterpene (e.g. zerumbone) and/or other agent(s), compound(s), or drug(s) of the present invention to other active compounds or agents in the compositions or formulations ranges from 1:50 to 50:1 based upon dry weight.

Further, in some embodiments, the ratio of a sesquiterpene (e.g. zerumbone) and other agent(s), compound(s), or drug(s) of the present invention to other active compounds or agents in the compositions or formulations ranges from 1:10 to 10:1.

In one embodiment, the ratio of a sesquiterpene (e.g. zerumbone) and other agent(s), compound(s), or drug(s) of the present invention to glutathione is 1:1.

In one embodiment, the ratio of a sesquiterpene (e.g. zerumbone) and other agent(s), compound(s), or drug(s) of the present invention to glutathione is 1:4 to 1:10.

In one embodiment, the compositions or formulations of the present invention comprise a sesquiterpene (e.g. zerumbone) and/or other agent(s), compound(s), or drug(s) of the present invention, selected from a methoxyflavone (especially a dimethoxyflavone), n-acetylcysteine, glutathione, a glutathione precursor, or a known intracellular glutathione promoting agent, folic acid, trimethylglycine, vitamin D, and medicinal iron.

In one embodiment, the compositions or formulations of the present invention comprise a sesquiterpene (e.g. zerumbone) and/or other agent(s), compound(s), or drug(s) of the present invention selected from a methoxyflavone, n-acetylcysteine, glutathione, a glutathione precursor, a glutathione enhancing agent, folinic acid, folic acid, trimethylglycine, and medicinal iron.

In one embodiment, daily doses of the compounds do not exceed 20 mg iron, 400 mcg of folic acid, 1600 mcg of folinic acid, 2000 mg of trimethylglycine, 3000 mg N-acetylcysteine, and the roughly bioequivalent dose of reduced glutathione, a glutathione precursor, or a known intracellular-glutathione promoting agent.

In one embodiment, the compound(s) or drug(s) of the present invention are administered with ascorbic acid.

In one embodiment, the compositions or formulations of the present invention 34 comprise 5,7 dimethoxyflavone and/or 6,3-dimethoxyflavone.

In one embodiment, the compositions or formulations of the present invention comprise compounds, agents or drugs extracted from ginger, cinnamon, black pepper, or cloves using ethanol or methanol extraction techniques.

In one embodiment, the compositions or formulations of the present invention comprise zingerone, a shogaol, and/or a gingerol.

In one embodiment, the compositions or formulations of the present invention comprise a compound, agent, or drug extracted from ginger, curcumin, a methoxyflavone, vitamin C, n-acetylcysteine, trimethylglycine, folinic acid, folic acid and/or reduced glutathione.

In one embodiment, the compositions or formulations of the present invention comprise an amino acid other than phenylalanine.

In one embodiment, the compositions or formulations of the present invention comprise a compound, agent or drug extracted from cloves, black pepper, red chili, cinnamon, and ginger.

In one embodiment, the compositions or formulations of the present invention comprise agent, compounds, or drugs selected from curcumin, zingerone, a methoxyflavone, vitamin C, n-acetylcysteine, trimethylglycine, folinic acid, folic acid, an amino acid and/or reduced glutathione.

In one embodiment, the compositions or formulations of the present invention comprise agent, compounds, or drugs selected from kavalactone, sulforaphane an isoselenocyanate compound of sulforaphane, alpha-lipoic acid, and/or allicin.

In one embodiment, the compositions or formulations of the present invention comprise an analog of a compound, agent, or drug named herein.

In some embodiments, reduced glutathione is added to any of the compositions and formulations described herein In some embodiments, reduced glutathione (in doses ranging from about 200 mg tp 2000 mg) is added to any of the compositions and formulations described herein.

In some embodiments, a D vitamin or a B vitamin is added to any of the compositions and formulations described herein.

In one embodiment, an ATF4 modulator (see Roybal et al. 2005 and WO/2009/020601) is added to any of the compositions and formulations described herein.

In one embodiment, the compositions and formulations comprise an ATF4 modulator.

In one embodiment, the compositions or formulations of the present invention comprise two or more compounds and agents selected from agents, compounds and drugs of the present invention (e.g. zerumbone, a sesquiterpene, a sesquiterpenoid, a sesquiterpene lactone (e.g. lactucin, lactuopicrin, 8-deoxylactucin, picriside A, crepidiaside A, jacquinellin, jacquinellin glycoside, chamissonolide, helenalin, alantolactone, dehydrocostus lactone, costunolide), a sesquiterpene sulfate, reduced glutathione, auraptene, ethacrynic acid, curcumin, a curcuminoid, hispolon, dehydroxyhispolon, methoxyhispolon, bisdemethylcurcumin, hispolon methyl ether, hydroxyhispolon, methoxyhispolon methyl ether, a triterpenoid (e.g. Betulinic acid), zingerone, reservatrol, vanillin, rosmarinic acid, a methoxyflavone, a sesquiperetene, n-acetylcysteine, trimethylglycine, folinic acid, folic acid, an amino acid, an ATF4 modulator, flavone, a flavonoid, quercetin, a shogaol (e.g. 6-shogaol), a gingerol (e.g. 6-gingerol), zingerol, kavalactone, sulforaphane, allyl-, butyl- and phenylethyl-isothiocyanate, chlorophyllin, alpha-lipoic acid, allicin, plumbagin, protandim, capsaicin, a capsaicinoid, piperine, asafetida, eugenol, piperlongumine, pellitorine, zingiberine, tBHQ, CDDO-Im, MC-LR, epigallocatechin-3-gallate, a compound found in wasabi, cafestol, xanthohumol, 5-O-caffeoylquinic acid, N-methyl-pyridinium, resevratrol, caffeic acid phenethyl ester, 3-O-Caffeoyl-1-methylquinic acid, silymarin, kahweol, garlic organosulfur compounds, lycopene, carnosol (rosemany), an avicin, oltipraz, CDDO, a neurite outgrowth promoting prostaglandin, vitamin D, a B vitamin, andrographolide, an amino acid, s-allylcysteine, Vitamin A, Vitamin C, Vitamin E, β carotene, trans-2-hexenal, cyclopentenone, ajoene, Dihydro-CDDO-trifluoroethyl amide, Hypochlorous acid, Fragrant unsaturated aldehydes (e.g. trans-cinnamaldehyde, safranal, 2,4-octadienal, citral, and trans-2,cis-6-nonadienal), 2-OHE, 4-OHE, bucillamine, acrolein, momordin, momordol, momordicin I, momordicin II, momordicosides, momordicin-28, momordicinin, momordicilin, momordenol, momorcharin, cucurbitacin B, charantin, charantosides, goyaglycosides, α-eleostearic acid, 15,16-dihydroxy-α-eleostearic acid, antirheumatic gold(I) compounds, an avicin, dithiolethione, an approved drug, and/or a compound, agent or drug extracted from bitter gourd, cloves, black pepper, red chili, ginger, garlic, onion, fennel, bay leaves, nutmeg, saffron coriander and cinnamon (e.g. cinnamic aldehyde).

In one embodiment, the compounds, agent, or drugs selected for inclusion in the compounds and formulations of the present invention are provided in doses of appropriate to achieve a plasma concentration of between 2 and 10 uM (xanthohumol, lycopene), of between 10 and 150 uM (zerumbone, a sesquiterpene, a sesquiterpenoid, a sesquiterpene lactone (e.g. lactucin, lactuopicrin, 8-deoxylactucin, picriside A, crepidiaside A, jacquinellin, jacquinellin glycoside, chamissonolide, helenalin, alantolactone, dehydrocostus lactone, costunolide), a sesquiterpene sulfate, sulforaphane, curcumin, ethacrynic acid, epigallocatechin-3-gallate, resveratrol, nootkatone, piperine, cafestol, carnosol, cinnamaldehyde, quercetin, chalcone, chlorophyllin), and of between 100 and 200 uM (sulforaphane, s-allylcysteine, piperine, capsaicin, carnosol, cinnamaldehyde, and 3-O-Caffeoyl-1-methylquinic acid).

In one embodiment, the compound(s), agent(s), or drug(s) selected for inclusion in the compounds and formulations of the present invention are provided as conjugates (amino acid/protein conjugates, LHRH conjugates, bovine serum albumin (BSA)-conjugate, and non-protein conjugates) derived according to methods known to the art (e.g. WO/2010/033580; WO/2010/057503; WO/2010/013224; WO2007098504; Ploemen, et al., 1993; 1994; Awashti et al., 2000; Lo et al., 2007; Pinnen et al., 2007; Ehrlich et al., 2007; More and Vince, 2008; 2010; Cacciatore et al., 2010).

In some other embodiments, the zerumbone and/or other agent(s), compound(s), or drug(s) of the present invention (or other agent, compound, or drug of the present invention) is coupled or conjugated to glutathione according methods effective to produce such coupling or conjugation (e.g. WO2007098504).

In one embodiment, compositions or formulations comprising zerumbone and/or other agent(s), compound(s), or drug(s) of the present invention further comprise zingerone.

In some embodiments, zerumbone and/or other agent(s), compound(s), or drug(s) of the present invention is replaced by a sesquiterpene, a sesquiterpenoid, a sesquiterpene lactone (e.g. lactucin, lactuopicrin, 8-deoxylactucin, picriside A, crepidiaside A, jacquinellin, jacquinellin glycoside, chamissonolide, helenalin, alantolactone, dehydrocostus lactone, costunolide), a sesquiterpene sulfate, and/or their analogs and derivatives in compositions and formulations of the present invention.

In one embodiment, compositions or formulations comprising zerumbone and/or other agent(s), compound(s), or drug(s) of the present invention further comprise zingerone at doses of between 100 to 600 mg/kg.

In some embodiments, the agents, compounds and drugs of the present invention are biotinylated (e.g. U.S. Pat. Nos. 4,794,082; 5,521,319).

In some embodiments, the compositions or formulations of the present invention provide zerumbone and/or other agent(s), compound(s), or drug(s) of the present invention in combination with one or more of any of the agents, compounds, or drugs named herein.

In further embodiments, formulation(s) or combination(s) described herein is altered so as to not comprise a sesquiterpene (e.g. zerumbone), but is otherwise unchanged.

In further embodiments, the sesquiterpene(s) vernodalin, vernodalinol, vernolide-A, vernomygdin, alantolactone, dehydrocostus lactone, costunolide, arnifolin, chamissonolide, 2-deacetyl-4-tigloylchamissonolide, 1-O-β-D-glucopyranosyl-9β,15-dihydroxy-5α,6βH-eudesma-3-ene-6α,12-olide, Dehydrocostuslactone, 1α,10β-epoxy-4-hydroxyglechoma-5-en-olide, 1β,10α-epoxy-4,8-dihydroxyglechoma-5-en-olide, and 1β,10α;4α,5β-diepoxy-8-methoxy-glechoman-8α,12-olide, tagitinin C, artemisinin, dehydrocostus lactone, santamarine, beta-cyclocostunolide, 4alpha-hydroxy-4beta-methyldihydrocostol, and 10 alpha-hydroxyl-artemisinic acid, chlorajapolides A-E, chlorajaposide, chlorajaponol, chloraeudolide 8, pseudoguaian-1α(H)-8α,12-olide-4β-O-β-d-glucopyranoside, 4β,10α-dihydroxy-5α(H)-1,11(13)-guaidien-8α,12-olide, 4β,10β-dihydroxy-5α(H)-1,11(13)-guaidien-8β,12-olide, and (4S)-acetyloxyl-11(13)-carabren-8β,12-olide, neojaponicone A, japonicones M-P, kachiraterpenol, (E)-2,3-bis(4-hydroxy-3-methoxyphenyl)prop-2-enal, kachiranol, tanachin, tavulin, parthenolide, 2α, 5-epoxy-5,10-dihydroxy-6-angeloyl-oxy-9β-isobutyloxy-germacran-8α,12-olide, 2α,5-epoxy-5,10-dihydroxy-6α,9β-diangeloyloxy-germacran-8α,12-olide, 2α,5-epoxy-5,10-dihydroxy-6α-angeloyloxy-9β-(3-methylbutanoyloxy)-gemacran-8α,12-olide, 2β,5-epoxy-5,10-dihydroxy-6α,9β-diangeloyloxy-germacran-8α,12-olide, atlantolactone, isoatlantolactone, ixerin N 6'-O-acetate, ixerisoside A 6'-O-acetate, ixerin N, 3β-hydroxy-11α,13-dihydroalantolactone, and 11α-hydroxy-eudesm-5-en-8β, 12-olide, deoxynivalenol (DON), zearalenone (ZEA), aromaticine, achillin, millefin, achillicin, trilobolide, and/or helenalin.

In some embodiments, the sesquiterpene lactone(s) of the present invention is a pseudoguaianolide, a xanthanolide, an eudesmanolide, a germacranolide, an elemanolides, an ambrosanolide, a seco-ambrosanolide, a seco-eudesmanolide, a helenanolide, a eremophilanolide, a bakkenolide, an elemanolide, a cadinanolide, a chrymoranolide, a guaianolides and/or a pseudogual inolide.

Additional chemical definitions, chemical structures, and formulae for compounds and compound classes useful in the present invention, as well as exemplary formulations, are further described in patent applications WO/2005/065667 as well other the other patent applications and articles referenced herein. They are all incorporated herein in their entirety.

In some embodiments, the non-approved agent(s), compound(s) or drug(s) modulate enzymes in the NRF2 pathway.

Testing

The present invention calls for the administration of an agent, compound, or drug to a human in an amount effective for achieving its benefit. Typical daily doses of compounds comprising the formulation vary approximately in the range of 0.5 mg to 5000 mg. The effective amount of the compound to be administered can be readily determined by those skilled in the art, for example, through pre-clinical trials, clinical trials, and by methods known to scientists, physicians and clinicians.

The present invention covers in vivo methods for the administration of a compound, agent or drug to an animal. These methods may vary and are not limited to those described herein. Within the pre-clinical and clinical period, any method known to the art may be employed for contacting a cell, organ or tissue with an agent, compound, or drug. Suitable methods include in vitro, ex vivo, or in vivo methods. In vitro methods include cultured samples. For example, a cell can be placed in medium and incubated with a compound, agent or drug under conditions suitable for assaying its activity (especially zerumbone and/or other agent(s), compound(s), or drug(s) of the present invention-like activity). Appropriate incubation conditions may be readily determined by those skilled in the art.

An effective amount of a compound, agent or drug useful in the methods of the present invention, may be administered to an animal by known methods. The compound may be administered systemically or locally.

Administration

With respect to the present invention, an agent, compound, or drug may, for example, be administered orally, parenterally (e.g. intravenously, intramuscularly, subcutaneously), intranasally, topically (e.g. WO/2009/153373; WO/2010/070675; WO2007126915), or transdermally (e.g. Cevc and Blume, 2001). Topical formulations include, for example, emulsions, gels, and sunscreens (e.g. WO2010129213; WO2007001484; WO2006099687). The CTFA Cosmetic Ingredient Handbook, Seventh Edition, 1997 and the Eighth Edition, 2000 (both incorporated by reference herein in their entirety) describe a wide variety of cosmetic and pharmaceutical ingredients suitable for use in the compositions of the present invention. Examples of these functional classes disclosed in this reference include: absorbents, skin protectants, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, SPF boosters, reducing agents, skin bleaching agents, skin-conditioning agents (emollient, humectants, miscellaneous, and occlusive), solvents, foam boosters, hydrotropes, solubilizing agents, suspending agents (nonsurfactant), sunscreen agents, ultraviolet light absorbers, waterproofing agents, and viscosity increasing agents (WO2010129213).

Other routes of administration include rectal administration, intrathecal administration, administration involving mucosal absorption, and administration in aerosolized form (e.g. U.S. Pat. Nos. 5,126,123; 5,544,646).

The present invention covers the administration of compositions or formulations useful in the methods of the invention to an animal by sustained release. Such administration is selected when it is considered beneficial to achieve a certain level of the drug in a body compartment over a longer period of time (e.g. serum or plasma concentration).

In some embodiments, the compositions and formulations of the present invention are suitable for oral administration including extended release formulations (e.g. Pouton, 2000; Prasad et al., 2003; WO/2010/137027; WO/2020/129337; WO/2010/127100; WO/2010/127191; WO/2010/119300; WO/2010/114801; WO/2010/103544). and controlled release formulations (WO 02/083106; U.S. Pat. Nos. 5,567,439; 6,838,094; 6,863,902; 6,905,708).

The present invention includes any formulation known to the art that is suitable for administration of the agents, drugs, and compositions useful in the methods of the present invention. Examples include tablets (U.S. Pat. No. 4,209,513), capsules (e.g. US 2010/0021535; U.S. Pat. No. 7,011,846), such as gelatin capsules (e.g. U.S. Pat. No. 5,698,155), pills, troches (e.g. U.S. Pat. No. 3,312,594), elixirs, suspensions, syrups (e.g. U.S. Pat. No. 6,790,837), wafers (e.g. Wen and Park, 2010), chewing gum (e.g. Chaudhary and Shahiwala, 2010; Semwal et al. 2010); U.S. Pat. No. 6,531,114; Surana et al, 2010), etc.

The present compositions and formulations therefore, can take the form of solutions, liquids (e.g. WO2010106191), gels (e.g. WO2007126915), suspensions, emulsion, tablets, pills, pellets, capsules, capsules containing liquids (e.g. WO2010106191), powders (US20040162273), sustained-release formulations, suppositories, emulsions, aerosols, sprays (e.g. WO/2010/109482), drops, suspensions, nanoemulsions (e.g. WO2010070675), sublingual compositions (e.g. WO2009067536), a transdermal patch (e.g. U.S. Pat. Nos. 5,004,610; 5,342,623; 5,344,656; 5,364,630; 5,462,745; and 5,508,038; 5,077,104; 5,268,209; 4,908,027; 5,633,008; 4,839,174; 4,943,435; and 5,167,242) or any other form suitable for use.

Pharmaceutical formulations containing the agent(s), compound(s), or drug(s) or composition(s) of the present invention may be prepared in any form, such as oral dosage form (powder, tablet, capsule, soft capsule, aqueous medicine (e.g. U.S. Pat. No. 6,068,850), syrup, elixirs pill, powder, sachet, granule), or topical preparation (cream, ointment, lotion, gel, emulgel (e.g. WO2007129162), balm, patch, paste, spray solution, aerosol and the like), or injectable preparation (solution, suspension, emulsion).

The compositions and formulations of the invention relate to preventing the effects of aging and cell death induced by UV radiation. The invention also relates to the use of these compositions as tan extenders.

The compositions of the invention can be in the form of cosmetic creams, gels, lotions, milks, emulsions and solutions, ointments, sprays, oils, body lotions, shampoos, lotions after-shave, deodorants, soaps, lip sticks protectors, sticks and pencils for makeup.

The compositions of the present invention may comprise flavorings (e.g. extract of ginger, mint, strawberry, vanilla, etc).

In the form of a gel, the compositions and formulations include suitable excipients such as cellulose esters or other gelling agents such as carbopol, guar gum, etc.

The compositions in pharmaceutical dosage forms may be used in the form of their pharmaceutically acceptable salts and complexes, and also may be used alone or in appropriate association, as well as in combination with other pharmaceutically active compounds.

Such compositions and formulations can be administered to a subject animal such as mammals (rat, mouse, domestic animals or human) via various routes. All modes of administration are contemplated (e.g. orally, rectally or by intravenous, intramuscular, subcutaneous, intra-cutaneous, intrathecal, epidural or intra-cerebroventricular injection).

The compositions and formulations described herein also allow for the production of a "functional health food" comprising the agent(s), compound(s), or drug(s) of the present invention for the prevention and improvement of a condition, disease, or disorder in a subject. The term "a functional health food" defined herein is the functional food providing enhanced physical, psychological, physiological, or other functionality by adding the compositions, agent(s), compound(s), drug(s), analogs, derivatives, or formulations of the present invention to conventional food for the benefit of a human or mammal.

Examples of suitable pharmaceutical vehicles are also described in Remington's Pharmaceutical Sciences, Alfonso R. Gennaro ed., Mack Publishing Co. Easton, Pa., 19th ed., 1995, pp. 1447 to 1676, incorporated herein by reference.

It will be apparent to those skilled in the art that various modifications and variations can be made in the compositions, use and preparations of the present invention without departing from the spirit or scope of the invention.

In some embodiments, the agents, compounds, or drugs of the present invention are modified chemically using novel means as well as any means known to the art (e.g. Brandi et al., 2003; Kassouf et al., 2006; Chao et al., 2007; Cho et al., 2007; Weng et al., 2007; Lin et al., 2008; U.S. Pat. No. 6,974,801).

In some embodiments, the compositions and formulations of the present invention are the product of mixing the compounds and drugs in their wet or liquid forms, In some embodiments, the compositions and formulations of the present invention are the product of mixing the compounds and drugs in their wet or liquid forms, and subsequently preparing solutions, suspensions, emulsion, tablets, pills, pellets, capsules capsules containing liquids (e.g. WO2010106191), powders, sustained-release formulations, suppositories, emulsions, aerosols, sprays, suspensions.

In some embodiments, the compositions and formulations of the present invention are the product of mixing the compounds and drugs in their dry or solid forms, In some embodiments, the compositions and formulations of the present invention are the product of mixing compounds, agents and drugs in their dry or solid forms and subsequently encapsulating those compounds, agents and drugs in a capsule for oral administration. In some embodiments, the compositions and formulations of the present invention are the product of mixing compounds, agents and drugs in their dry or solid forms and subsequently suspending those compounds, agents and drugs in a suspension.

In some embodiments, the compositions and formulations of the present invention are the product of mixing compounds, agents and drugs in their dry or solid forms and subsequently preparing solutions, suspensions, emulsion, tablets, pills, pellets, capsules, capsules containing liquids, powders, sustained-release formulations, suppositories, emulsions, aerosols, sprays, suspensions.

In some embodiments, the compositions and formulations of the present invention are the product of mixing compounds, agents and drugs in their dry or solid forms, preparing tablets, pills, pellets, capsules, capsules, etc. and subsequently coating those compounds, agents and drugs with an enteric coating.

In one embodiment, the compositions and formulations of the present invention utilize a soft gel capsule (U.S. Pat. Nos. 2,780,355, 4,497,157, 4,777,048, 4,780,316, 5,037,698 and 5,376,381).

The compositions or formulations of the present invention can be mixed with suitable pharmaceutical carriers (vehicles) or excipients known to the art (e.g. Kumar et al., 1996; Akers et al., 2002; Strickley et al., 2004; Jacob et al., 2010; Siddiqui et al., 2010; Pilcer et al., 2010). Examples include water-soluble organic solvents, non-ionic surfactants, water-insoluble lipids, organic liquids/semi-solids, cyclodextrins and phospholipids. They may also include gelatin, lactic acid, stearic acid or salts or complexes thereof, starch, milk, sugar, certain types of clay, including magnesium or calcium stearate, talc, oils, gums, vegetable fats, lipids, or and glycols.

Examples of acceptable salts useful in the invention include, but are not limited salts formed with inorganic acids (e.g. those selected from the group consisting of hydrochloric, hydrobromic, sulfuric, phosphoric, nitric or equivalent), or salts formed with acids or organic acids (e.g. acetic, oxalic, tartaric, succinic, malic, fumaric, aleic, ascorbic, benzoic acid, tannic, alginic, polyglutamic, naphthalene sulfonic acid, naphthalene disulfonic acid and polygalacturonic).

In some embodiments, one or more agents, compounds, or drugs of the present invention is mixed with omega 3 fatty acids, olive oil, or other source of lipid.

In some embodiments, one or more agents, compounds, or drugs of the present invention is conveyed to the body in conjunction with omega 3 fatty acids.

In some embodiments, one or more agents, compounds, or drugs of the present invention is conveyed to the body in conjunction with omega 3 fatty acids together in a capsule.

The buffering agents of the present invention may be any salt or buffering agent. Examples include sodium chloride, potassium chloride, or sodium phosphate or potassium phosphate. In some embodiments, the salt and/or buffering agent is useful in maintaining osmolality in a suitable range for administration of the composition or formulation to a human or an animal. The salt or buffering agent may preferably be present at isotonic concentration of about 150 mM to about 300 mM.

Examples buffers include sodium biphosphate, potassium biphosphate, sodium bicarbonate, potassium bicarbonate, carboxylic acids and their salts, such as, ascetic acid/sodium acetate and citric acid/potassium citrate.

The buffering agent will in some embodiments, maintain the pH of the composition or formulation in the range of about 5.5 to about 7.5.

The medicinal formulations of the compounds, agents and drugs of the present inventions may utilize conventional diluents, carriers, or excipients etc., known to the art.

In some embodiments, the compositions and formulations of the present invention may comprise a stabilizer, a surfactant, a nonionic surfactant, and may comprise a salt and/or a buffering agent.

In some embodiments, the compound, agent or drug of the present invention may be delivered in the form of an aqueous solution (e.g. WO/2000/025,765), a lipid, or in a lyophilized form. In some embodiments, the compositions and formulations of the present invention are the product of mixing compounds, agents and drugs in their dry or solid forms and subsequently loading those compounds, agents and drugs into lipid.

In some embodiments, the compositions and formulations of the present invention are the product of mixing compounds, agents and drugs in their dry or solid forms and subsequently loading those compounds, agents and drugs into liposomes (e.g. see Langer, 1990. Science 249:1527-1533; Treat et al, in Liposomes in the Therapy of Infectious Disease and Cancer, Lopez-Berestein and Fidler (eds.), Liss, N.Y., pp. 353-365 (1989); Lopez-Berestein, ibid., pp. 317-327).

In some embodiments, the compositions and formulations of the present invention are the product of mixing compounds, agents and drugs in their dry or solid forms and subsequently loading those compounds, agents and drugs into solid lipid nanoparticles.

In some embodiments, the compositions and formulations of the present invention are the product of mixing compounds, agents and drugs in their dry or solid forms followed by loading those compounds, agents and drugs into solid lipid nanoparticles and/or liposomes followed by drying or lyophilizing the mixture.

In a further preferred embodiment, the dried or lyophilized liposomes and/or solid lipid nanoparticles are encapsulated for oral administration.

In embodiments involving a stabilizer, the stabilizer may be any suitable stabilizer known to the art (e.g. Stella and Rajewski, 1997; Merisko-Liversidge and Liversidge, 2003; U.S. Pat. No. 5,376,359). The stabilizer, may for example, be an amino acid, such as for instance, glycine; or an oligosaccharide, such as for example, sucrose, tetralose, lactose or a dextran. The stabilizer may also be a sugar alcohol, such as mannitol or a combination the stabilizer types described above.

In one embodiment, a stabilizer or stabilizers constitute approximately 0.1% to about 10% weight for weight of the compound.

In one embodiment, the surfactant is a nonionic surfactant (e.g. polysorbate or Tween20). In some embodiments, Tween80; a polyethylene glycol or a polyoxyethylene polyoxypropylene glycol is included at approximately 0.001% (w/v) to about 10% (w/v).

In some embodiments, the formulations of the compositions or formulations useful in the methods of the present invention contain one or more conventional additives.

Additives include a solubilizer (e.g. US20070021325; U.S. Pat. No. 6,669,964; WO2009126950; WO2009101263). Additives may comprise glycerol or an antioxidant such as for example, benzalkonium chloride, benzyl alcohol, chloretone or chlorobutanol. Additives may also include an anesthetic.

To reduce oxidation and spoilage, the pharmaceutical compositions and formulations may be stored under nitrogen gas or argon gas in sealed vials.

Specialized Methods of Delivery

In some embodiments, the compounds, drugs or agents of the present invention may be administered to a cell in vitro, ex vivo, or in vivo utilizing nanoparticles (Martins et al., 2009; WO/2010/013224), Such delivery allows for improved absorption and/or pharmacokinetics of the compounds, drugs or medicinal formulations.

In some embodiments, the compounds, drugs or agents of the present invention may be administered to a cell utilizing liposomes, nanoparticles, nanocapsules, nanovaults, etc. (see Goldberg et al., 2007; Li et al., 2007; Martins et al., 2009; Hu et al., 2010; Huang et al., 2010). In some embodiments, the agents, compounds, drugs of the present invention may be administered to a cell in vitro, ex vivo, or in vivo utilizing nanoparticles, liposomes (WO/2010/009186; WO/2009/141450; WO/2009/065065; WO/2004/069224; WO/1999/013865), nanocapsules, nanovaults, In some embodiments, the compounds, drugs or medicinal formulations of the present invention may be administered to a cell utilizing liposomes, nanocapsules, nanovaults, nanosuspensions, etc. (see Sholer et al., 2001; Goldberg et al., 2007; Li et al., 2007; Hu et al.; 2010; Huang et al., 2010), In some embodiments, the compounds, drugs or medicinal formulations of the present invention may be administered using nanovaults engineered to allow cell type specific targeting (Kickhoefer et al. ACS Nano 3, 27-36 (2009)).

In some embodiments, the compounds, drugs or medicinal formulations of the present invention may be administered using recombinant nanovaults.

In some embodiments, the compounds, agents, or drugs of the present invention are incorporated into nanoparticles allowing absorption of orally administered compositions or formulations increasing bioavailability (especially oral bioavailability).

In some embodiments, a compound, agent or drug of the present invention is incorporated into nanoparticles, liposomes, and/or nanovaults allowing increased bioavailability of the compound, agent or drug.

In some embodiments, the compounds, agents, or drugs of the present invention are loaded into solid lipid nanoparticles by ultrasonic and high-pressure homogenization.

In some embodiments, compounds, agents and drugs of the present invention are loaded into solid lipid nanoparticles by ultrasonic and high-pressure homogenization along with Sodium Carboxymethyl Cellulose.

In some embodiments, the drugs and compounds of the present invention are 44 incorporated into engineered nanomaterials, nanoliposomes, nanoemulsions (e.g. WO2010070675), nanoparticles and nanofibers (Weiss et al., 006; 2007) for further incorporation into all manner of medicinal formulations and food items of all types, including, for example, milkshakes, muffins, hamburgers, fruit cocktails, granola, trail mix, vitamin drinks, sports drinks (U.S. Pat. Nos. 5,780,094; 4,981,687), nutritional supplements and energy drinks (U.S. Pat. No. 5,744,187; etc. (see Handbook of Functional Lipids; and "Food Nanotechnology,—an overview" by Sekhon (2010), as well as Milk and Milk Products: Technology, Chemistry and Microbiology by Varnam and Sutherland (2001) for reviews).

In some embodiments, the compositions or formulations of the present invention comprise a combination of compositions or formulations named herein.

In one embodiment, the compounds, agents, or drugs of the present invention are loaded into solid lipid nanoparticles by ultrasonic and high-pressure homogenization.

In one embodiment, the compounds, agents, or drugs of the present invention are loaded into solid lipid nanoparticles (e.g. KR1020080014379; WO/2006/102768; WO/2000/006120).

In one embodiment, the compounds, agents, or drugs of the present invention are loaded into solid lipid nanoparticles by ultrasonic and high-pressure homogenization along with Sodium Carboxymethyl Cellulose (Hu et al., 2010).

In one embodiment, the compounds, agents, or drugs of the present invention are encapsulated into solid lipid nanoparticles (SLN) utilizing a double emulsion solvent evaporation (w/o/w) method (Li et al., 2010).

In another preferred embodiment, compounds, agents, or drugs of the present invention are PEGylated by Chemical conjugation with PEG.

In one embodiment, the compounds, agents, or drugs of the present invention are complexed with crystalline ascorbic acid in solid lipid nanoparticles.

In one embodiment, the agents, compounds, or drugs of the present invention are conjugated, coupled, linked or complexed with glutathione (GSH), In one embodiments, wherein zerumbone and/or other agent(s), compound(s), or drug(s) of the present invention is selected for use in the present invention, the zerumbone and/or other agent(s), compound(s), or drug(s) of the present invention is conjugated, coupled, linked or complexed with glutathione.

In one embodiment, the agents, compounds, or drugs of the present invention are conjugated, coupled, linked or complexed with a nitric oxide (NO)-donor moiety.

In one embodiment, the agents, compounds, or drugs of the present invention are conjugated, coupled, linked or complexed with a nitric oxide (NO)-donor moiety.

Relevant example methods for coupling or conjugating a nitric oxide moiety to an agent, compound, or drug named herein have previously been described (e.g. WO92/01668, WO 95/30641, WO 97/16405; U.S. Pat. No. 5,859,053; WO/2002/011706; WO2010118968).

In one embodiment, an nitric oxide (NO)-donor moiety is conjugated, coupled, linked or complexed with an approved drug named or described herein, zerumbone and/or other agent(s), compound(s), or drug(s) of the present invention, glutathione, auraptene, ethacrynic acid, curcumin, a curcuminoid, hispolon, dehydroxyhispolon, methoxyhispolon, bisdemethylcurcumin, hispolon methyl ether, hydroxyhispolon, methoxyhispolon methyl ether, a triterpenoid, zingerone, reservatrol, vanillin, rosmarinic acid, a methoxyflavone, a sesquiperetene, n-acetylcysteine, trimethylglycine, folinic acid, folic acid, an amino acid, an ATF4 modulator, a flavone, a flavonoid, quercetin, a shogaol (e.g. 6-shogaol), a gingerol (e.g. 6-gingerol), zingerol, kavalactone, sulforaphane, allyl-, butyl- and phenylethyl-isothiocyanate, chlorophyllin, alpha-lipoic acid, allicin, plumbagin, protandim, capsaicin, a capsaicinoid, piperine, asafetida, eugenol, piperlongumine, pellitorine, zingiberine, tBHQ, CDDO-Im, MC-LR, epigallocatechin-3-gallate, a compound found in wasabi, cafestol, xanthohumol, 5-O-caffeoylquinic acid, N-methylpyridinium, resveratrol, nootkatone, caffeic acid phenethyl ester, 3-O-Caffeoyl-1-methylquinic acid, silymarin, kahweol, garlic organosulfur compounds, lycopene, carnosol (rosemany), an avicin, oltipraz, CDDO, a neurite outgrowth promoting prostaglandin, vitamin D, a B vitamin, andrographolide, an amino acid, s-allylcysteine, Vitamin A, Vitamin C, Vitamin E, β carotene, trans-2-hexenal, cyclopentenone, ajoene, Dihydro-CDDO-trifluoroethyl amide, Hypochlorous acid, Fragrant unsaturated aldehydes (e.g. trans-cinnamaldehyde, safranal, 2,4-octadienal, citral, and trans-2,cis-6-nonadienal), 2-OHE, 4-OHE, bucillamine, acrolein, momordin, momordol, momordicin I, momordin II, momordicosides, momordicin-28, momordicinin, momordicilin, momordenol, momorcharin, cucurbitacin B, charantin, charantosides, goyaglycosides, α-eleostearic acid, 15,16-dihydroxy-α-eleostearic acid, antirheumatic gold(I) compounds, an avicin, dithiolethione, an approved drug, and/or a compound, agent or drug extracted from cloves, black pepper, red chili, cinnamon (e.g. cinnamic aldehyde), ginger, garlic, onion, fennel, bay leaves, nutmeg, saffron or coriander, In one embodiment, the agents, compounds, or drugs of the present invention covalently linked through an aromatic spacer to an NO-releasing moiety (e.g. —ONO2) (Del Soldato et al., 1999; Bratasz et al., 2006).

In some embodiments, wherein zerumbone and/or other agent(s), compound(s), or drug(s) of the present invention is selected for use in the present invention, the zerumbone and/or other agent(s), compound(s), or drug(s) of the present invention is conjugated, coupled, linked or complexed with a nitric oxide-donor moiety.

In some embodiments, wherein oltipraz is selected for use in the present invention, the oltipraz is conjugated, coupled, linked or complexed with a nitric oxide-donor moiety.

In some embodiments, wherein zerumbone and/or other agent(s), compound(s), or drug(s) of the present invention is selected for use in the present invention, the zerumbone and/or other agent(s), compound(s), or drug(s) of the present invention is covalently linked through an aromatic spacer to an NO-releasing moiety (e.g. —ONO2) (Del Soldato et al., 1999; Bratasz et al., 2006).

In one embodiment, the agents, compounds, or drugs of the present invention are conjugated, coupled, linked or complexed with a nitric oxide-donor moiety as well as with glutathione.

In some embodiments, the agents, compounds and drugs of the present invention are biotinylated, fluorinated, or difluorinated.

In one embodiment, the compositions and formulations of the present invention are used to incubate the cells of WO2008150814.

In one embodiment, the compositions and formulations of the present invention are used in combination with the cells, vectors or methods of WO2008150814.

In one embodiment, the composition(s), formulation(s) and combination(s) of the present invention comprise metronidazole and itraconazole to treat a protozoal disease with synergistic efficacy.

In one embodiment, an additional agent(s), compound(s) or drug(s) of the present invention, as well as metronidazole, is combined with itraconazole to treat a protozoal disease.

In some embodiments, the composition(s), formulation(s) and combination(s) of the present invention comprise metronidazole, ciprofloxacin and itraconazole.

In one embodiment, the composition(s), formulation(s) and combination(s) of the present invention comprise metronidazole, ciprofloxacin and itraconazole.

In one embodiment, the composition(s), formulation(s) and combination(s) of the present invention comprise metronidazole, itraconazole and a non-approved drug named herein.

In one embodiment, the composition(s), formulation(s) and combination(s) of the present invention comprise metronidazole, itraconazole and a sesquiterpene.

In one embodiment, metronidazole, ciprofloxacin are combined with itraconazole to treat a protozoal disease with synergistic efficacy.

In some some embodiments, the drug formulations for preventing or treating a protozoal disease comprise agents from the drug classes represented by metronidazole and itraconazole and/or additional agent(s), compounds(s), or drug(s) of the present invention.

In some some embodiments, the formulation or method for treating or preventing a parasitic illness comprises: one or more triazoles selected from Itraconazole, Fluconazole, Isavuconazole, Ravuconazole, Posaconazole, Voriconazole and Terconazole; one or more nitroimidazoles selected from Metronidazole, Tinidazole, Nitroimidazole, Azanidazole, Secnidazole, Ornidazole, Propenidazole, and Nimorazole; and one or more agents, compounds, or drugs described herein.

In further embodiments, the formulation or method for treating or preventing a parasitic illness comprises one or more triazoles selected from Itraconazole, Fluconazole, Isavuconazole, Ravuconazole, Posaconazole, Voriconazole and Terconazole; one or more nitroimidazoles selected from Metronidazole, Tinidazole, Nitroimidazole, Azanidazole, Secnidazole, Ornidazole, Propenidazole, and Nimorazole; mefloquine, doxycycline, choroquine, hydroxychoroquine, Malarone, atovaquone, Proguanil (Malarone), an artemisinin-based compound, antimony, amphotericin, miltefosine, paromomycin, and one or more agents, compounds, or drugs described herein.

EXAMPLES

The invention is now considered with respect to specific examples, though not limited thereby. As used within the following examples, the term "zerumbone and/or other agent(s), compound(s), or drug(s) of the present invention" refers to all conjugates and derivatives of zerumbone and/or other sesquiterpenes, agent(s), compound(s), or drug(s) of the present invention, as well as all conjugates and derivatives of all agents, compounds, and drugs of the present invention. Thus, examples directed toward the inclusion of zerumbone in a composition or formulation also represent examples directed toward the inclusion of the other agents, compounds, and drugs described herein, as well as their analogs, isomers and/or derivatives at appropriate dosages. Accordingly, the amounts of the other components of the compositions and formulations may likewise be appropriately scaled in relation to the mass of actually included agent(s), compound(s) or drug(s). Thus, it should be understood that the example compositions and formulations below may be altered by inclusion of OTC, and/or approved drug(s) in accordance with some embodiments of the invention. As used within the following examples, the term "glutathione" refers to all analogs, conjugates and derivatives of glutathione (e.g. glutathione monoethylester), Example 1: Preparation of Solid Lipid Nanoparticles In one embodiment, the method chosen for the preparation of nanoparticles is an adaptation of the w/o/w double emulsion technique (Garcia-Fuentes et al 2003; Zhang et al 2006; Sarmento et. al., 2007). Approximately 200 mg of acetyl palmitate is dissolved in about 4 mL of dichloromethane. 7 mg of zerumbone, a sesquiterpene and/or an equivalent effective amount of other agent(s), compound(s), or drug(s) of the present invention and glutathione) are dissolved in 0.5 mL of HCL 0.1 M. The drug solution is added to the lipid solution and then homogenized for 30 seconds in an ultra-turrax T25 (IKA-Labortechnik, Germany) or a similar apparatus. The primary emulsion is then poured into 25 mL of 2% poloxamer 407 solution and homogenized for another 30 seconds. The solvent is subsequently discarded and the emulsion is concentrated in a rotavapor until ~10 mL. Optionally, particle size can be analyzed using photon correlation spectroscopy (PCS); and electrophoretic mobility can be measured with Laser Doppler Anemometry (LDA) using a Malvern Zetasizer 5000 (Malvern Instruments, UK) or similar apparatus. Samples can be diluted with Milli-Q-water having a conductivity adjusted to 50 $\mu$S/cm by addition of a 0.9% NaCl solution.

The amount of the agent(s), compound(s) or drug(s) incorporated into SLN may be calculated by the difference between the total amount used to prepare the systems and the amount of compound or drug remaining in the aqueous phase after SLN isolation. After preparation, aqueous SLN dispersions may be centrifuged (by ultracentrifuge, rotor type 80Ti, Beckman Instruments, German or analogous instrument or similar apparatus) for about 2 hours at 45000 rpm (corresponding to approx. 190000×g). Compound, agent or drug concentration in the supernatant may be determined by HPLC (Sarmento et al 2006).

Example 2: Preparation of a Liposomal Formulation

A liposomal formulation comprising the agent(s), compound(s), and drug(s) of the present invention may be prepared according to Good Manufacturing Practices by the method of (Paul et al. (1997), previously described by Fessi et al. (1988). Briefly, an organic phase containing phospholipids and the drugs is introduced under magnetic stirring in an aqueous phase. The organic solvent is evaporated, and the liposomes obtained are filtered and lyophilized). Prior to administration, 50 mg of lyophilized liposomes are resuspended in sterile distilled water (20 ml), shaken for 3 min, and then diluted in 5% dextrose.

Example 3: Preparation of a Tablet Formulation

Compressed tablets containing the pharmaceutical composition of the invention may be prepared by uniformly mixing the active ingredient(s) with a solid carrier to provide a mixture. The mixture is then compacted to the shape and size desired. Molded tablets maybe made in a suitable machine, To prepare a tablet formulation containing agents, compounds, or drugs of the present invention, the selected active components (e.g. Zerumbone and/or other agent(s), compound(s), or drug(s) of the present invention (80 g) and reduced glutathione (400 g)) may be mixed in the dry state for 10 minutes in a Z-blade mixer. Likewise, a solution is prepared containing gelatin (16 g), dioctyl sodium sulphosuccinate (1 g), alcohol (57 g) and purified water (80 g). The solution is then wet-mixed with the powders for 10 minutes using a slow speed. The wet mass is passed through a 1000 $\mu$m screen. Subsequently, the granules are dried in a fluidized bed at 60° C. for 30 minutes. The dried granules can then be sifted through a 1000 $\mu$m screen. Likewise, magnesium stearate (4.8 g) is sifted to 125 $\mu$m, and can be blended with the granules. Finally, the resulting mixture compressed on a Manesty D3 Rotary machine to provide tablets (U.S. Pat. No. 4,209,513).

Example 4: Preparation of a Stable Liquid Composition

On order to prepare a stable liquid composition comprising the agents, compounds, or drugs of the present invention, the following are combined: 1 Excipient Amount/20 mL % of formulation, the active components (e.g. zerumbone, a sesquiterpene, and/or other agent(s), compound(s), or drug(s) of the present invention 2.5 mg, reduced glutathione 2.5 mg), 0.25 mg/mL water or pH 8 15.1 mL 75.5% v/v phosphate buffer glycerin 4 mL 20% v/v HPMC-K4 400 µL of 0.1% solution 0.4 mg 0.002% w/v TWEEN® 80 100 µL 0.5% v/v ethanol 200 µL 1% v/v saccharin 400 µL of 0.1% solution 0.4 mg 0.002% w/v (see U.S. Pat. No. 7,259,185).

Example 5: Preparation of a Syrup Formulation

To prepare a syrup formulation comprising zerumbone, a sesquiterpene, and/or other agent(s), compound(s), or drug(s) of the present invention, 35% of the final batch volume of the purified water (USP/EP qs 1 L) is charged and heated to or at 60-80° C. The sugar (Sucrose Extra Fine Granulated USP 300.0 g/L), sodium benzoate (NF/EP 1.0 g/L), sodium citrate (Dihydrate USP/EP 5.27 g/L) and citric acid (Anhydrous USP/EP 2.15 g/L) are added and mixed until they dissolve. The solution is then cooled to 25-30° C. The sorbitol solution (USP/EP 142.0 g/L) and glycerin (Glycerol Anhydrous USP 150.0 g/L) are added, followed by a solution that contains propylene glycol (USP/EP 100.0 g/L) and a flavorant (1.0 g/L) mixed together. Finally, the zerumbone and/or other agent(s), compound(s), or drug(s) of the present invention (40 g/L) is added and dissolved. The batch is finally brought to final volume by weight, and subsequently passed through a 1.2 micron filter. The concentration of zerumbone and/or other agent(s), compound(s), or drug(s) of the present invention in this syrup formulation may be reduced to accommodate the addition of other agents, compounds, or drugs named herein to produce desirable formulations.

Example 6: Preparation of a Soft Gel Formulation

To prepare a soft gel formulation comprising the agents, compounds, and drugs of the present invention (e.g. zerumbone and/or other agent(s), compound(s), or drug(s) of the present invention), polyoxyethanyl-a-tocopheryl-sebacate (PTS) (150 mg) and zerumbone and/or other agent(s), compound(s), or drug(s) of the present invention (100 mg) are melted and mixed them together at 60° C. To the cooled formulations are added oil Oil (either rice bran oil or omega-fatty acid enriched fish oil (ONC Oil 18/12) (30 mg) and beeswax (50 mg). The formulation is then incubated at 60° C. until the beeswax melts. The formulation is finally mixed again and sealed under argon gas. The concentration of zerumbone and/or other agent(s), compound(s), or drug(s) of the present invention or other agents, compounds, and drugs of the present invention in this soft gel formulation may be reduced to accommodate the addition of other agents, compounds, or drugs named herein to produce desirable formulations.

Example 7: Preparation of a Chewing Gum Formulation

To prepare a chewing gum formulation comprising the agents, compounds, and drugs of the present invention, the active medicaments are preferably added early-on into the mix. The smaller the amount of active ingredient used, the more important it is to preblend that particular ingredient to assume uniform distribution. Whether a pre-blend is used or not, in one embodiment, the agent or medicament should be added within the first five minutes of mixing. If the selected agents, compounds, and drugs are water soluble in the chewing gum, it preferably will include a base/emulsifier system which leads to the desired concentration of the medicament in the saliva (more hydrophilic balance). If the selected agents, compounds, and drugs are water insoluble, the chewing gum preferably includes a base/emulsifier system which leads to the desired concentration of the medicament in the saliva (more lipophilic balance). In manufacturing the gum ingredients may include the following Sugar (54.77%), Gum Base (21.80%), Corn Syrup (11.20%), Fructose (5.60%) Glycerine (3.40%) Active drug(s) (1.70%) Flavors (1.00%), Artificial Sweetener (0.26%), Soluble Saccharin (0.21%) and Insoluble Saccharin (0.06%). The precise percentages and many of the ingredients may vary (U.S. Pat. No. 7,078,052).

Example 8: Preparation of an Overcoated Chewing Gum Formulation

To prepare an overcoated chewing gum formulation comprising the agents, compounds, and drugs of the present invention, the Gum Center is made as follows: Gum Base 33%, Calcium Carbonate 13%, Sorbitol 44.23%, Glycerin 4%, Flavors 2.32%, Zerumbone and/or other agent(s), compound(s), or drug(s) of the present invention 2%, Lecithin 0.6%, Sweeteners 0.9%. The center is sprayed with dried maltodextrin/zerumbone and/or other agent(s), compound(s), or drug(s) of the present invention at 50% active zerumbone and/or other agent(s), compound(s), or drug(s) of the present invention. The Gum Coating is composed of Coating Syrup 3, Coating Syrup 4, Xylitol 64.14%, Water 11.14%, 40% Gum Tahla Solution 20.87%, Titanium Dioxide Whitener 0.40% Peppermint Flavor 3 1.40%, Sweeteners 0.27%, Talc Polishing Agents 1.78%. The Flavor is added in 3 additions after 3 separate syrup additions within the coating syrup (1.4%). Finally, after completion of coating, the overcoated gum is polished. Following this protocol, the initial center piece achieves a weight of about 0.995 grams. The Gum is then coated to a finished piece weight of 1.52 grams to give a 34.5% coating. Coating syrup 3 is used to coat the first 60% of the coating to a piece weight of 1.30 grams. Coating syrup 4 is used to coat to the final piece weight (U.S. Pat. No. 6,290,985). The amount of zerumbone and/or other agent(s), compound(s), or drug(s) of the present invention and the other ingredients in this gum formulation may be adjusted to accommodate the addition of other agents, compounds, or drugs named herein to produce desirable formulations.

Example 9: Preparation of a Troche Comprising a Sesquiterpene and/or Other Agent(s), Compound(s) or Drug(s) of the Present Invention Long-lasting troches gradually release an active ingredient thereby prolonging absorption and duration of drug action. Troches also allow for sublingual absorption of agents that may have poor intestinal bioavailability (U.S. Pat. No. 3,312,594). To prepare a troche comprising zerumbone and/or other agent(s), compound(s), or drug(s) of the present invention, and/or the other agents, compounds, or drugs of the present invention, equal amounts of carboxymethylcellulose, pectin, and gelatin (e.g. 330 g each), are thoroughly admixed with magnesium stearate (e.g. 10 g) and with the active compounds, agents, or drugs (in appropriate concentrations). Afterwards, the mixed powder is compressed in a Stokes machine (or similar apparatus) to form troches of 500 mg each. The amount of zerumbone and/or other agent(s), compound(s), or drug(s) of the present invention and the other ingredients may be adjusted to accommodate the addition of other agents, compounds, or drugs named herein to produce desirable formulations.

Example 10: Preparation of a Sports Drink

To prepare a sports drink, desired and workable amounts of each compound, agent, or drug of the present invention may be added to sugar(s) selected from Galactose, Fructose, and Glucose (e.g. 2.5 g/100 ml), Sodium Chloride (e.g. 0.2 g/100 ml), Potassium (0.04 g/100 ml), Dihydrogen orthophosphate Magnesium (e.g. 0.01 g/100 ml). Citric acid or citrate may be used in an amount of 0.1 to 0.5% w/v as needed. When sodium citrate is used, the quantity of sodium chloride may be reduced in exact molar proportion to the sodium ions added as sodium citrate (up to 34 mmol·l-1). Furthermore, caffeine and flavorings may be incorporated as desired. Preservatives, for example sodium benzoate or sorbic acid may likewise be employed. Vitamin C may be used as an antioxidant in an amount to 0.5% w/v as needed. The proportions set out above may be varied, but typically by 25% or less.

Alternatively, a composition or formulation for providing the health benefits listed herein while also providing a rapid source of energy, electrolyte balance, blood volume, and performance enhancement, may be produced by combining desired and workable amounts of each compound, agent, or drug of the present invention (e.g. zerumbone and/or other agent(s), compound(s), or drug(s) of the present invention 0.5 to 10% (preferably 3%), glutathione 0.5-10% (preferably 3%)), with electrolytes selected from e.g. sodium, potassium, chloride, phosphate, bicarbonate, sulfate, magnesium and calcium (e.g. about 1 meq/1 to 6 meq/1 potassium, 12 meq/1 to 33 meq/1 sodium, about 2 meq/1 to about 8 meq/1 phosphate), 0.5% to 5% glycerol (e.g. 1%), and about 2% to 8% sugar compound (e.g. 5% fructose, sucrose, glucose or other sugar). Specifically, the composition may have a glucose concentration of from about 2% to about 8%.

Preferably, the sugar concentration may be about 4%. The drink may be carbonated. In addition, caffeine may also be added (e.g. about 120-180 mg/1), as may other compounds such as vitamins, minerals, citric acid, citrate, preservatives, flavorings, sweeteners, and others. The proportions set out above may be varied, but typically by 25% or less.

Example 11: Preparation of a Stable Aqueous Formulation Comprising Peptide Compounds in Water To prepare a stable aqueous formulation suitable for the provision of zerumbone, a sesquiterpene, and/or other agent(s), compound(s) or drug(s) of the present invention, in combination with peptides including oligopeptides (e.g. reduced glutathione), the zerumbone and reduced glutathione (and other agents, compounds or drugs of the formulation) are weighed (to achieve desired concentrations—e.g. total=40%) and then added to a weighed amount of vehicle (sterile distilled water, ethanol/water or water with non-ionic surfactant) at the appropriate concentration (w/w), then gently stirred to dissolve.

Example 12: Preparation of a Powder Pharmaceutical Preparation Dissolvable in a Liquid to Form a Solution Prior to Ingestion The powder pharmaceutical composition comprises safe and effective amount of the active agents. To prepare a Powder Pharmaceutical formulation suitable for the provision of zerumbone and/or other agent(s), compound(s), or drug(s) of the present invention, one may mix Ascorbic Acid (1.20%), Citric Acid (10.50%), Honey Buds Flavor (3%), Honey Powder Flavor (4%), Natural Lemon Flavor (5%), Natural Lime Flavor (6%), Sweet-Ung (7%), Sodium Saccharin (0.30%), and Sugar Extra Fine Granulated (69.4985%).

Example 13: Preparation of Encapsulated Nanoparticles

To prepare encapsulated nanoparticles of zerumbone and/or other agent(s), compound(s), or drug(s) of the present invention, one may employ a single emulsion technique (Shaikh et al., 2009; 20090312402), a double emulsion technique, or a multi-emulsion technique.

Example 14: Complexation of Polyphenols (e.g. Flavones and Flavonoids) of the Present Invention to Provide for Increased Absorption Phosphatidylcholine (PC) may be used to increase the bioavailability of polyphenol compounds. Upon oral ingestion, the amphipathic PC molecules facilitate movement of the polyphenol through the intestinal epithelium to the bloodstream (Kidd, 2009).

Example 15: The Preparation of a Nasal Spray or Ocular Drops

To prepare a nasal spray/ocular drops formulation comprising zerumbone and/or other agent(s), compound(s), or drug(s) of the present invention, a borate buffer may be prepared by dissolving 3.81 g of sodium tetraborate in 100 ml of water; dissolving 6.8 g of boric acid in 100 ml of water; and adjusting the pH of the sodium tetraborate solution to a pH of 7.1-7.3 by the addition of boric acid to provide a buffer. Subsequently, 60 mg zerumbone and/or other agent(s), compound(s), or drug(s) of the present invention, 1 g of Tween80 and 1 g PEG may be combined and stirred well using a glass rod prior to sonication for 30 min or until the zerumbone and/or other agent(s), compound(s), or drug(s) of the present invention and/or other agents, compound, or drugs of the present invention is completely solubulized. To prepare an ophthalmic formulation, HPMC is added to 100 ml water and stirred until the HPMC is fully dissolved. Subsequently, the zerumbone and/or other agent(s), compound(s), or drug(s) of the present invention, and/or other agent(s), compound(s) or drug(s) of the present invention/tween80 solution is added drop by drop and stirred for 15 minutes. NaCl, BAC, and EDTA are added and stirred until all the contents dissolve completely before adjusting the pH to 6.5 with borate buffer.

Example 16: Preparation of a Nanoemulsified Topical Formulation

To prepare a nanoemulsified topical formulation comprising zerumbone and/or other agent(s), compound(s), or drug(s) of the present invention, 5.28 g of glyceryl monosterate, 2.64 g of polyethylene glycol (PEG400), (+/−1 ml DMSO) and 2.64 g cetyl alcohol are transferred to a clean 50 ml beaker, followed by adding 2 ml light liquid paraffin and 100 mg Isopropyl myristate into the emulsifiers; then adding 1 ml Phenyl-2-Ethanol to the above mixture; followed by soaking 13.2 g of collagen in 10 ml of demineralised water till the solution becomes clear (~25 min);

followed by adding 100 mg niacinamide. Afterwards, 250 mg of zerumbone and/or other agent(s), compound(s), or drug(s) of the present invention may be transferred into a clean container and solubilized into a nanoemulsion by mixing and sonicating with Tween 80 and PEG400. At about the same time, the solid emulsifiers, glyceryl monosterate, polyethylene glycol (PEG 400) and Cetyl alcohol are melted at 70 C, and the demineralized water (65 ml) simultaneously heated to 70 C. Then about half of the solubilized zerumbone and/or other agent(s), compound(s), or drug(s) of the present invention is added into the hot emulsifiers to be mixed thoroughly. At this point, the melted emulsifiers may be added into the boiled demineralised water and mixed vigorously at the room temperature; until a creamy consistency is achieved. To this cream, collagen and niacin may be added to form a smooth cream before adding another half the amount of solubilized zerumbone and/or other agent(s), compound(s), or drug(s) of the present invention and mixing. Then 100 µl Bronidox may be dissolved in 1 ml of PEG 400 is then added to the mixture as can be 100 µl of lavender oil to the above cream for fragrance.

Example 17: Preparation of a Soluble, Liquid Formulation Comprising the Agents, Compounds, or Drugs of the Present Invention Zerumbone powder with fine granulometry (having the preferred and advantageous granulometry comprised between about 100 and about 200 µm) may be mixed with citric acid crystals (e.g. granulometry below 150 µm) and the resulting mixture stirred into Polysorbate 80. After heating to 300 C for adequate homogenization, this completed mixture may be mixed for 45 min. then milled with a three-roll-mill (e.g. a Coball mill) and closing aerated with nitrogen to remove present air. The preparation may then be encapsulated in gelatin capsules, preferably about 700 mg per capsule. Both non-coated capsules and enteric coated capsules with addition of E 904 (SHELLAC) may be used. Preferably, the concentration of pure zerumbone and/or other agent(s), compound(s), or drug(s) of the present invention is preferably 6%, with 0.5% citric acid completed to 100% with Polysorbate 80.

Example 18: Preparation of a Hard Shell Capsule or Tablet Formulation

The preparation is made as in example 17, though using a high viscosity emulsifier such as Polysorbate 60. SiO2 may be added until a homogenous and fluid powder is achieved and to produce a percentage of 5% to 50% (preferably 30% to 35%). The resultant powder may then be used to fill hard shell capsules (preferably about 500 mg per capsule) or compressed into a tablet. Preferably, the concentration of zerumbone and/or other agent(s), compound(s), or drug(s) of the present invention, in the final composition is 4%, with 0.35% citric acid and preferably a final concentration of SiO2, of 30%. All percentages are on a weight by weight (w:w) basis.

Example 19

Preparation of Agents, Compounds, and Drugs of the Present Invention Bound to Chitosan Nanoparticles To prepare Chitosan Nanoparticles, a solution of 0.2% Chitosan (w/v) in 1% acetic acid may be prepared by heating the mixture to 75° C. The mixture may then be rapidly cooled to 4° C. and this process repeated several times until a solution of chitosan is obtained. This solution is then heated to 75 C again and sprayed under pressure into water kept stirring very rapidly at 4 C to produce uniformly dispersed chitosan nanoparticles. Such nanoparticles may be concentrated by centrifugation. Subsequently, 1 g of zerumbone, a sesquiterpene, and/or other agent(s), compound(s), or drug(s) of the present invention (and/or other agent(s), compound(s) or drug(s) of the present invention) in 1000 ml of absolute ethanol is added under pressure to vigorously stirred aqueous suspension of chitosan nanoparticles in 1% acetic acid and the resulting suspension may then be stirred overnight at 200-1400 rpm at room temperature to load zerumbone and/or other agent(s), compound(s), or drug(s) of the present invention on the chitosan nanoparticles.

Example 20: Preparation of Zerumbone Nanoparticles 1 g of zerumbone and/or other agent(s), compound(s), or drug(s) of the present invention, and/or other agent(s), compound(s) or drug(s) of the present invention, may be dissolved in 1000 ml of absolute ethanol. The solution may then be kept at 40° C. and then sprayed under nitrogen atmosphere and high pressure into 0.1% aqueous acetic acid solution. The solution is to be kept stirring at 200-1400 rpm at room temperature. The particle size can be controlled by varying the pressure at which the zerumbone solution is sprayed into 0.1% aqueous acetic acid kept at different temperatures (25° C.-40° C.)

Example 21: Preparation of Zerumbone-Arginine or -Lysine

In order to prepare a zerumbone-arginine or -lysine for administration, zerumbone and/or other agent(s), compound(s), or drug(s) of the present invention is dissolved under heat in methanol, while a lysine or arginine base is dissolved in water. Subsequently, the lysine/arginine solution is stirred into the zerumbone and/or other agent(s), compound(s), or drug(s) of the present invention solution.

Example 22: Process for Reducing the Crystalline Nature of Agent(s), Compound(s) or Drug(s) of the Present Invention to Increase Solubility and Enhance Activity To prepare zerumbone and/or other agent(s), compound(s), or drug(s) of the present invention, with diminished crystalline state, a process may be undertaken comprising: 1. preparing a mixed solution containing zerumbone and/or other agent(s), compound(s), or drug(s) of the present invention and water-soluble or insoluble polymer in organic solvent or purified water; and 2. solid-dispersing the zerumbone and/or other agent(s), compound(s), or drug(s) of the present invention in the mixed solution in a polymer solution by using a spray dryer or fluidized bed granulator. In this context, the water-soluble polymer may be alginic acid, alginate or its derivatives, α-cyclodextrin or its derivatives, β-cyclodextrin or its derivatives, polyvinylpyrrolidone or its derivatives: polyvinylpyrrolidone-vinylacetate copolymer, γ-cyclodextrin or its derivatives, polyoxyethylene-polyoxypropylene copolymer, polyethyleneglycol or its derivatives, polyvinylalcohol, xanthan gum, or arabic gum, or a combination of polymers.

Example 23: Preparation of Cyclodextrine-Containing Derivatives for Increased Solubility In order to prepare a more aqueous soluble agent(s), compound(s), or drug(s) of the present invention suitable for administration, the agent(s), compound(s) or drug(s) are dissolved under heat in methanol, while lysine or arginine base is dissolved in water (see example 21 above). Subsequently, the lysine/arginine solution is stirred into the zerumbone and/or other agent(s), compound(s), or drug(s) of the present invention solution. The combined solution is then subjected to shaking and evaporation under vacuum, dissolving the non-dissolved residue in ethanol and bringing the mixture to the boiling point. Subsequently, non-dissolved residue is filtered out and the ethanol-based solution is maintained at about −200 C for approximately one hour. Once the zerumbone and/or other agent(s), compound(s), or drug(s) of the present invention lysinate and/or argininate is cooled and collected, it can be added to an aqueous cyclodextrin solution such as HP-beta-CD or HP-gamma-CD at once while agitating well. This new solution is then filtered.

Example 24: Agent(s), Compound(s), or Drug(s) of the Present Invention Dissolved in DMSO To increase it's solubility, zerumbone and/or other agent(s), compound(s), or drug(s) of the present invention may be dissolved in 3% DMSO in sterile phosphate buffered saline (PBS). Subsequently, a 667 µM solution of zerumbone and/or other agent(s), compound(s), or drug(s) of the present invention can be prepared for injection into an animal.

Example 25: A Carbopol Dispersion Comprising the Agents, Compounds and Drugs of the Present Invention In order to prepare a gel comprising agents, compounds, or drugs of the present invention, one may first dissolve disodium edetate (0.05% by weight) in about 90% of the needed water (100% by weight). The agents, compounds, or drugs of the present invention (1-5% by weight) may then be dissolved in solution by mixing until the drug(s) are dissolved to form a drug solution. After dissolving methylparaben (0.17%) and propylparaben (0.03% by weight) in propylene glycol (10% by weight) using heat as needed up to about 80 C and propeller mixing, one may add this solution slowly while mixing to the drug solution. Then 85% sodium docusate (1% by weight) may be dissolved in the drug solution with propeller mixing. Afterwards, Carbopol (0.6% by weight) is mixed into the drug solution to form a uniform dispersion. After dissolving oxybenzone (1% by weight) in octyl methoxycinnamate (7.5% by weight), one may slowly pour this sunscreen solution into the Carbopol dispersion while mixing with a propeller mixer until uniform. Then one may make a 1% sodium hydroxide solution, with continuous mixing add it slowly and stepwise to the Carbopol® dispersion until the desired pH is attained. Add the remaining water and mix into the gel uniformly.

Example 26: A Water-in-Oil Emulsion Suitable for Topical Administration

In preparing a water-in-oil emulsion (wherein preferably the base composition is included in the water phase and the water phase has a pH of about 5.8 to about 8, and an osmolarity between about 175 to about 330), the composition may include about 2.5 wt. % to about 3 wt. % base composition (e.g. electrolyte, buffer, mild preservative, lubricant) and about 20 wt. % to about 35 wt. % agents, compounds, or drugs of the present invention, If the emulsion is intended for use in a sunscreen, then one or more sunscreen agents may be selected (e.g. from the group consisting of: octyl methoxycinnamate, octyl salicylate, homosalate, titanium dioxide, or a combination of such sunscreen agents).

Example 27: A Water-Proof Sunscreen

In preparing another sunscreen formulation comprising agents, compounds, or drugs of the present invention, the sunscreen composition may include (in the OIL phase) a solvent (10% w/w), a film former (8% w/w), a fatty acid (5% w/w), an emulsifier (2% w/w), a waterproofer (3% w/w), a UV filter (10% w/w), agents, compounds, or drugs of the present invention (33% w/w), Wax (4% w/w), and a preservative (0.7%); may include in the (WATER Phase) water (5% water w/w), humectant (10% w/w), thickener (3% w/w), Neutraliser (0.7% w/w), emulsifier (3% w/w), sequestering agent (0.5%), preservatives (1% w/w), and fragrance (1% w/w).

Example 28: Preparation of a Glutathione-Conjugated or n-Acetylcysteine-Conjugated Agents, Compounds or Drugs of the Present Invention In order to enhance activity, agents, compounds, and drugs of the present invention may be modified by conjugation with glutathione and or n-acetylcysteine by any means known to the art. Zerumbone, zingerone, glutathione and several other agents, compounds, or drugs of the present invention contain a carbonyl group suitable for reaction with nucleophilic glutathione (GSH) or n-acetylcysteine. However, non-carbonyl agents, compounds, or drugs of the present invention are likewise capable of conjugation, coupling, linkage, or complexing with glutathione. The reaction mixture may, for example, comprise between 5 and 25 uM carbonyl-containing substrate in 10 mM potassium phosphate, pH 7.0, and 1 mM GSH. The addition of an effective amount of GSTP1-1 will accelerate the initial rate of GSH-mediated consumption of carbonyl-containing substrate. The mixture is stirred (up to 3 days) at room temperature until a clear solution is obtained.

Example 29: Preparation of a Glutathione-Conjugated Agents, Compounds or Drugs of the Present Invention An agent, compound, or drug of the present invention (e.g. zerumbone and/or other agent(s), compound(s), or drug(s) of the present invention) (4 mmol) and Glutathione (20 mmol, 6.15 g) may be dissolved in H2O (20 ml) and CH2Cl2 (2 ml) by stirring at room temperature until a clear solution is obtained. The clear, colorless solution may then be concentrated to about 10 ml, followed by a slow addition of small amount of MeOH. The mixture is then to be kept in the refrigerator overnight as a white solid precipitates out. The zerumbone and/or other agent(s), compound(s), or drug(s) of the present invention-GSH complex may then be filtered and dried. Thereafter, the newly GSH conjugate may be incorporated into tablets, troches, gels, capsules, etc. as described herein.

Example 30. Addition of Tumerone to a Composition or Formulation of the Present Invention In one embodiment, the bioavailability of zerumbone, a sesquiterpene and/or other agent(s), compound(s), or drug(s) of the present invention is enhanced by addition of essential oil of tumeric or ar-tumerone. Thereafter, the selected agent, compound or drug and the tumerone may be incorporated into tablets, troches, gels, capsules, etc., as described herein.

Example 31. Addition of an Agent, Compound or Drug Containing an NO Donor Moiety to the Compositions or Formulations of the Present Invention In some embodiments, the selected agent, compound or drug (e.g. glutathione or zerumbone and/or other agent(s), compound(s), or drug(s) of the present invention) is first treated in accordance with the methods of WO 92/01668, WO 95/30641, WO 97/16405, U.S. Pat. No. 5,859,053, WO/2002/011706, WO2010118968, Del Soldato et al., (1999), or Bratasz et al., (2006) to obtain a NO-donor derivative. Thereafter, the newly derived NO donor derivative is incorporated into tablets, troches, gels, capsules, etc., as described herein.

Example 32. A Tablet for Administering the Agents, Compounds, or Drugs of the Present Invention zerumbone, a sesquiterpene, and/or other agent(s), compound(s), or drug(s) of the present invention (25 mg), Glutathione (200 mg), Lactose (50 mg), Starch (10 mg) and Magnesium stearate (in appropriate amounts) may be mixed by propeller mixing and a tablet prepared according to methods known to the art for tablet preparation.

Alternatively, zerumbone, a sesquiterpene) and/or other agent(s), compound(s), or drug(s) of the present invention (250 mg), Glutathione (250 mg), Lactose (50 mg), Starch (10 mg) and Magnesium stearate (in appropriate amounts) may be mixed by propeller mixing and a tablet prepared according to methods known to the art for tablet preparation.

Example 33: A Capsule for Administering the Agents, Compounds, or Drugs of the Present Invention Zerumbone, a sesquiterpene, and/or other agent(s), compound(s), or drug(s) of the present invention conjugate (250 mg), Lactose (30 mg), Starch (28 mg), Talc (2 mg) and Magnesium stearate (in appropriate amounts) may be mixed by propeller mixing and a gelatin hard capsule iprepared according to methods known to the art for gelatin hard capsule preparation.

Alternatively, Zerumbone, a sesquiterpene, and/or other agent(s), compound(s), or drug(s) of the present invention 125 mg, Glutathione (125 mg), Lactose (30 mg), Starch (28 mg), Talc (2 mg) and Magnesium stearate (in appropriate amounts) may be mixed by propeller mixing and a gelatin hard capsule prepared according to methods known to the art for gelatin hard capsule preparation.

Example 34: A Suspension for Administering the Agents, Compounds, or Drugs of the Present Invention Zerumbone, a sesquiterpene, and/or other agent(s), compound(s), or drug(s) of the present invention (250 mg), Isomerized sugar (10 g), Sugar (30 mg), Sodium CMC (100 mg), Lemon Flavor (in appropriate amounts), and distilled water (sufficient to produce a total volume of 100 ml) may be combined to prepare a suspension in accordance with methods known to the art for the preparation of suspensions. A 100 ml darkly colored bottle bottle may then be filled with the suspension and sterilized.

Alternatively, zerumbone, a sesquiterpene, and/or other agent(s), compound(s), or drug(s) of the present invention (200 mg), Glutathione (200 mg), Isomerized sugar (20 g), Sugar (20 mg), Sodium arginate (100 mg), Orange Flavor (in appropriate amounts) and distilled water added to achieve a total volume of 100 ml may be combined to form a suspension in accordance with methods known to the art for the preparation of suspensions. A 100 ml darkly colored bottle bottle may then be filled with the suspension and sterilized.

Example 35: A Polyethylene Coated Preparation for Administering the Agents, Compounds, or Drugs of the Present Invention Zerumbone, a sesquiterpene, and/or other agent(s), compound(s), or drug(s) of the present invention (250 mg), Glutathione (200 mg), Lactose (30 mg), Starch (20 mg) and Magnesium stearate (in appropriate amounts) may be combined to fill a polyethylene coated envelope and sealed to prepare a powder.

Example 36: A Soft Capsule for Administering the Agent(s), Compound(s), or Drug(s) of the Present Invention Polyethylene glycol (400 mg) may be mixed with concentrated glycerin (55 mg) before adding distilled water (35 mg). The mixture may then be maintained at 60° C. Afterwards, zerumbone and/or other agent(s), compound(s), or drug(s) of the present invention (200 mg) and Glutathione (200 mg), may be added. The mixture may then be stirred to uniformity at approximately 1,500 rpm, and then cooled to room temperature under slow stirring. When air bubbles are removed with a vacuum pump, the remaining mixture is appropriate for inclusion in a soft capsule. The soft capsule membrane may have been manufactured according to methods known to the art using a widely known soft gelatin-plasticizer formula containing gelatin (132 mg), concentrated glycerin (52 mg), 70% disorbitol solution (6 mg per capsule), an appropriate amount of ethyl vanillin flavoring agent, and carnauba wax as the coating agent.

Example 37: A Composition for Administering the Agent(s), Compound(s), or Drug(s) of the Present Invention A composition containing Zerumbone, a sesquiterpene, or other agent(s), compound(s), or drug(s) of the present invention, glutathione, vitamin C and vitamin E and having a synergistic effect. Zerumbone and/or other agent(s), compound(s), or drug(s) of the present invention, vitamin C, and vitamin E may be combined in a weight ratio of 1-50:0.01 to 50:0.01 to 50 along with at least one pharmaceutically acceptable carrier. The composition is formulated into a tablet, hard gelatin capsule, soft gelatin capsule, liquid or suspension, or an injected solution. For example, 50 mg Zerumbone, a sesquiterpene, and/or other agent(s), compound(s), or drug(s) of the present invention, 200 mg vitamin C, 200 mg vitamin E and a suitable amount of an excipient are combined for administration to a human or animal.

Example 38: A Liquid, Nutritional Supplement Comprising the Agents, Compounds, or Drugs of the Present Invention A liquid nutritional supplement may be prepared by combining agents, compounds, or drugs of the present invention (e.g. zerumbone) (5 g), glutathione (4 g), with electrolytes: sodium (at about 170 mg), potassium (at about 600 mg), calcium (at about 400 mg), chloride (about 500 mg), phosphate (at about 400 mg), magnesium at about 100 mg; vitamins and minerals: iron (about 5 mg), Folic acid (at about 200 mcg), Pantothenic acid (at about 2.5 mg), Biotin (about 10 mcg), selenium (at about 30 mcg), manganese (about 1 mg), molybdenum (about 25 mcg), chromium (about 35 mcg), vitamin A (about 1000 IU), vitamin B1 (at about 1 mg), Niacin (about 10 mg), vitamin B2 (at about 1 mg), vitamin B6 (at about 1 mg), vitamin B12 (at about 10 mg), vitamin C (about 60 mg), vitamin D (about 200 IU), vitamin E (about 30 IU), iodine (about 60 mcg), and (optionally) vitamin K (about 30 mcg). Vitamin K is excluded in formulations for individuals taking certain anticoagulation medicines. The liquid composition further contains additional sources of amino acids/protein (about 11 g (from glutathione, milk protein concentrate, calcium caseinate and sodium caseinate) or about 16%, Carbohydrate (about 45 g (inclusive of about 25% sugar compounds or at about 50%), Fat (about 14 g at about 34% (preferably with the majority being unsaturated fat and including omega 3 fatty acids and about 10 mg cholesterol)), Water (at about 180 mL or about 770/1000 ml), and appropriate or desirable amounts of Flavorings (e.g. chocolate sugar, French vanilla, cherry, pecan, mint, cherry, rocky road, ginger, chocolate chip, oreo, strawberry, etc.) and preservatives. Preferably the method of formulation conforms to Kosher and Halal standards.

Example 39

A powder for preparing a nutritional drink comprising the ingredients of example 38 in dried form with appropriate preservatives.

Example 40

A food mixture for baking comprising the ingredients of example 39 to which an appropriate amount of flour, eggs, baking powder or other rising agent is added.

Example 41

A seasoning or condiment comprising agents, compounds, or drugs of the present invention for addition to foods To prepare a seasoning comprising agents, compounds, or drugs of the present invention, about about 1-2 g of zerumbone and/or other agent(s), compound(s), or drug(s) of the present invention is mixed with varying amounts of seasonings to a total amount of about 5 g. Examples of seasonings useful in the invention include saline seasonings (e.g. salt, spiced salt, saltpeter), acid seasonings (e.g. vinegar (sodium diacetate), or vinegar aromatized with tarragon; verjuice, lemon and orange juices), hot seasonings (e.g. peppercorns, ground or coarsely chopped pepper, or mignonette pepper; paprika, curry, cayenne, and mixed pepper spices), saccharine seasonings (e.g. sugar and honey).

Likewise, a condiment comprising agents, compounds, or drugs of the present invention, may be prepared by mixing about 1-2 g of agent(s), compound(s), or drug(s) of the present invention with varying amounts of condiments to a total amount of about 5 g. Examples of condiments to be mixed with the agent, compound or drug include pungents (e.g. onions, shallots, garlic, chives, and horseradish), hot condiments (e.g. mustard, gherkins, capers, English sauces, such as Worcestershire, Baron Green Seasoning, Harvey, ketchup, etc. and American sauces such as chili, Tabasco, A-1 Steak Sauce, etc.), wines used in reductions and braisings, finishing elements of sauces and soups, and fatty substances (e.g. animal fat, butter, edible oils and margarine. If the condiments or seasonings are cooked ones, the agent, compound or drug of the present invention will typically be added to the other ingredients after they have been cooked and cooled.

Example 42. Production of a "Gummy" Containing the Agent(s), Compound(s) or Drug(s) of the Present Invention To prepare 100 g of gummy, about 10-200 mg of the the agent(s), compound(s) or drug(s) of the present invention are mixed with about 6.1 g protein, about 75 g carbohydrate (of which 56.2 g is sugar), about 0.2 g fat (of which 0.2 g is saturated fat), 0.03 g sodium, and 0.08 g equivalents as salt—these amounts being derived from glucose syrup, sugar, modified corn starch, concentrated vegetable extracts (e.g. black carrot, spinach, stinging nettle, turmeric, flavorings, glazing agent canuba wax, paprika extract, lutein. The ingredients may be combined by any methods known to the art for producing a gummy.

Example 43: Preparation of a Carbonyl-Containing Sesquiterpene from a Sesquiterpene Hydrocarbon Having One Olefinic Linkage in the Endocyclic Position A 6-liter glass reactor that is equipped with a stirrer, a dropping-funnel, and a reflux condenser, may be charged with 6 moles of a sesquiterpene hydrocarbon having one olefinic linkage as well as 975 g ethyl formate (13.2 moles). The contents may then be heated to about 57° C. At this point, 975 g. hydrogen peroxyde (concentration 30% by wt., 8.6 moles) may be added at such rate that no excessive foaming occurs (1-2 hours) after which refluxing is continued for another 6 hours. During the reaction the temperature will gradually increase to about 73° C. The reaction mass is then cooled to about 25° C. and the aqueous bottom layer drained off and discarded. The top layer is then to be washed in succession with 900 ml saturated sodium bicarbonate solution and 900 ml water and then dried over anhydrous magnesium sulphate. The resulting sesquiterpene may then be incorporated into a composition or formulation of the present invention as described in the accompanying examples described herein.

Example 44: Formulations Comprising a NO-Containing Derivative from the Agents, Compounds, and Drugs of the Present Invention Agents, compounds, and drugs of the present invention (e.g. a sesquiterpene or flavonoid) may be modified to bear a nitric oxide (NO) donating moiety by any means known to the art (e.g. WO92/01668, WO 95/30641, WO 97/16405; U.S. Pat. No. 5,859,053; WO/2002/011706; WO2010118968) and subsequently incorporated into the formulations described herein.

Example 45: Formulations Comprising a Biotinylated Derivative from the Agents, Compounds, and Drugs of the Present Invention Agents, compounds, and drugs of the present invention may be modified by biotinylation (e.g. U.S. Pat. Nos. 4,794,082; 5,521,319), and subsequently incorporated into the formulations described herein.

Example 46: Preparation of a Tripepetide Composed of Allicin, L-Glutamate, and Glycine The tripepetide wherein allicin is substituted for cysteine is synthesized according to any method known to the art (e.g. U.S. Pat. Nos. 4,332,892; 5,968,767; Spirin and Swartz, 2008).

Example 47: Sublingual Composition

To prepare a sublingual composition of the agent(s), compound(s), or drug(s) of the present invention may be combined with a rapidly dissolving base comprising a polyethylene glycol such as PEG (3350, 1450 or 4500) mannitol, sodium bicarbonate, citric acid, and sucrose, acesulfame potassium, and a flavoring such as raspberry flavor concentrate.

The sublingual composition may comprise an the agent, compound, or drug of the present invention (0.5-5.0 g), PEG 60 g, silica gel 0.56 g, polysorbate 80 3.75 ml, an artificial sweetener such as nutrasweet 0.56 g and sodium saccharine

Example 48: A Transdermal Patch

To prepare a transdermal patch suitable for administration of the agent, compound or drug, the patch will comprise from about 7 mg to about 21 mg of the agent, compound or drug dosage. The transdermal patches comprise about 7, about 14 or about 21 mg dosage for use in preferred methods of the invention. Such patches may further comprise ethylene vinyl-acetate-copolymer, polyisobutylene and high density polyethylene between pigmented and clear polyester backings. Transdermal patches will in general be applied to dry, clean and hairless skin; worn for about 24 hours and a new one put on after rising the next day); and removing the old patch, cleaning the skin, and replacing the new or used patch at approximately the same time every day as directed by a clinician.

Example 49: Additional Synthesis Involving Agents, Compounds, and Drugs of the Present Invention a) Preparation of Mono-Phenyl Analogs with Improved Activity Boric anhydride (0.7 eq) may be added to a solution of 2,4-pentanedione or 4-acetyl-5-oxo-hexanoate in EtOAc (3 eq). The solution is stirred at 70° C. for 0.5 h. To the solution, the agent, compound, or drug of the present invention (1 eq) and tributyl borate (1 eq) are then added. The mixture is stirred for another 30 min. At 85° C., butylamine (1 eq) dissolved in EtOAc is added dropwise over 15 min. The stirring continued for 1 h at 100° C. The mixture is then hydrolyzed by adding 1N HCl at 50° C. and stirring for 0.5 h at 50° C. The organic layer is separated, and the aqueous layer may be extracted with EtOAc. The combined organic layers are washed until neutral and dried over anhydrous sodium sulfate. After removing the solvent in vacuo, the crude products were purified by flash column chromatography eluting with a hexane-EtOAc gradient.

b) Preparation of Heterocycle-Containing Analogs with Improved Activity

An agent, compound, or drug of the present invention along with boric anhydride (0.7 equiv.) may be dissolved in EtOAc and stirred at 70° C. for 30 min. An appropriate benzaldehyde (1 equiv.) and tributylborate (2 equiv.) may be added, and the mixture stirred for a further 30 min. Piperidine, having been dissolved in EtOAc, may be added dropwise. After increasing the temperature to 100° C., stirring is continued for 1 h. The mixture is then hydrolyzed by adding 1N HCl, and stirring at 60° C. for 0.5 h. The organic layer is separated, and the aqueous layer is extracted with EtOAc three times. The combined organic layers were washed with water until neutral. The solvent is removed in vacuo. The crude products may be purified by flash column chromatography, eluting with hexane-EtOAc.

c.) 1.5 ml of a 25% w/w aqueous solution of cetyltrimethylammonium bromide is added to a solution composed of an agent, compound, or drug of the present invention (10 mmol) in 50 ml of a 0.25 M solution of aqueous NaOH with acetone (0.36 ml, 5 mmol). The mixture is allowed to stir vigorously at room temperature for 20 h, diluted with brine and extracted with EtOAc. The EtOAc solution is concentrated and then subjected to column chromatography to obtain the target product.

d) To a solution of acetaldehyde (0.84 ml, 15 mmol) in EtOH (10 ml), 3 M NaOH (5 ml, 15 mmol) is added at 0° C. The solution is stirred for an additional 20 min. Afterwards, an agent, compound, or drug of the present invention (15 mmol) in EtOH (5 ml) is added to the stirring solution dropwise, the reaction is brought to room temperature and stirred for 2 h. Then the mixture is poured into water and adjusted to pH 7 by adding 1N HCl. After extraction with EtOAc, the organic layer is washed with water three times and dried over anhydrous sodium sulfate. After removal of the solvent under vacuum, the crude product is purified with flash column chromatography.

e) To a stirring solution of lithium diisopropylamine (0.29 ml, 0.58 mmol) in THF (3 ml), a THF (3 ml) solution of 3,4-dimethoxycinnamone (100 mg, 0.48 mmol) may be added at −78° C. After 15 min, an agent, compound, or drug of the present invention (0.5 mmol) in THF (3 ml) is added and stirred for an additional 20 min at −78° C. Then, the mixture is quenched with saturated NH4Cl solution. The solution is allowed to warm to ambient temperature and extracted with EtOAc. The organic layer is washed with water and saturated NaCl solution and dried over anhydrous sodium sulfate. The crude product is purified by flash column chromatography.

Example 50

An agent, compound or drug of the present invention (3 mmol) is dissolved in 15 mL of dry methylene chloride. Thionyl chloride (0.3 mL, 3.6 mmol) is added at 0° C. The solution is stirred under reflux for 5 h. The solvent is removed under vacuum to give a solid. In the same flask, 10 mL of anhydrous THF is added, and the mixture heated to reflux. HMDA (0.3 mL) is added very slowly to the refluxing solution, followed by the addition of triethylamine (0.4 mL).

The solution is stirred under reflux overnight. The solvent is then removed in vacuo. The solid is extracted with CH2Cl2× 3. The combined CH2Cl2 solution is washed with water three times and brine once, and then dried over anhydrous sodium sulfate. The crude product is obtained after flash column chromatography.

Example 51

To prepare a bovine serum albumin (BSA) conjugated agent, compound, or drug of the present invention, nitrous acid may be generated by the addition of a solution of 0.85 niEq of sodium nitrite to an excess of HCl. This reaction can be maintained at a temperature of 5° C. A solution of 0.85 mEq of 4-aminobenzoic acid in 1N HCl chilled to 50 C may be prepared with continuous stirring in ice bath for 20 minutes, not exceeding the pH of 1.0. Diazotized 4-minobenzoic acid may then be added dropwise to an equivalent concentration, (0.85 mEq) of the agent, compound, or drug of the present invention (compound I) dissolved in ethanol at pH 11.0 with continuous stirring at 50 C.

The solution is then to be acidified to pH 2.0 at which time the derivative (compound II) is precipitated. The precipitate may be centrifuged and redissolved in ethanol at pH 11.0 again. After repeating the acid and base cycle twice, the crude derivative (II) can be chromatographed on a column of silica gel. Reduced pressure evaporation of the elution solvent will give a derivative of about 98% purity as checked by TLC. The bovine serum albumin conjugate (III), of this invention may then be synthesized in a medium of 1% NaCl/dioxane/NaOH solution of pH 8-10, at 50 C, by adding 0.1M solution of 1-cyclohexyl-3-(2-morpholinoethyl) carbodiimide metho-p-toluene sulfonate to the purified crystalline derivative (compound II) in the same medium with continuous stirring. Bovine serum albumin is then to be added to the foregoing mixture at 50 C, pH 8-10 with continuous stirring for 1 hr until the intermediate azopseudourea has conjugated to bovine serum albumin, after which the mixture is to be centrifuged off, acidified to pH 4.2, salted out, recentrifuged, redissolved then dialyzed for 24 hr at 50 C against 0.5M sodium carbonate, pH 8.2 until the reaction is complete (or about 2 hours). A final dialysis is performed against bi-distilled water for 24 hours at 5° C., after which the protein conjugate (III) may be lyophilized.

Example 52: Synthesis of Additional Analogs and Derivatives

In one embodiment, the agents, compounds or drugs of the present invention are modified by chlorination, addition of an imidazole, a methyl amide, the formation of additional amide derivatives, such as the ethyl amides, and/or fluorination of imidazole and amide derivatives. The current invention encompasses derivatives with varying substituent groups (e.g., substituted and unsubstituted carbonyl imidazoles, cyano, esters, glycosides, and amides). Accordingly, reactions relating to the preparation additional analogs and derivatives may be accomplished according to the methods of U.S. Pat. Nos. 4,550,176; 5,389,634; Johnson and Shelberg, 1945; Clinton et al., 1961; Dean, 1965; and Sharpless et al, 1973. For example, derivatives may be produced according to schemes comprising the following steps:
  1. Formylation in the presence of sodium methoxidein benzene (Clinton et al., 1961).
  2. Introducing a double bond with phenylselenenyl chloride with sequential addition of 30% hydrogen peroxide (Sharpless et al, 1973) followed by halogenolysis (Dean, 1965).
  3. Formylation in sodium methoxide (Clinton et al., 1961).
  4. Introducing a double bond with phenylselenenyl with sequential addition of 30% hydrogen peroxide (Sharpless et al, 1973).
  5. Cleavage with sodium methoxide (Johnson and Shelberg, 1945). Example 53: A topical formulation suitable for treating acne or disorder of the skin Example 53. A Lotion Comprising an Agent Compound or Drug of the Present Invention To prepare a lotion comprising an agent compound or drug of the present invention (e.g zerumbone and/or other agent(s), compound(s), or drug(s) of the present invention) in combination with benzoyl peroxide 2.5%, and inert ingredients selected from water, allantoin, aloe barbadensis leaf juice, aluminum silicate, benzophenone-4, carbomer, cetearyl alcohol, cetyl esters, ceteareth-20, color agents, cyclomethicone, diazolidinyl urea, dimethicone, dimethyl isosorbide, disodium dimethicone copolyol sulfosuccinate, ethoxydiglycol, flower extract, fruit extract, fragrance agents, glycerinhydroxyethylcellulose, glycolic acid, glyceryl stearate, *hamamelis virginiana* (witch hazel) extract, imidazolidinyl urea, imidazolidinyl urea, magnesium methylparaben, neopentyl glycol dicaprylate, neopentyl glycol dicaprate, panthenol, PEG-100 stearate, polyethylene, polysorbate-20, propylene glycol, propylparaben, sodium hyaluronate, sodium hydroxide, sodium PCA, sorbitol, stearate, tridecyl trimellitate, tetrasodium EDTA, triethanolamine, tridecyl stearate, and xanthan gum.

Example 54: A Topical Formulation Promoting Absorption

To prepare a topical formulation comprising water (66%), propylene glycol (5%), Sepigel 305 (2%), Mygliol 812 (4%), and Cremophor RH40 (4%), and active ingredients (agent(s), compound(s), or drug(s) of the present invention) (19%), may be added in small portions to a mixture of cremophor and mygliol, at temperatures below that at which the active ingredients are degraded. An aqueous phase may be prepared by adding Sepigel 305 in small amounts with continuous slow mixing to the solution of water and propylene glycol. The final formulation may be achieved by adding the oily phase to the aqueous one prior to storage in refrigerator.

Example 55: A "Vanishing Cream" Formulation with Ointment and Cream Properties

To prepare a vanishing cream formulation, zerumbone, a sesquiterpene, and/or other agent(s), compound(s), or drug(s) of the present invention (1-10% w/w), may be added to preservative, methyl paraben i. p. (0.08% w/w), propyl paraben i.p. (0.04% w/w) and excipients.

Example 56

Cultured *L. donovani* promastigotes were exposed to the typical serum concentrations of metronidazole, itraconazole, and ciprofloxacin in clinical settings (e.g. 5 ug/ml) either alone or in two-drug combinations. While ciprofloxacin had limited effects on promastigote motility and growth in DMEM culture medium, the combination of metronidazole and itraconazole led to a 95% reduction of promastigotes after 144 hours in culture compared to control. Metronidazole/itraconazole also completely inhibited cell motility in the surviving promastigotes. Metronidazole or itraconazole alone caused a significant, but more modest reduction (~50%) in cultured promastigotes at 144 hours indicating the drugs displayed synergistics effects on promastigote killing.

Accordingly, agents, compounds, or drugs belonging to the classes represented by metronidazole and itraconazole may be included in the formulations described in the previous examples to provide for a therapy effective in preventing or treating a parasitic disease, especially a protozoal disease.

INDUSTRIAL APPLICABILITY

The pharmaceutical composition comprising agents, compounds and drugs of the present invention (e.g. a sesquiterpene lactone and/or other agent(s), compound(s), or drug(s) of the present invention) are clinically useful in preventing or treating various human diseases. "Comprises/comprising" when used in this specification is taken to specify the presence of stated features, integers, steps or components but does not preclude the presence or addition of one or more other features, integers, steps or components or groups thereof.

The invention claimed is:

1. A method for reducing motility of *L. donovani* cells, said method comprising contacting the *L. donovani* cells with an effective amount of a composition, the composition comprising a combination of metronidazole and itraconazole, wherein the effective amount is sufficient to reduce motility of the *L. donovani* cells.

* * * * *